US009328075B2

(12) United States Patent
Webb et al.

(10) Patent No.: US 9,328,075 B2
(45) Date of Patent: May 3, 2016

(54) PYRIMIDINONE COMPOUNDS AND METHODS FOR TREATING INFLUENZA

(75) Inventors: Thomas R. Webb, Millington, TN (US); Vincent A. Boyd, Germantown, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

(21) Appl. No.: 14/115,560

(22) PCT Filed: May 5, 2012

(86) PCT No.: PCT/US2012/036697
§ 371 (c)(1),
(2), (4) Date: Nov. 4, 2013

(87) PCT Pub. No.: WO2012/151567
PCT Pub. Date: Nov. 8, 2012

(65) Prior Publication Data
US 2014/0079666 A1    Mar. 20, 2014

Related U.S. Application Data

(60) Provisional application No. 61/482,749, filed on May 5, 2011.

(51) Int. Cl.

| | | |
|---|---|---|
| C07D 239/54 | (2006.01) |
| C07D 401/04 | (2006.01) |
| C07D 401/12 | (2006.01) |
| C07D 403/04 | (2006.01) |
| C07D 487/04 | (2006.01) |
| A61K 31/13 | (2006.01) |
| A61K 31/59 | (2006.01) |
| A61K 38/21 | (2006.01) |
| A61K 45/06 | (2006.01) |
| A61K 31/4045 | (2006.01) |
| A61K 31/5377 | (2006.01) |
| A61K 31/7012 | (2006.01) |
| A61K 31/551 | (2006.01) |
| A61K 31/505 | (2006.01) |
| A61K 31/506 | (2006.01) |
| A61K 31/519 | (2006.01) |
| A61K 31/196 | (2006.01) |
| A61K 31/215 | (2006.01) |
| A61K 31/351 | (2006.01) |

(52) U.S. Cl.
CPC .............. *C07D 239/54* (2013.01); *A61K 31/13* (2013.01); *A61K 31/196* (2013.01); *A61K 31/215* (2013.01); *A61K 31/351* (2013.01); *A61K 31/4045* (2013.01); *A61K 31/505* (2013.01); *A61K 31/506* (2013.01); *A61K 31/519* (2013.01); *A61K 31/5377* (2013.01); *A61K 31/551* (2013.01); *A61K 31/59* (2013.01); *A61K 31/7012* (2013.01); *A61K 38/21* (2013.01); *A61K 45/06* (2013.01); *C07D 401/04* (2013.01); *C07D 401/12* (2013.01); *C07D 403/04* (2013.01); *C07D 487/04* (2013.01)

(58) Field of Classification Search
CPC ..... A61K 31/13; A61K 31/59; A61K 31/196; A61K 31/215; A61K 31/351; A61K 31/505; A61K 31/506; A61K 31/519; A61K 31/551; A61K 31/4045; A61K 31/5377; A61K 31/7012; A61K 38/21; A61K 45/06; C07D 239/54; C07D 401/04; C07D 401/12; C07D 403/04; C07D 487/04
USPC .......... 424/408, 409, 451, 464, 489; 514/256, 514/258.1, 259.1, 259.5, 269, 272, 274, 514/275; 544/242, 245, 253, 282, 322, 324, 544/326, 328, 329, 331, 332, 333, 334, 335
See application file for complete search history.

(56) References Cited

U.S. PATENT DOCUMENTS

| 8,673,884 | B2 * | 3/2014 | Jones et al. ...................... 514/86 |
| 2005/0130997 | A1 * | 6/2005 | Avolio et al. ................. 514/269 |
| 2005/0256109 | A1 * | 11/2005 | Naidu ........................ 514/222.5 |
| 2011/0201665 | A1 * | 8/2011 | Altmeyer ............... A61K 31/16 514/424 |

FOREIGN PATENT DOCUMENTS

| WO | WO 2009/097682 A1 | 8/2009 |
| WO | WO 2012/151567 | 11/2012 |

OTHER PUBLICATIONS

Das et al., Structures of influenza A proteins and insights into antiviral drug targets; May 2010; Nature Structural & Molecular Biology, 17(5):530-538.*
Dias et al., The cap-snatching endonuclease of influenza virus polymerase resides in the PA subunit; Apr. 2009; Nature, 458:914-918.*
Boyd et al., 2-Substituted-4,5-Dihydroxypyrimidine-6-Carboxamide Antiviral Targeted Libraries; Jul. 2009; J. Comb. Chem., 11:1100-1104.*
V. Boyd et al., "2-Substituted-4,5-Dihydroxypyrimidine-6-Carboxamide Antiviral Targeted Libraries," 2009; J. Comb. Chem. 11:1100-1104.*
Boyd et al. (2009) 2-Substituted-4,5-dihydroxypyrimidine-6-carboxamide antiviral targeted libraries. *J. Comb. Chem.* 11(6): 1100-1104.
Baughman et al. (2012) Identification of Influenza Endonuclease Inhibitors via a Novel Fluorescence Polarization Assay. *ACS Chem. Biol.* 7(3): 526-534.
De Clercq, E. (2005) Recent highlights in the development of new antiviral drugs. *Current Opinion in Microbiology* 8: 552-560.
DuBois et al. (2012) Structural and Biochemical Basis for Development of Influenza Virus Inhibitors Targeting the PA Endonuclease. *PLoS Pathog.* 8(8): e1002830.
Su et al. (2010) High-throughput identification of compounds targeting influenza RNA-dependent RNA polymerase activity. *PNAS* 107(45): 19151-19156.
International Search Report and Written Opinion issued Sep. 25, 2012 for Intl. Pat. App. No. PCT/US12/36697, which was filed May 5, 2012 and published as WO 2012/151567 on Nov. 8, 2012 (Inventor—Webb et al.) (pp. 1-8).
U.S. Appl. No. 61/482,749, filed May 5, 2011, Thomas R. Webb.

* cited by examiner

*Primary Examiner* — Jane C Oswecki
(74) *Attorney, Agent, or Firm* — Ballard Spahr LLP

(57) ABSTRACT

In one aspect, the invention relates to novel, broad-spectrum anti-viral, pyrimidinone compounds, methods of use, compositions and kits useful in treating and/or preventing influenza. This abstract is intended as a scanning tool for purposes of searching in the particular art and is not intended to be limiting of the present invention.

26 Claims, No Drawings

PYRIMIDINONE COMPOUNDS AND METHODS FOR TREATING INFLUENZA

CROSS-REFERENCE TO RELATED APPLICATIONS

This application claims the benefit of U.S. Provisional Application No. 61/482,749, filed on May 5, 2011, which is incorporated herein by reference in its entirety.

BACKGROUND

Influenza virus is a single-stranded RNA virus in the Orthomyxoviridae family. The virus is responsible for seasonal influenza. Approximately 200,000 hospitalizations and about 36,000 deaths per year are attributable to the influenza virus. On occasion, a novel antigenic strain of influenza virus evolves to cause a pandemic. These influenza pandemics usually occur about three times per century, causing an infectious threat to human beings. Typically, the pandemics occur when novel influenza A viruses infect the human population. As examples of these pandemics, the 1918 Spanish influenza pandemic infected 25-40% of the world's population, killing twenty to one hundred million people. In 1957 and 1968, approximately one million people were killed during those pandemics. More recently, in April 2009, H1N1 influenza viruses have spread throughout the world, with an estimated 1,483,520 confirmed cases that lead to 25,174 deaths. The potential for another pandemic realizes the need for targeted therapeutic and improved prophylactic agents to battle emerging influenza viruses. H1N1 vaccines are in clinical trials in the United States, but antiviral drugs and non-pharmaceutical means of controlling infections are probably the first line defenses against the disease. Also of importance is the fact that elderly patients, infants and people with compromised immune systems may have a more limited response to vaccination.

At this point in time, there are two options for treating influenza. One option is use of M2 ion channel blockers, such as amantadine that blocks endocytosis and cell fusion. The other option is the use of neuraminidase inhibitors such as oseltamivir and zanamivir that block viral release. However, amantadine has become very ineffective as a treatment, and oseltamivir seems to require much higher doses for treatment in murine models.

Without wishing to be bound by theory, it is believed that the identification of novel targets in the influenza viral lifecycle have resulted in novel therapeutic compounds. The criteria for the development of broad spectrum anti-virals include a specificity for virus infected cells, broad conservation among virus strains, indispensability for viral replication and the development for orally-active drug candidates. This research has led to the identification of influenza protein targets, such as PA, PB1, PB2 and nucleoproteins.

As an example of some of the early work in this targeted research, Merck scientists reported the discovery of dioxobutanoic acid and flutimide as inhibitors of the endonuclease activity of influenza RNA dependent RNA polymerase (IRdRp). The resultant work suggested the possibility that IRdRp inhibitors would be useful as anti-viral agents. Later, a small prodrug (T-705) that is converted to the ribonucleoside triphosphate was determined to be a selective inhibitor of the IRdR polymerase and is currently in Phase III clinical trials in Japan. It is the specificity of T-705 against influenza A, B and C in vivo that validates IRdRp as a promising target for developing influenza therapy. In this context, the IRdRp inhibitors are attractive targets for the development of antivirals to treat and prevent influenza.

Therefore, there remains a need for anti-viral compounds to prevent and treat influenza virus. It is this need that has led to the identification of novel compounds and methods of treating and preventing influenza virus. These needs and others needs are met by the present invention.

SUMMARY

In accordance with the purpose(s) of the invention, as embodied and broadly described herein, the invention, in one aspect, relates to compounds and methods useful in the treatment of influenza.

Disclosed are methods for preventing or treating influenza in a subject, the method comprising: administering to the subject an effective amount of a compound of the formula:

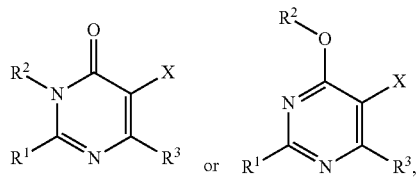

wherein X is selected from hydroxyl, fluoro, chloro, bromo, —OR$^7$, —NR$^{11}$R$^{12}$, —NR$^{11}$COR$^{12}$, —NR$^{11}$CO$_2$R$^{12}$, and —NR$^{11}$CONR$^{12}$R$^{13}$; wherein R$^1$ is optionally substituted and selected from aryl, heteroaryl, aryl-substituted alkyl, heteroaryl-substituted alkyl, —NR$^{11}$R$^{12}$, —NR$^{11}$COR$^{12}$, —NR$^{11}$CO$_2$R$^{12}$, —NR$^{11}$CONR$^{12}$R$^{13}$, —COR$^{11}$, —CONR$^{12}$R$^{13}$, and —OR$^7$; wherein R$^2$ is optionally substituted, where permitted, and selected from hydrogen, alkyl, heteroalkyl, cycloalkyl, heterocycloalkyl, aryl, and heteroaryl; or wherein R$^1$ and R$^2$ together form an optionally substituted ring with the carbon and nitrogen to which they are attached, selected from pyrrolidinyl, imidazolidinyl, hexahydropyrimidinyl, 1,3,5-triazinanyl, and piperidinyl; wherein R$^3$ is optionally substituted and selected from cycloalkyl, heterocycloalkyl, aryl, heteroaryl, —NR$^{11}$R$^7$, —NR$^{11}$COR$^{12}$, —NR$^{11}$CO$_2$R$^7$, —NR$^{11}$CONR$^{12}$R$^{13}$, —NR$^{11}$SO$_2$R$^{12}$, —SO$_2$NR$^{12}$R$^{13}$, —CONR$^4$R$^5$, and —COR$^6$; wherein R$^4$ and R$^5$ are each optionally substituted where permitted and independently selected from hydrogen, alkyl, heteroalkyl, cycloalkyl, heterocycloalkyl, aryl, and heteroaryl; or wherein —NR$^4$R$^5$ together form an optionally substituted ring selected from piperidinyl, morpholinyl, and piperazinyl; wherein R$^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein R$^7$ is selected from alkyl, heteroalkyl, cycloalkyl, heterocycloalkyl, aryl, and heteroaryl; and wherein each of R$^{11}$, R$^{12}$, and R$^{13}$, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof, thereby preventing or treating the influenza.

Also disclosed are methods for inhibiting development of influenza virus in a mammal, the method comprising: administering to the mammal an effective amount of at least one compound of the formula:

or
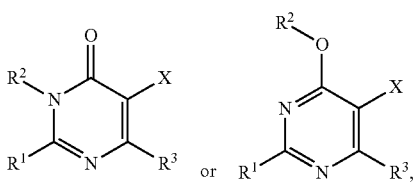

wherein X is selected from hydroxyl, fluoro, chloro, bromo, —$OR^7$, —$NR^{11}R^{12}$, —$NR^{11}COR^{12}$, —$NR^{11}CO_2R^{12}$, and —$NR^{11}CONR^{12}R^{13}$; wherein $R^1$ is optionally substituted and selected from aryl, heteroaryl, aryl-substituted alkyl, heteroaryl-substituted alkyl, —$NR^{11}R^{12}$, —$NR^{11}COR^{12}$, —$NR^{11}CO_2R^{12}$, —$NR^{11}CONR^{12}R^{13}$, —$COR^{11}$, —$CONR^{12}R^{13}$, and —$OR^7$; wherein $R^2$ is optionally substituted, where permitted, and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl;

wherein $R^3$ is optionally substituted and selected from cycloalkyl, heterocycloalkyl, aryl, heteroaryl, —$NR^{11}R^7$, —$NR^{11}COR^{12}$, —$NR^{11}CO_2R^7$, —$NR^{11}CONR^{12}R^{13}$, —$NR^{11}SO_2R^{12}$, —$SO_2NR^{12}R^{13}$, —$CONR^4R^5$, and —$COR^6$; wherein $R^4$ and $R^5$ are each optionally substituted where permitted and independently selected from hydrogen, alkyl, heteroalkyl, cycloalkyl, heterocycloalkyl, aryl, and heteroaryl; or wherein —$NR^4R^5$ together form an optionally substituted ring selected from piperidinyl, morpholinyl, and piperazinyl; wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein $R^7$ is selected from alkyl, heteroalkyl, cycloalkyl, heterocycloalkyl, aryl, and heteroaryl; and wherein each of $R^{11}$, $R^{12}$, and $R^{13}$, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof, thereby inhibiting development of influenza virus in the mammal Also disclosed are methods for decreasing influenza virus activity in at least one cell, the method comprising contacting the cell with an effective amount of least one compound of the formula:

or wherein X is selected from hydroxyl, fluoro, chloro, bromo, —$OR^7$, —$NR^{11}K$, —$NR^{11}COR^{12}$, —$NR^{11}CO_2R^{12}$, and —$NR^{11}CONR^{12}R^{13}$; wherein $R^1$ is optionally substituted and selected from aryl, heteroaryl, aryl-substituted alkyl, heteroaryl-substituted alkyl, —$NR^{11}R^{12}$, —$NR^{11}COR^{12}$, —$NR^{11}CO_2R^{12}$, —$NR^{11}CONR^{12}R^{13}$, —$COR^{11}$, —$CONR^{12}R^{13}$, and —$OR^7$; wherein $R^2$ is optionally substituted, where permitted, and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl;

wherein $R^3$ is optionally substituted and selected from cycloalkyl, heterocycloalkyl, aryl, heteroaryl, —$NR^{11}R^7$, —$NR^{11}COR^{12}$, —$NR^{11}CO_2R^7$, —$NR^{11}CONR^{12}R^{13}$, —$NR^{11}SO_2R^{12}$, —$SO_2NR^{12}R^{13}$, —$CONR^4R^5$, and —$COR^6$; wherein $R^4$ and $R^5$ are each optionally substituted where permitted and independently selected from hydrogen, alkyl, heteroalkyl, cycloalkyl, heterocycloalkyl, aryl, and heteroaryl; or wherein —$NR^4R^5$ together form an optionally substituted ring selected from piperidinyl, morpholinyl, and piperazinyl; wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein $R^7$ is selected from alkyl, heteroalkyl, cycloalkyl, heterocycloalkyl, aryl, and heteroaryl; and wherein each of $R^{11}$, $R^{12}$, and $R^{13}$, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof, thereby decreasing influenza virus activity in the cell.

Also disclosed are methods for decreasing endonuclease activity in at least one cell, the method comprising contacting the cell with an effective amount of least one compound of the formula:

or wherein X is selected from hydroxyl, fluoro, chloro, bromo, —$OR^7$, —$NR^{11}R^{12}$, —$NR^{11}COR^{12}$, —$NR^{11}CO_2R^{12}$, and —$NR^{11}CONR^{12}R^{13}$; wherein $R^1$ is optionally substituted and selected from aryl, heteroaryl, aryl-substituted alkyl, heteroaryl-substituted alkyl, —$NR^{11}R^{12}$, —$NR^{11}COR^{12}$, —$NR^{11}CO_2R^{12}$, —$NR^{11}CONR^{12}R^{13}$, —$COR^{11}$, —$CONR^{12}R^{13}$, and —$OR^7$; wherein $R^2$ is optionally substituted, where permitted, and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl;

wherein $R^3$ is optionally substituted and selected from cycloalkyl, heterocycloalkyl, aryl, heteroaryl, —$NR^{11}R^7$, —$NR^{11}COR^{12}$, —$NR^{11}CO_2R^7$, —$NR^{11}CONR^{12}R^{13}$, —$NR^{11}SO_2R^{12}$, —$SO_2NR^{12}R^{13}$, —$CONR^4R^5$, and —$COR^6$; wherein $R^4$ and $R^5$ are each optionally substituted where permitted and independently selected from hydrogen, alkyl, heteroalkyl, cycloalkyl, heterocycloalkyl, aryl, and heteroaryl; or wherein —$NR^4R^5$ together form an optionally substituted ring selected from piperidinyl, morpholinyl, and piperazinyl; wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein $R^7$ is selected from alkyl, heteroalkyl, cycloalkyl, heterocycloalkyl, aryl, and heteroaryl; and wherein each of $R^{11}$, $R^{12}$, and $R^{13}$, when present, is independently selected from hydrogen, alkyl, heteroalkyl, cycloalkyl, heterocycloalkyl, aryl, and heteroaryl; or a pharmaceutically acceptable salt, hydrate, solvate, or polymorph thereof, thereby decreasing endonuclease activity in the cell.

Also disclosed are methods for decreasing polymerase activity in at least one cell, the method comprising contacting the cell with an effective amount of least one compound of the formula:

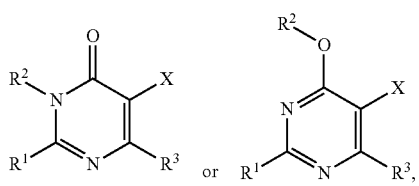

wherein X is selected from hydroxyl, fluoro, chloro, bromo, $-OR^7$, $-NR^{11}R^{12}$, $-NR^{11}COR^{12}$, $-NR^{11}CO_2R^{12}$, and $-NR^{11}CONR^{12}R^{13}$; wherein $R^1$ is optionally substituted and selected from aryl, heteroaryl, aryl-substituted alkyl, heteroaryl-substituted alkyl, $-NR^{11}R^{12}$, $-NR^{11}COR^{12}$, $-NR^{11}CO_2R^{12}$, $-NR^{11}CONR^{12}R^{13}$, $-COR^{11}$, $-CONR^{12}R^{13}$, and $-OR^7$; wherein $R^2$ is optionally substituted, where permitted, and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl;

wherein $R^3$ is optionally substituted and selected from cycloalkyl, heterocycloalkyl, aryl, heteroaryl, $-NR^{11}R^7$, $-NR^{11}COR^{12}$, $-NR^{11}CO_2R^7$, $-NR^{11}CONR^{12}R^{13}$, $-NR^{11}SO_2R^{12}$, $-SO_2NR^{12}R^{13}$, $-CONR^4R^5$, and $-COR^6$; wherein $R^4$ and $R^5$ are each optionally substituted where permitted and independently selected from hydrogen, alkyl, heteroalkyl, cycloalkyl, heterocycloalkyl, aryl, and heteroaryl; or wherein $-NR^4R^5$ together form an optionally substituted ring selected from piperidinyl, morpholinyl, and piperazinyl; wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein $R^7$ is selected from alkyl, heteroalkyl, cycloalkyl, heterocycloalkyl, aryl, and heteroaryl; and wherein each of $R^{11}$, $R^{12}$, and $R^{13}$, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof, thereby decreasing polymerase activity in the cell.

Also disclosed are therapeutic methods comprising co-administration of one or more treatments selected from Oseltamavir, Zanamivir, Amantadine, Rimantadine, Arbidol, Laninamivir, Peramivir, Vitamin D, and an interferon, with one or more compounds of the formula:

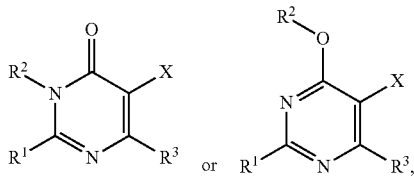

wherein X is selected from hydroxyl, fluoro, chloro, bromo, $-OR^7$, $-NR^{11}R^{12}$, $-NR^{11}COR^{12}$, $-NR^{11}CO_2R^{12}$, and $-NR^{11}CONR^{12}R^{13}$; wherein $R^1$ is optionally substituted and selected from aryl, heteroaryl, aryl-substituted alkyl, heteroaryl-substituted alkyl, $-NR^{11}R^{12}$, $-NR^{11}COR^{12}$, $-NR^{11}CO_2R^{12}$, $-NR^{11}CONR^{12}R^{13}$, $-COR^{11}$, $-CONR^{12}R^{13}$, and $-OR^7$; wherein $R^2$ is optionally substituted, where permitted, and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl;

wherein $R^3$ is optionally substituted and selected from cycloalkyl, heterocycloalkyl, aryl, heteroaryl, $-NR^{11}R^7$, $-NR^{11}COR^{12}$, $-NR^{11}CO_2R^7$, $-NR^{11}CONR^{12}R^{13}$, $-NR^{11}SO_2R^{12}$, $-SO_2NR^{12}R^{13}$, $-CONR^4R^5$, and $-COR^6$; wherein $R^4$ and $R^5$ are each optionally substituted where permitted and independently selected from hydrogen, alkyl, heteroalkyl, cycloalkyl, heterocycloalkyl, aryl, and heteroaryl; or wherein $-NR^4R^5$ together form an optionally substituted ring selected from piperidinyl, morpholinyl, and piperazinyl; wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein $R^7$ is selected from alkyl, heteroalkyl, cycloalkyl, heterocycloalkyl, aryl, and heteroaryl; and wherein each of $R^{11}$, $R^{12}$, and $R^{13}$, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof.

Also disclosed are compounds of the formula:

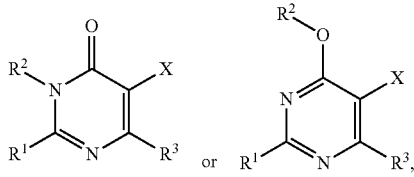

wherein X is selected from hydroxyl, fluoro, chloro, bromo, $-NR^{11}R^{12}$, $-NR^{11}COR^{12}$, $-NR^{11}CO_2R^{12}$, and $-NR^{11}CONR^{12}R^{13}$; wherein $R^1$ is optionally substituted and selected from aryl, heteroaryl, aryl-substituted alkyl, heteroaryl-substituted alkyl, $-NR^{11}R^{12}$, $-NR^{11}COR^{12}$, $-NR^{11}CO_2R^{12}$, $-NR^{11}CONR^{12}R^{13}$, $-COR^{11}$, $-CONR^{12}R^{13}$, and $-OR^7$; wherein $R^2$ is optionally substituted where permitted and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl; wherein $R^3$ is optionally substituted and selected from cycloalkyl; heterocycloalkyl; aryl or heteroaryl, provided that $R^1$ and $R^2$ do not form a ring together with the carbon and nitrogen to which they are attached; —$CONR^4R^5$, and —$COR^6$; wherein $R^4$ and $R^5$ are each optionally substituted, where permitted, and independently selected from hydrogen, alkyl, heteroalkyl, cycloalkyl, heterocycloalkyl, aryl, and heteroaryl; wherein at least one of $R^4$ or $R^5$ is not hydrogen, and provided that when $R^1$ is an aryl or heteroaryl group having 6 or more ring members, then neither $R^3$ nor $R^4$ is hydrogen; or wherein —$NR^4R^5$ together form an optionally substituted ring selected from piperidinyl, morpholinyl, and piperazinyl; wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein $R^7$ is selected from alkyl, heteroalkyl, cycloalkyl, heterocycloalkyl, aryl, and heteroaryl; and wherein each of $R^{11}$, $R^{12}$, and $R^{13}$, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof.

Also disclosed are kits comprising at least one disclosed compound or a pharmaceutically acceptable salt, hydrate, solvate, or polymorph thereof, and one or more of: (a) an antiviral agent; (b) a M2 inhibition agent; (c) a neuraminidase inhibition agent; (d) an agent known to treat flu symptoms; and/or (e) instructions for treating influenza.

Also disclosed are pharmaceutical compositions comprising a therapeutically effective amount of a disclosed compound and a pharmaceutically acceptable carrier.

Also disclosed are methods for manufacturing a medicament comprising combining at least one disclosed compound or at least one disclosed product with a pharmaceutically acceptable carrier or diluent.

Also disclosed are uses of a disclosed compound or a disclosed product in the manufacture of a medicament for the treatment of a disorder associated with a kinase dysfunction in a mammal While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

I. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as ChemDraw™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal A patient refers to a subject afflicted with a disease or disorder. The term "patient" includes human and veterinary subjects. In some aspects of the disclosed methods, the subject has been diagnosed with a need for treatment of a disorder of uncontrolled cellular proliferation associated with a protein kinase dysfunction prior to the administering step. In some aspects of the disclosed method, the subject has been diagnosed with a need for inhibition of a protein kinase prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, zebra fish etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with influenza" means having been subjected to a physical examination by a person of skill, for example, a physician, and found to have influenza. As a further example, "diagnosed with a need for inhibition of endonuclease activity" refers to having been subjected to a physical examination by a person of skill, for example, a physician, and found to have a condition characterized by endonuclease activity. Such a diagnosis can be in reference to a disorder, such as influenza, as discussed herein. For example, the term "diagnosed with a need for treatment of influenza" refers to having been subjected to a physical examination by a person of skill, for example, a physician, and found to have disorder that can be ameliorated by treatment of influenza.

As used herein, the phrase "identified to be in need of treatment for a disorder," or the like, refers to selection of a subject based upon need for treatment of the disorder. For example, a subject can be identified as having a need for treatment of a disorder (e.g., influenza) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, intraurethral administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex, and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism or activation of a biological process, or component of a process, including a protein, subunit, organelle, ribonucleoprotein, etc. In one aspect, an $EC_{50}$ can refer to the concentration of a substance that is required for 50% agonism or activation in vivo, as further defined elsewhere herein. In a further aspect, $EC_{50}$ refers to the concentration of agonist or activator that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. For example, an $IC_{50}$ can refer to the concentration of a substance that is required for 50% inhibition in vivo or the inhibition is measured in vitro, as further defined elsewhere herein. Alternatively, $IC_{50}$ refers to the half maximal (50%) inhibitory concentration (IC) of a substance.

The term "pharmaceutically acceptable" describes a material that is not biologically or otherwise undesirable, i.e., without causing an unacceptable level of undesirable biological effects or interacting in a deleterious manner.

The term "stable," as used herein, refers to compounds that are not substantially altered when subjected to conditions to allow for their production, detection, and, in certain aspects, their recovery, purification, and use for one or more of the purposes disclosed herein.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

For example, a "C1-C3 alkyl" group can be selected from methyl, ethyl, n-propyl, i-propyl, and cyclopropyl, or from a subset thereof. In certain aspects, the "C1-C3 alkyl" group can be optionally further substituted. As a further example, a "C1-C4 alkyl" group can be selected from methyl, ethyl, n-propyl, i-propyl, cyclopropyl, n-butyl, i-butyl, s-butyl, t-butyl, and cyclobutyl, or from a subset thereof. In certain aspects, the "C1-C4 alkyl" group can be optionally further substituted. As a further example, a "C1-C6 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, and cyclohexane, or from a subset thereof. In certain aspects, the "C1-C6 alkyl" group can be optionally further substituted. As a further example, a "C1-C8 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, and cyclooctane, or from a subset thereof. In certain aspects, the "C1-C8 alkyl" group can be optionally further substituted. As a further example, a "C1-C12 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, cyclooctane, nonane, cyclononane, decane, cyclodecane, undecane, cycloundecane, dodecane, and cyclododecane, or from a subset thereof. In certain aspects, the "C1-C12 alkyl" group can be optionally further substituted.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, nitrile, sulfonamide, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or ($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halogen," "halide," and "halo," as used herein, refer to the halogens fluorine, chlorine, bromine, and iodine. It is also contemplated that, in various aspects, halogen can be selected from fluoro, chloro, bromo, and iodo. For example, halogen can be selected from fluoro, chloro, and bromo. As a further example, halogen can be selected from fluoro and chloro. As a further example, halogen can be selected from chloro and bromo. As a further example, halogen can be selected from bromo and iodo. As a further example, halogen can be selected from chloro, bromo, and iodo. In one aspect, halogen can be fluoro. In a further aspect, halogen can be chloro. In a still further aspect, halogen is bromo. In a yet further aspect, halogen is iodo.

It is also contemplated that, in certain aspects, pseudohalogens (e.g. triflate, mesylate, tosylate, brosylate, etc.) can be used in place of halogens. For example, in certain aspects, halogen can be replaced by pseudohalogen. As a further example, pseudohalogen can be selected from triflate, mesylate, tosylate, and brosylate. In one aspect, pseudohalogen is triflate. In a further aspect, pseudohalogen is mesylate. In a further aspect, pseudohalogen is tosylate. In a further aspect, pseudohalogen is brosylate.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —$O(CH_2)_{0-4}C(O)OR°$, —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$, —$SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; —$SiR°_3$; —$(C_{1-4}$ straight or branched)alkylene)O—$N(R°)_2$; or ($C_{1-4}$ straight or branched alkylene)C(O)O)—$N(R°)_2$, wherein each $R°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6 membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^•$, -(haloR$^•$), —$(CH_2)_{0-2}OH$, —$(CH_{12})_{0-2}OR^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR$^•$, or SSR$^•$ wherein each $R^•$ is unsubstituted or where preceded by "halo" is substituted only with one or more halogens, and is independently selected from $C_1$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_1$ aliphatic, CH$_2$Ph, O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono or bicyclic ring having 0-4 heteroatoms independently selected from nitrogen, oxygen, or sulfur.

Suitable substituents on the aliphatic group of R† are independently halogen, R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides including chloro, bromo, and iodo—and pseudohalides (sulfonate esters)—including triflate, mesylate, tosylate, and brosylate. It is also contemplated that a hydroxyl moiety can be converted into a leaving group via Mitsunobu reaction.

The terms "hydrolysable group" and "hydrolysable moiety" refer to a functional group capable of undergoing hydrolysis, e.g., under basic or acidic conditions. Examples of hydrolysable residues include, without limitatation, acid halides, activated carboxylic acids, and various protecting groups known in the art (see, for example, *Protective Groups in Organic Synthesis*, T. W. Greene, P. G. M. Wuts, Wiley-Interscience, 1999).

The term "protecting group" means a group which protects one or more functional groups of a compound giving rise to a protected derivative of the specified compound. Functional groups which may be protected include, by way of example, amino groups, hydroxyl groups, and the like. Protecting groups are well-known to those skilled in the art and are described, for example, in T. W. Greene and G. M. Wuts, *Protective Groups in Organic Synthesis*, Third Edition, Wiley, New York, 1999, and references cited therein.

The term "amino-protecting group" means a protecting group suitable for preventing undesired reactions at an amino group, include, but are not limited to, tert-butoxycarbonyl (BOC), trityl (Tr), benzyloxycarbonyl (Cbz), 9-fluorenyl-methoxycarbonyl (FMOC), formyl, trimethylsilyl (TMS), tert-butyldimethylsilyl (TBS), benzyl, p-methoxybenzyl, p-fluorobenzyl, p-chlorobenzyl, p-bromobenzyl, diphenylmethyl naphtylmethyl, tetrahydropyran (THP), and the like.

The term "hydroxyl-protecting group" means a protecting group suitable for preventing undesirable reactions at a hydroxyl group. Representative hydroxyl-protecting groups include, but are not limited to, sibyl groups including tri(1-6C)-alkylsilyl groups, such as trimethylsilyl (TMS), triethylsilyl (TES), tert-butyldimethylsilyl (TBS), and the like; esters (acyl groups) including (1-6C)-alkanoyl groups, such as formyl, acetyl, and the like; arylmethyl groups, such as benzyl (Bn), p-methoxybenzyl (PMB), 9-fluorenylmethyl (Fm), diphenylmethyl (benzhydryl, DPM), tetrahydropyran (THP), methoxylmethyl (MOM), methylthiomethyl (MTM), benzyloxymethyl (BOM), and the like.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

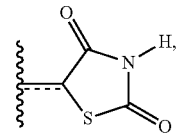

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, monosubstituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and/or (+) and (−) are employed to designate the sign of rotation of plane-polarized light by the compound, with (−) or/meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., *The Royal Society of Chemistry*, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

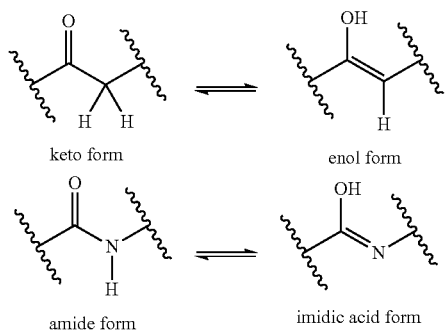

keto form    enol form amide form    imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

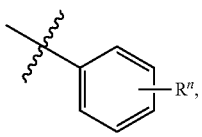

which is understood to be equivalent to a formula:

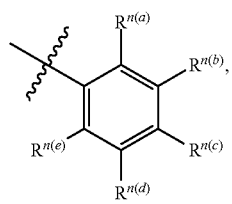

wherein n is typically an integer. That is, Rn is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Sigma-Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as *Fieser and Fieser's Reagents for Organic Synthesis*, Volumes 1-17 (John Wiley and Sons, 1991); *Rodd's Chemistry of Carbon Compounds*, Volumes 1-5 and Supplementals (Elsevier Science Publishers, 1989); *Organic Reactions*, Volumes 1-40 (John Wiley and Sons, 1991); March's *Advanced Organic Chemistry*, (John Wiley and Sons, 4th Edition); and Larock's *Comprehensive Organic Transformations* (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

II. COMPOUNDS

In one aspect, the invention relates to pyrimidinone compounds and/or oxypyrimidine compounds or pharmaceutically acceptable salts, hydrates, solvates, or polymorphs thereof. It is contemplated that each disclosed derivative can be optionally further substituted. It is also contemplated that any one or more derivative can be optionally omitted from the invention. It is understood that a disclosed compound can be provided by the disclosed preparation methods. It is also understood that the disclosed compounds can be employed in the disclosed methods of using.

A. Structure

In one aspect, the invention relates to using compounds of the formula:

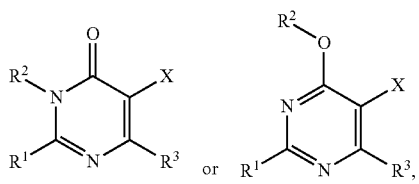

wherein X is selected from hydroxyl, fluoro, chloro, bromo, —OR$^7$, —NR$^{11}$R$^{12}$, —NR$^{11}$COR$^{12}$, —NR$^{11}$CO$_2$R$^{12}$, and —NR$^{11}$CONR$^{12}$R$^{13}$; wherein R$^1$ is optionally substituted and selected from aryl, heteroaryl, aryl-substituted alkyl, heteroaryl-substituted alkyl, —NR$^{11}$R$^{12}$, —NR$^{11}$COR$^{12}$, —NR$^{11}$CO$_2$R$^{12}$, —NR$^{11}$CONR$^{12}$R$^{13}$, —COR$^{11}$, —CONR$^{12}$R$^{13}$, and —OR$^7$; wherein R$^2$ is optionally substituted, where permitted, and selected from hydrogen, alkyl, heteroalkyl, cycloalkyl, heterocycloalkyl, aryl, and heteroaryl; or wherein R$^1$ and R$^2$ together form an optionally substituted ring with the carbon and nitrogen to which they are attached, selected from pyrrolidinyl, imidazolidinyl, hexahydropyrimidinyl, 1,3,5-triazinanyl, and piperidinyl;
wherein R$^3$ is optionally substituted and selected from cycloalkyl, heterocycloalkyl, aryl, heteroaryl, —NR$^{11}$R$^7$, —NR$^{11}$COR$^{12}$, —NR$^{11}$CO$_2$R$^7$, —NR$^{11}$CONR$^{12}$R$^{13}$, —NR$^{11}$SO$_2$R$^{12}$, —SO$_2$NR$^{12}$R$^{13}$, —CONR$^4$R$^5$, and —COR$^6$; wherein R$^4$ and R$^5$ are each optionally substituted where permitted and independently selected from hydrogen, alkyl, heteroalkyl, cycloalkyl, heterocycloalkyl, aryl, and heteroaryl; or wherein —NR$^4$R$^5$ together form an optionally substituted ring selected from piperidinyl, morpholinyl, and piperazinyl; wherein R$^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein R$^7$ is selected from alkyl, heteroalkyl, cycloalkyl, heterocycloalkyl, aryl, and heteroaryl; and wherein each of R$^{11}$, R$^{12}$, and R$^{13}$, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof.

In a further aspect, the invention relates to a compound of the formula:

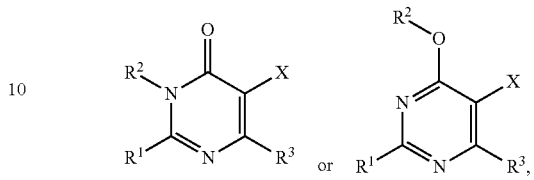

wherein X is selected from hydroxyl, fluoro, chloro, bromo, —OR$^7$, —NR$^{11}$R$^{12}$, —NR$^{11}$COR$^{12}$, —NR$^{11}$CO$_2$R$^{12}$, and —NR$^{11}$CONR$^{12}$R$^{13}$; wherein R$^1$ is optionally substituted and selected from aryl, heteroaryl, aryl-substituted alkyl, heteroaryl-substituted alkyl, —NR$^{11}$R$^{12}$, —NR$^{11}$COR$^{12}$, —NR$^{11}$CO$_2$R$^{12}$, —NR$^{11}$CONR$^{12}$R$^{13}$, —COR$^{11}$, —CONR$^{12}$R$^{13}$, and —OR$^7$; wherein R$^2$ is optionally substituted where permitted and selected from hydrogen, alkyl, heteroalkyl, cycloalkyl, heterocycloalkyl, aryl, and heteroaryl; or wherein R$^1$ and R$^2$ together form an optionally substituted ring with the carbon and nitrogen to which they are attached, selected from pyrrolidinyl, imidazolidinyl, hexahydropyrimidinyl, 1,3,5-triazinanyl, and piperidinyl;
wherein R$^3$ is optionally substituted and selected from cycloalkyl; heterocycloalkyl; aryl or heteroaryl, provided that R$^1$ and R$^2$ do not form a ring together with the carbon and nitrogen to which they are attached; —CONR$^4$R$^5$, and —COR$^6$; wherein R$^4$ and R$^5$ are each optionally substituted, where permitted, and independently selected from hydrogen, alkyl, heteroalkyl, cycloalkyl, heterocycloalkyl, aryl, and heteroaryl; wherein at least one of R$^4$ or R$^5$ is not hydrogen, and provided that when R$^1$ is an aryl or heteroaryl group having 6 or more ring members, then neither R$^3$ nor R$^4$ is hydrogen; or wherein —NR$^4$R$^5$ together form an optionally substituted ring selected from piperidinyl, morpholinyl, and piperazinyl; wherein R$^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein R$^7$ is selected from alkyl, heteroalkyl, cycloalkyl, heterocycloalkyl, aryl, and heteroaryl; and wherein each of R$^{11}$, R$^{12}$, and R$^{13}$, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof.

In a further aspect, the compound has the formula:

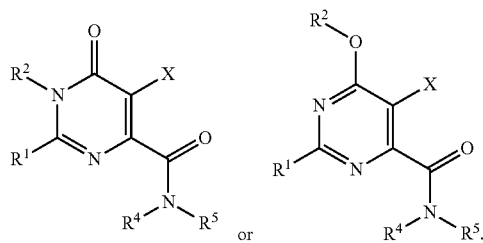

In a further aspect, the compound has the formula:

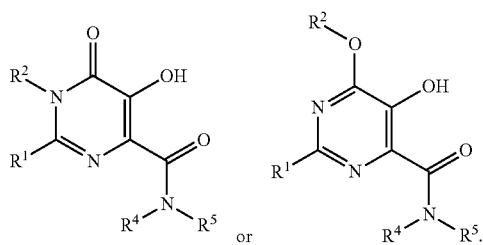

In a further aspect, the compound has the formula:

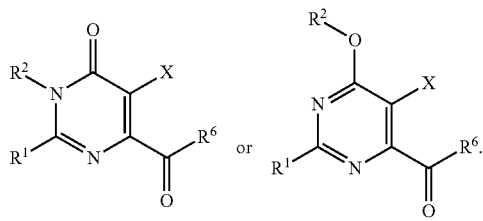

In a further aspect, the compound has the formula:

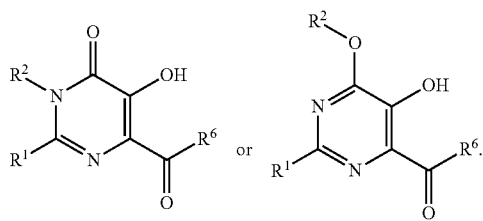

B. X Groups

In one aspect, X is selected from hydroxyl, fluoro, chloro, bromo, —$OR^7$, —$NR^{11}R^{12}$, —$NR^{11}COR^{12}$, —$NR^{11}CO_2R^{12}$, and —$NR^{11}CONR^{12}R^{13}$. In a further aspect, X is hydroxyl, and the compound has the formula:

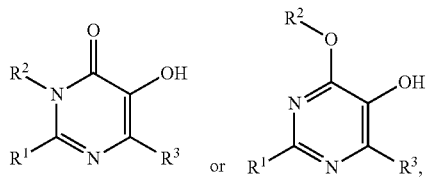

In a further aspect, X is halogen selected from fluoro, chloro, and bromo. In a further aspect, X is —$OR^7$. In a further aspect, X is selected from —$NR^{11}R^{12}$, —$NR^{11}COR^{12}$, —$NR^{11}CO_2R^{12}$, and —$NR^{11}CONR^{12}R^{13}$.

C. $R^1$ Groups

In one aspect, $R^1$ is optionally substituted and selected from aryl, heteroaryl, aryl-substituted alkyl, heteroaryl-substituted alkyl, —$NR^{11}R^{12}$, —$NR^{11}COR^{12}$, —$NR^{11}CO_2R^{12}$, —$NR^{11}CONR^{12}R^{13}$, —$COR^{11}$, —$CONR^{12}R^{13}$, and —$OR^7$. In a further aspect, $R^1$ is substituted with 0-3 groups. In a further aspect, $R^1$ is substituted with 1-2 groups. In various further aspects, the groups are independently selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl.

In a further aspect, $R^1$ is —$COR^{11}$. In a further aspect, $R^1$ is —$NR^{11}R^{12}$, —$NR^{11}COR^{12}$, —$NR^{11}CO_2R^{12}$, —$NR^{11}CONR^{12}R^{13}$, or —$NR^{11}CONR^{12}R^{13}$. In a further aspect, $R^1$ is —$NR^{11}R^{12}$. In a further aspect, $R^1$ is $NR^{11}COR^{12}$. In a further aspect, $R^1$ is $NR^{11}CO_2R^{12}$.

In a further aspect, $R^1$ is —$OR^7$. In a further aspect, $R^1$ is aryl. In a further aspect, $R^1$ is heteroaryl. In a further aspect, $R^1$ is aryl-substituted alkyl. In a further aspect, $R^1$ is heteroaryl-substituted alkyl.

D. $R^2$ Groups

In one aspect, $R^2$ is optionally substituted, where permitted, and selected from hydrogen, alkyl, heteroalkyl, cycloalkyl, heterocycloalkyl, aryl, and heteroaryl. In a further aspect, $R^2$ is substituted with 0-3 groups. In a further aspect, $R^2$ is substituted with 1-2 groups. In various further aspects, the groups are independently selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl.

In a further aspect, $R^2$ is hydrogen. In a further aspect, $R^2$ is alkyl. In a further aspect, $R^2$ is heteroalkyl. In a further aspect, $R^2$ is cycloalkyl. In a further aspect, $R^2$ is heterocycloalkyl. In a further aspect, $R^2$ is aryl. In a further aspect, $R^2$ is heteroaryl.

In one aspect, $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl.

E. $R^3$ Groups

In one aspect, $R^3$ is optionally substituted and selected from cycloalkyl, heterocycloalkyl, aryl, heteroaryl, —$NR^{11}R^7$, —$NR^{11}COR^{12}$, —$NR^{11}CO_2R^7$, —$NR^{11}CONR^{12}R^{13}$, —$NR^{11}SO_2R^{12}$, —$SO_2NR^{12}R^{13}$, —$CONR^4R^5$, and —$COR^6$. In a further aspect, wherein $R^3$ is optionally substituted and selected from cycloalkyl; heterocycloalkyl; aryl or heteroaryl, provided that $R^1$ and $R^2$ do not form a ring together with the carbon and nitrogen to which they are attached; —$CONR^4R^5$, and —$COR^6$.

In a further aspect, $R^3$ is optionally substituted and selected from cycloalkyl, heterocycloalkyl, aryl, and heteroaryl. In a further aspect, $R^3$ is cycloalkyl or heterocycloalkyl, and wherein $R^3$ is substituted with 0-3 groups. In various further aspects, the groups are independently selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl. In a further aspect, $R^3$ is cycloalkyl or heterocycloalkyl. In a further aspect, $R^3$ is cycloalkyl or heterocycloalkyl, and wherein $R^3$ is substituted with 1-2 groups. In a further aspect, $R^3$ is cycloalkyl selected from cyclopropyl, cyclobutyl, cyclopentyl, cyclohexyl, and bicyclo[3.1.0]hexyl.

In a further aspect, $R^3$ is heterocycloalkyl selected from oxirane, oxetane, tetrahydrofuran, tetrahydro-2H-pyran, oxepane, oxocane, dioxirane, dioxetane, dioxolane, dioxane, dioxepane, dioxocane, thiirane, thietane, tetrahydrothiophene, tetrahydro-2H-thiopyran, thiepane, thiocane, dithiirane, dithietane, dithiolane, dithiane, dithiepane, dithiocane, oxathiirane, oxathietane, oxathiolane, oxathiane, oxathiepane, oxathiocane, aziridine, azetidine, pyrrolidone, piperidine, azepane, azocane, diaziridine, diazetidine, imidazolidine, piperazine, diazepane, diazocane, hexahydropyrimidine, triazinane, oxaziridine, oxazetidine, oxazolidine, morpholine, oxazepane, oxazocane, thiaziridine, thiazetidine, thiazolidine, thiomorpholine, thiazepane, and thiazocane.

In a further aspect, $R^3$ is aryl or heteroaryl, and wherein $R^3$ is substituted with 0-3 groups. In a further aspect, $R^3$ is aryl or heteroaryl, and wherein $R^3$ is substituted with 1-2 groups. In various further aspects, the groups are independently selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl. In a further aspect, $R^3$ is aryl selected from phenyl and naphthyl. In a further aspect, $R^3$ is heteroaryl selected from oxazolyl, isoxazolyl, pyrazolyl, furanyl, pyranyl, imidazolyl, thiophenyl, pyridinyl, pyridazinyl, pyrimidinyl, pyrazinyl, triazinyl, tetrazinyl, benzofuranyl, benzothiophene, indolyl, indazolyl, quinolinyl, naphthyridinyl, benzothiazolyl, benzooxazolyl, benzoimidazolyl, and benzotriazolyl.

In a further aspect, $R^3$ is a five-membered heterocycle selected from:

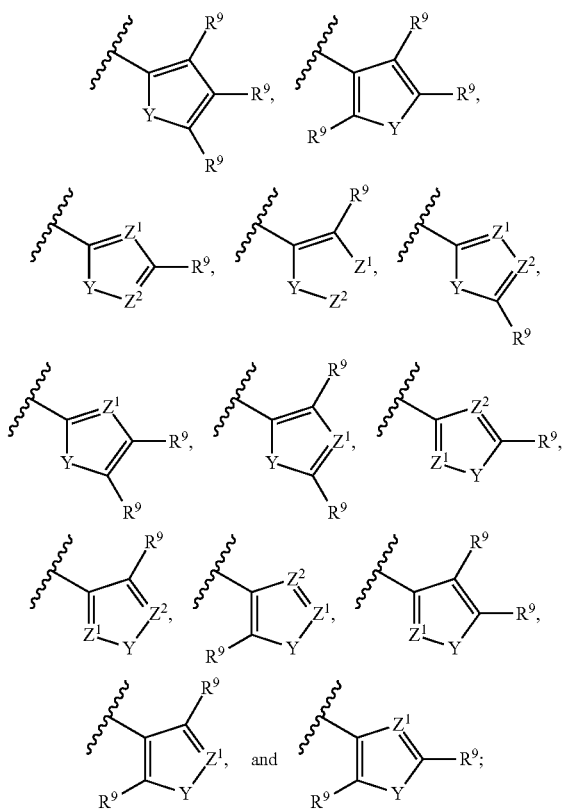

wherein Y is selected from O, S, and N—$R^8$; wherein $Z^1$ is selected from N and C—$R^9$; and wherein $Z^2$ is selected from N and C—$R^9$, wherein each $R^8$ is independently selected from hydrogen methyl ethyl, propyl, and butyl; and wherein each $R^9$ is independently selected from hydrogen, cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl.

In a further aspect, $R^3$ is a six-membered heterocycle selected from:

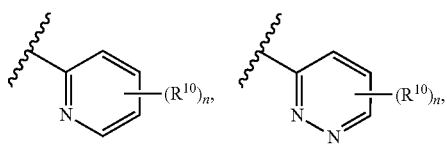

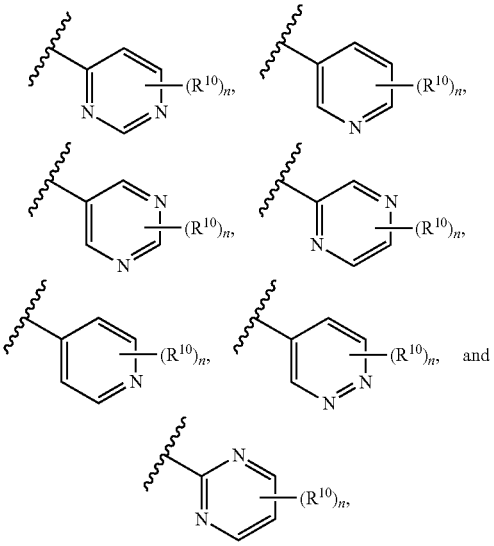

wherein n is an integer from 0-2; and wherein each $R^{10}$ is independently selected from hydrogen, cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl.

In a further aspect, $R^3$ is selected from —$NR^{11}R^7$, —$NR^{11}COR^{12}$, —$NR^{11}CO_2R^7$, and —$NR^{11}CONR^{12}R^{13}$. In a further aspect, $R^3$ is —$NR^{11}SO_2R^{12}$. In a further aspect, $R^3$ is —$SO_2NR^{12}R^{13}$. In a further aspect, $R^3$ is $CONR^4R^5$. In a further aspect, $R^3$ is $COR^6$.

F. $R^4$ Groups

In one aspect, $R^4$ is selected from hydrogen, alkyl, and heteroalkyl, cycloalkyl, heterocycloalkyl, aryl, and heteroaryl, and wherein $R^4$ is substituted with 0-3 groups, where permitted. In various further aspects, the groups are independently selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl. In a further aspect, $R^4$ is selected from hydrogen, alkyl, heteroalkyl, cycloalkyl, heterocycloalkyl, aryl, and heteroaryl, and wherein $R^4$ is substituted with 1-2 groups, where permitted. In a further aspect, $R^4$ is not hydrogen.

G. $R^5$ Groups

In one aspect, $R^5$ is selected from hydrogen, alkyl, heteroalkyl, cycloalkyl, heterocycloalkyl, aryl, and heteroaryl, and wherein $R^5$ is substituted with 0-3 groups, where permitted. In various further aspects, the groups are independently selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl. In a further aspect, $R^5$ is selected from hydrogen, alkyl, heteroalkyl, cycloalkyl, heterocycloalkyl, aryl, and heteroaryl, and wherein $R^5$ is substituted with 1-2 groups, where permitted. In a further aspect, $R^5$ is not hydrogen.

In one aspect, $R^4$ and $R^5$ are each optionally substituted, where permitted, and independently selected from hydrogen, alkyl, heteroalkyl, cycloalkyl, heterocycloalkyl, aryl, and heteroaryl; or wherein —$NR^4R^5$ together form an optionally substituted ring selected from piperidinyl, morpholinyl, and piperazinyl.

H. $R^6$ Groups

In one aspect, $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl. In a further aspect, $R^6$ is substituted with 0-3 groups. In a further aspect, $R^6$ is substituted with 1-2 groups. In various further aspects, the groups are independently selected from cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl.

In a further aspect, $R^6$ is phenyl. In a further aspect, phenyl is substituted with 1-2 groups.

In a further aspect, $R^6$ is alkyl selected from methyl, ethyl, propyl, butyl, pentyl, hexyl, heptyl, octyl, nonyl, decyl, undecyl, and dodecyl.

In a further aspect, $R^6$ is heteroalkyl selected from selected from residues of methyl, ethyl, propyl, butyl, pentyl, hexyl, heptyl, octyl, nonyl, decyl, undecyl, and dodecyl; wherein at least one carbon atom of the residue is replaced with a heteroatom selected from O, S, or $NR^{11}$; and wherein $R^{11}$ is selected from hydrogen, methyl, ethyl, and propyl.

In a further aspect, $R^6$ is cycloalkyl selected from cyclopropyl, cyclobutyl, cyclopentyl, cyclohexyl, cycloheptyl, cyclooctyl, cyclononyl, bicyclo[3.1.0]hexyl, bicyclo[4.1.0]heptyl, bicyclo[5.1.0]octyl, bicyclo[6.1.0]nonyl, bicyclo[3.2.0]heptyl, bicyclo[4.2.0]octyl, bicyclo[5.2.0]nonyl, bicyclo[3.3.0]octyl, bicyclo[4.3.0]nonyl, bicyclo[2.2.1]heptyl, bicyclo[3.2.1]octyl, bicyclo[4.2.1]nonyl, bicyclo[2.2.2]octyl, bicyclo[3.2.2]nonyl, and bicyclo[3.3.1]nonyl.

In a further aspect, $R^6$ is heterocycloalkyl selected from analogs of cyclopropyl, cyclobutyl, cyclopentyl, cyclohexyl, cycloheptyl, cyclooctyl, cyclononyl, bicyclo[3.1.0]hexyl, bicyclo[4.1.0]heptyl, bicyclo[5.1.0]octyl, bicyclo[6.1.0]nonyl, bicyclo[3.2.0]heptyl, bicyclo[4.2.0]octyl, bicyclo[5.2.0]nonyl, bicyclo[3.3.0]octyl, bicyclo[4.3.0]nonyl, bicyclo[2.2.1]heptyl, bicyclo[3.2.1]octyl, bicyclo[4.2.1]nonyl, bicyclo[2.2.2]octyl, bicyclo[3.2.2]nonyl, and bicyclo[3.3.1]nonyl, wherein one or more heteroatoms selected from O, S, and N—R replace 1, 2, or 3 carbon atoms in the cycle.

In a further aspect, $R^6$ is selected from pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl.

I. $R^7$ Groups

In one aspect, $R^7$ is selected from alkyl, heteroalkyl, cycloalkyl, heterocycloalkyl, aryl, and heteroaryl. For example, $R^7$ can be selected from one or more of alkyl, heteroalkyl, cycloalkyl, heterocycloalkyl, aryl, and heteroaryl.

J. $R^8$ Groups

In one aspect, each $R^8$ is independently selected from hydrogen methyl ethyl, propyl, and butyl. For example, each $R^8$ can be selected from one or more of hydrogen methyl ethyl, propyl, and butyl. In a further aspect, $R^8$ is not hydrogen.

K. $R^9$ Groups

In one aspect, each $R^9$ is independently selected from hydrogen, cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl. For example, each $R^9$ can be selected from one or more of hydrogen, cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl. In a further aspect, $R^9$ is not hydrogen.

L. $R^{10}$ Groups

In one aspect, each $R^{10}$ is independently selected from hydrogen, cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl. For example, each $R^{10}$ can be selected from one or more of hydrogen, cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl. In a further aspect, $R^{10}$ is not hydrogen.

M. $R^{11}$ Groups

In certain aspects, $R^{11}$, when present, is selected from alkyl, heteroalkyl, cycloalkyl, heterocycloalkyl, aryl, and heteroaryl.

N. $R^{12}$ Groups

In certain aspects, $R^{12}$, when present, is selected from alkyl, heteroalkyl, cycloalkyl, heterocycloalkyl, aryl, and heteroaryl.

O. $R^{13}$ Groups

In certain aspects, $R^{13}$, when present, is selected from alkyl, heteroalkyl, cycloalkyl, heterocycloalkyl, aryl, and heteroaryl.

III. PHARMACEUTICAL COMPOSITIONS

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

For example, in one aspect, the invention relates to a pharmaceutical composition comprising a pharmaceutically acceptable carrier and an effective amount of a compound of the formula:

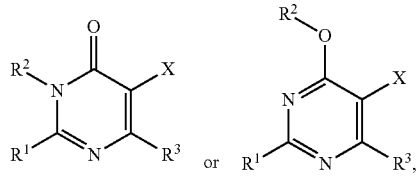

wherein X is selected from hydroxyl, fluoro, chloro, bromo, $-OR^7$, $-NR^{11}R^{12}$, $-NR^{11}COR^{12}$, $-NR^{11}CO_2R^{12}$, and $-NR^{11}CONR^{12}R^{13}$; wherein $R^1$ is optionally substituted and selected from aryl, heteroaryl, aryl-substituted alkyl, heteroaryl-substituted alkyl, $-NR^{11}R^{12}$, $-NR^{11}COR^{12}$, $-NR^{11}CO_2R^{12}$, $-NR^{11}CONR^{12}R^{13}$, $-COR^{11}$, $-CONR^{12}R^{13}$, and $-OR^7$; wherein $R^2$ is optionally substituted, where permitted, and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl; wherein $R^3$ is optionally substituted and selected from cycloalkyl, heterocycloalkyl, aryl, heteroaryl, $-NR^{11}R^7$, $-NR^{11}COR^{12}$, $-NR^{11}CO_2R^7$, $-NR^{11}CONR^{12}R^{13}$, $-NR^{11}SO_2R^{12}$, $-SO_2NR^{12}R^{13}$, $-CONR^4R^5$, and $-COR^6$; wherein $R^4$ and $R^5$ are each optionally substituted where permitted and independently selected from hydrogen, alkyl, heteroalkyl, cycloalkyl, heterocycloalkyl, aryl, and heteroaryl; or wherein $-NR^4R^5$ together form an optionally substituted ring selected from piperidinyl, morpholinyl, and piperazinyl; wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein $R^7$ is selected from alkyl, heteroalkyl, cycloalkyl, heterocycloalkyl, aryl, and heteroaryl; and wherein each of $R^{11}$, $R^{12}$, and $R^{13}$, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof.

In a further aspect, the effective amount is a therapeutically effective amount. In a further aspect, the effective amount is a prophylactically effective amount. In a further aspect, the composition further comprises one or more of: (a) an antiviral agent; (b) a M2 inhibition agent; (c) a neuraminidase inhibition agent; and/or (d) an agent known to treat flu symptoms, the agent selected from one or more of analgesic, decongestant, antihistamine, cough suppressant, and local anesthetic. In a further aspect, the composition further comprises one or more of Oseltamavir, Zanamivir, Amantadine, Rimantadine, Arbidol, Laninamivir, Peramivir, Vitamin D, and an interferon.

In a further aspect, the compound has the formula:

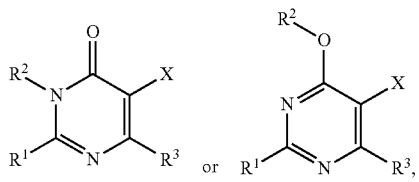

wherein X is selected from hydroxyl, fluoro, chloro, bromo, —$OR^7$, —$NR^{11}R^{12}$, —$NR^{11}COR^{12}$, —$NR^{11}CO_2R^{12}$, and —$NR^{11}CONR^{12}R^{13}$; wherein $R^1$ is optionally substituted and selected from aryl, heteroaryl, aryl-substituted alkyl, heteroaryl-substituted alkyl, —$NR^{11}R^{12}$, —$NR^{11}COR^{12}$, —$NR^{11}CO_2R^{12}$, —$NR^{11}CONR^{12}R^{13}$, —$COR^{11}$, —$CONR^{12}R^{13}$, and —$OR^7$; wherein $R^2$ is optionally substituted where permitted and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl; wherein $R^3$ is optionally substituted and selected from cycloalkyl; heterocycloalkyl; aryl or heteroaryl, provided that $R^1$ and $R^2$ do not form a ring together with the carbon and nitrogen to which they are attached; —$CONR^4R^5$, and —$COR^6$; wherein $R^4$ and $R^5$ are each optionally substituted, where permitted, and independently selected from hydrogen, alkyl, heteroalkyl, cycloalkyl, heterocycloalkyl, aryl, and heteroaryl; wherein at least one of $R^4$ or $R^5$ is not hydrogen, and provided that when $R^1$ is an aryl or heteroaryl group having 6 or more ring members, then neither $R^3$ nor $R^4$ is hydrogen; or wherein —$NR^4R^5$ together form an optionally substituted ring selected from piperidinyl, morpholinyl, and piperazinyl; wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein $R^7$ is selected from alkyl, heteroalkyl, cycloalkyl, heterocycloalkyl, aryl, and heteroaryl; and wherein each of $R^{11}$, $R^{12}$, and $R^{13}$, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require negative allosteric modulation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 miligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors.

Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating glutamate receptor activity (e.g., treatment of one or more neurological and/or psychiatric disorder associated with glutamate dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions. It is understood that the disclosed compositions can be prepared from the disclosed compounds. It is also understood that the disclosed compositions can be employed in the disclosed methods of using.

IV. METHODS OF USING THE COMPOUNDS AND COMPOSITIONS

The compounds disclosed herein are useful for treating, preventing, ameliorating, controlling or reducing the risk of influenza.

The disclosed compounds can be used as single agents or in combination with one or more other drugs in the treatment, prevention, control, amelioration or reduction of risk of the aforementioned diseases, disorders and conditions for which the disclosed compounds or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

The pharmaceutical compositions and methods of the present invention can further comprise other therapeutically active compounds as noted herein which are usually applied in the treatment of the above mentioned pathological conditions.

A. Preventing or Treating Influenza

In one aspect, the invention relates to a method for preventing or treating influenza in a subject, the method comprising: administering to the subject an effective amount of a compound of the formula:

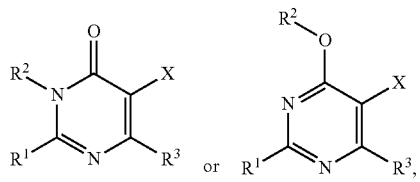

wherein X is selected from hydroxyl, fluoro, chloro, bromo, —$OR^7$, —$NR^{11}R^{12}$, —$NR^{11}COR^{12}$, —$NR^{11}CO_2R^{12}$, and —$NR^{11}CONR^{12}R^{13}$; wherein $R^1$ is optionally substituted and selected from aryl, heteroaryl, aryl-substituted alkyl, heteroaryl-substituted alkyl, —$NR^{11}R^{12}$, —$NR^{11}COR^{12}$, —$NR^{11}CO_2R^{12}$, —$NR^{11}CONR^{12}R^{13}$, —$COR^{11}$, —$CONR^{12}R^{13}$, and —$OR^7$; wherein $R^2$ is optionally substituted, where permitted, and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl; wherein $R^3$ is optionally substituted and selected from cycloalkyl, heterocycloalkyl, aryl, heteroaryl, —$NR^{11}R^7$, —$NR^{11}COR^{12}$, —$NR^{11}CO_2R^7$, —$NR^{11}CONR^{12}R^{13}$, —$NR^{11}SO_2R^{12}$, —$SO_2NR^{12}R^{13}$, —$CONR^4R^5$, and —$COR^6$; wherein $R^4$ and $R^5$ are each optionally substituted where permitted and independently selected from hydrogen, alkyl, heteroalkyl, cycloalkyl, heterocycloalkyl, aryl, and heteroaryl; or wherein —$NR^4R^5$ together form an optionally substituted ring selected from piperidinyl, morpholinyl, and piperazinyl; wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein $R^7$ is selected from alkyl, heteroalkyl, cycloalkyl, heterocycloalkyl, aryl, and heteroaryl; and wherein each of $R^{11}$, $R^{12}$, and $R^{13}$, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof, thereby preventing or treating the influenza.

In a further aspect, the subject is a mammal. In a further aspect, the mammal is a human. In a further aspect, the human is a patient. In a further aspect, the effective amount is a therapeutically effective amount. In a further aspect, the effective amount is a prophylactically effective amount. In a further aspect, the method further comprises the step of identifying the subject in need of treatment of influenza. In a further aspect, the subject has been diagnosed with a need for treatment of influenza prior to the administering step.

In a further aspect, the compound is an endonuclease inhibitor. In a further aspect, the compound is a RNA dependent RNA polymerase inhibitor.

In a further aspect, the influenza is Influenza A. In a further aspect, the influenza is Influenza B. In a further aspect, the influenza is H1N1, H2N2, H3N2, H5N1, or any combination of H1N1, H2N2, H3N2, and H5N1. In a further aspect, the influenza is drug resistant.

B. Inhibiting Development of Influenza Virus

In one aspect, the invention relates to a method for inhibiting development of influenza virus in a mammal, the method comprising: administering to the mammal an effective amount of at least one compound of the formula:

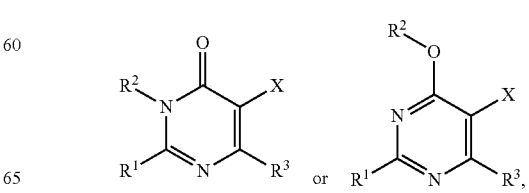

wherein X is selected from hydroxyl, fluoro, chloro, bromo, —$OR^7$, —$NR^{11}R^{12}$, —$NR^{11}COR^{12}$, —$NR^{11}CO_2R^{12}$, and —$NR^{11}CONR^{12}R^{13}$; wherein $R^1$ is optionally substituted and selected from aryl, heteroaryl, aryl-substituted alkyl, heteroaryl-substituted alkyl, —$NR^{11}R^{12}$, —$NR^{11}COR^{12}$, —$NR^{11}CO_2R^{12}$, —$NR^{11}CONR^{12}R^{13}$, —$COR^{11}$, —$CONR^{12}R^{13}$, and —$OR^7$; wherein $R^2$ is optionally substituted, where permitted, and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl; wherein $R^3$ is optionally substituted and selected from cycloalkyl, heterocycloalkyl, aryl, heteroaryl, —$NR^{11}R^7$, —$NR^{11}COR^{12}$, —$NR^{11}CO_2R^7$, —$NR^{11}CONR^{12}R^{13}$, —$NR^{11}SO_2R^{12}$, —$SO_2NR^{12}R^{13}$, —$CONR^4R^5$, and —$COR^6$; wherein $R^4$ and $R^5$ are each optionally substituted where permitted and independently selected from hydrogen, alkyl, heteroalkyl, cycloalkyl, heterocycloalkyl, aryl, and heteroaryl; or wherein —$NR^4R^5$ together form an optionally substituted ring selected from piperidinyl, morpholinyl, and piperazinyl; wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein $R^7$ is selected from alkyl, heteroalkyl, cycloalkyl, heterocycloalkyl, aryl, and heteroaryl; and wherein each of $R^{11}$, $R^{12}$, and $R^{13}$, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof, thereby inhibiting development of influenza virus in the mammal In a further aspect, inhibiting development of influenza virus in the mammal prevents influenza in the mammal. In a further aspect, inhibiting development of influenza virus in the mammal treats influenza in the mammal. In a further aspect, the method further comprises the step of identifying the mammal in need of inhibiting development of influenza virus. In a further aspect, the mammal has been diagnosed with a need for inhibiting development of influenza virus prior to the administering step.

C. Decreasing Influenza Virus Activity

In one aspect, the invention relates to a method for decreasing influenza virus activity in at least one cell, the method comprising contacting the cell with an effective amount of least one compound of the formula:

or

, wherein X is selected from hydroxyl, fluoro, chloro, bromo, —$OR^7$, —$NR^{11}R^{12}$, —$NR^{11}COR^{12}$, —$NR^{11}CO_2R^{12}$, and —$NR^{11}CONR^{12}R^{13}$; wherein $R^1$ is optionally substituted and selected from aryl, heteroaryl, aryl-substituted alkyl, heteroaryl-substituted alkyl, —$NR^{11}R^{12}$, —$NR^{11}COR^{12}$, —$NR^{11}CO_2R^{12}$, —$NR^{11}CONR^{12}R^{13}$, —$COR^{11}$, —$CONR^{12}R^{13}$, and —$OR^7$; wherein $R^2$ is optionally substituted, where permitted, and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl; wherein $R^3$ is optionally substituted and selected from cycloalkyl, heterocycloalkyl, aryl, heteroaryl, —$NR^{11}R^7$, —$NR^{11}COR^{12}$, —$NR^{11}CO_2R^7$, —$NR^{11}CONR^{12}R^{13}$, —$NR^{11}SO_2R^{12}$, —$SO_2NR^{12}R^{13}$, —$CONR^4R^5$, and —$COR^6$; wherein $R^4$ and $R^5$ are each optionally substituted where permitted and independently selected from hydrogen, alkyl, heteroalkyl, cycloalkyl, heterocycloalkyl, aryl, and heteroaryl; or wherein —$NR^4R^5$ together form an optionally substituted ring selected from piperidinyl, morpholinyl, and piperazinyl; wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein $R^7$ is selected from alkyl, heteroalkyl, cycloalkyl, heterocycloalkyl, aryl, and heteroaryl; and wherein each of $R^{11}$, $R^{12}$, and $R^{13}$, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof, thereby decreasing influenza virus activity in the cell.

In a further aspect, the cell is mammalian. In a further aspect, the cell is human. In a further aspect, contacting is via administration to a mammal. In a further aspect, the method further comprises the step of identifying a mammal in need of decreasing influenza virus activity in the cell. In a further aspect, a mammal has been diagnosed with a need for decreasing influenza virus activity prior to the administering step. In a further aspect, the need for decreasing influenza virus activity in the cell is associated with influenza in the mammal D. Decreasing Endonuclease Activity In one aspect, the invention relates to a method for decreasing endonuclease activity in at least one cell, the method comprising contacting the cell with an effective amount of least one compound of the formula:

or

, wherein X is selected from hydroxyl, fluoro, chloro, bromo, —$OR^7$, —$NR^{11}R^{12}$, —$NR^{11}COR^{12}$, —$NR^{11}CO_2R^{12}$, and —$NR^{11}CONR^{12}R^{13}$; wherein $R^1$ is optionally substituted and selected from aryl, heteroaryl, aryl-substituted alkyl, heteroaryl-substituted alkyl, —$NR^{11}R^{12}$, —$NR^{11}COR^{12}$, —$NR^{11}CO_2R^{12}$, —$NR^{11}CONR^{12}R^{13}$, —$COR^{11}$, —$CONR^{12}R^{13}$, and —$OR^7$; wherein $R^2$ is optionally substituted, where permitted, and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl; wherein $R^3$ is optionally substituted and selected from cycloalkyl, heterocycloalkyl, aryl, heteroaryl, —$NR^{11}R^7$, —NR¹¹COR¹², —NR¹¹CO₂R⁷, —NR¹¹CONR¹²R¹³, —NR¹¹SO₂R¹², —SO₂NR¹²R¹³, —CONR⁴R⁵, and —COR⁶; wherein R⁴ and R⁵ are each optionally substituted where permitted and independently selected from hydrogen, alkyl, heteroalkyl, cycloalkyl, heterocycloalkyl, aryl, and heteroaryl; or wherein —NR⁴R⁵ together form an optionally substituted ring selected from piperidinyl, morpholinyl, and piperazinyl; wherein R⁶ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein R⁷ is selected from alkyl, heteroalkyl, cycloalkyl, heterocycloalkyl, aryl, and heteroaryl; and wherein each of R¹¹, R¹², and R¹³, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof, thereby decreasing endonuclease activity in the cell.

In a further aspect, the cell is mammalian. In a further aspect, the cell is human. In a further aspect, contacting is via administration to a mammal. In a further aspect, the method further comprises the step of identifying a mammal in need of decreasing endonuclease activity in the cell. In a further aspect, a mammal has been diagnosed with a need for decreasing endonuclease activity prior to the administering step. In a further aspect, the need for decreasing endonuclease activity in the cell is associated with influenza in the mammal.

E. Decreasing Polymerase Activity

In one aspect, the invention relates to a method for decreasing polymerase activity in at least one cell, the method comprising contacting the cell with an effective amount of least one compound of the formula:

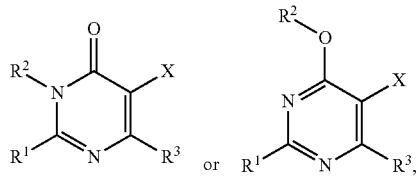

wherein X is selected from hydroxyl, fluoro, chloro, bromo, —OR⁷, —NR¹¹R¹², —NR¹¹COR¹², —NR¹¹CO₂R¹², and —NR¹¹CONR¹²R¹³; wherein R¹ is optionally substituted and selected from aryl, heteroaryl, aryl-substituted alkyl, heteroaryl-substituted alkyl, —NR¹¹R¹², —NR¹¹COR¹², —NR¹¹CO₂R¹², —NR¹¹CONR¹²R¹³, —COR¹¹, —CONR¹²R¹³, and —OR⁷; wherein R² is optionally substituted, where permitted, and selected from hydrogen, alkyl, heteroalkyl, cycloalkyl, heterocycloalkyl, aryl, and heteroaryl; or wherein R¹ and R² together form an optionally substituted ring with the carbon and nitrogen to which they are attached, selected from pyrrolidinyl, imidazolidinyl, hexahydropyrimidinyl, 1,3,5-triazinanyl, and piperidinyl; wherein R³ is optionally substituted and selected from cycloalkyl, heterocycloalkyl, aryl, heteroaryl, —NR¹¹R⁷, —NR¹¹COR¹², —NR¹¹CO₂R⁷, —NR¹¹CONR¹²R¹³, —NR¹¹SO₂R¹², —SO₂NR¹²R¹³, —CONR⁴R⁵, and —COR⁶; wherein R⁴ and R⁵ are each optionally substituted where permitted and independently selected from hydrogen, alkyl, heteroalkyl, cycloalkyl, heterocycloalkyl, aryl, and heteroaryl; or wherein —NR⁴R⁵ together form an optionally substituted ring selected from piperidinyl, morpholinyl, and piperazinyl; wherein R⁶ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein R⁷ is selected from alkyl, heteroalkyl, cycloalkyl, heterocycloalkyl, aryl, and heteroaryl; and wherein each of R¹¹, R¹², and R¹³, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof, thereby decreasing polymerase activity in the cell.

In a further aspect, the cell is mammalian. In a further aspect, the cell is human. In a further aspect, contacting is via administration to a mammal. In a further aspect, the method further comprises the step of identifying a mammal in need of decreasing polymerase activity in the cell. In a further aspect, a mammal has been diagnosed with a need for decreasing polymerase activity prior to the administering step. In a further aspect, the need for decreasing polymerase activity in the cell is associated with influenza in the mammal F. Co-Adminstration Methods In one aspect, the invention relates to a therapeutic method comprising co-administration of one or more treatments selected from Oseltamavir, Zanamivir, Amantadine, Rimantadine, Arbidol, Laninamivir, Peramivir, Vitamin D, and an interferon, with one or more compounds of the formula:

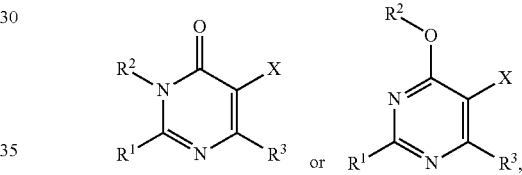

wherein X is selected from hydroxyl, fluoro, chloro, bromo, —OR⁷, —NR¹¹R¹², —NR¹¹COR¹², —NR¹¹CO₂R¹², and —NR¹¹CONR¹²R¹³; wherein R¹ is optionally substituted and selected from aryl, heteroaryl, aryl-substituted alkyl, heteroaryl-substituted alkyl, —NR¹¹R¹², —NR¹¹COR¹², —NR¹¹CO₂R¹², —NR¹¹CONR¹²R¹³, —COR¹¹, —CONR¹²R¹³, and —OR⁷; wherein R² is optionally substituted, where permitted, and selected from hydrogen, alkyl, heteroalkyl, cycloalkyl, heterocycloalkyl, aryl, and heteroaryl; or wherein R¹ and R² together form an optionally substituted ring with the carbon and nitrogen to which they are attached, selected from pyrrolidinyl, imidazolidinyl, hexahydropyrimidinyl, 1,3,5-triazinanyl, and piperidinyl; wherein R³ is optionally substituted and selected from cycloalkyl, heterocycloalkyl, aryl, heteroaryl, —NR¹¹R⁷, —NR¹¹COR¹², —NR¹¹CO₂R⁷, —NR¹¹CONR¹²R¹³, —NR¹¹SO₂R¹², —SO₂NR¹²R¹³, —CONR⁴R⁵, and —COR⁶; wherein R⁴ and R⁵ are each optionally substituted where permitted and independently selected from hydrogen, alkyl, heteroalkyl, cycloalkyl, heterocycloalkyl, aryl, and heteroaryl; or wherein —NR⁴R⁵ together form an optionally substituted ring selected from piperidinyl, morpholinyl, and piperazinyl; wherein R⁶ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein R⁷ is selected from alkyl, heteroalkyl, cycloalkyl, heterocycloalkyl, aryl, and heteroaryl; and wherein each of R¹¹, R¹², and R¹³, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof.

In a further aspect, the one or more treatments are administered before the one or more compounds. In a further aspect, the one or more compounds are administered before the one or more treatments. In a further aspect, the one or more treatments and the one or more compounds are administered substantially simultaneously. In a further aspect, the one or more treatments and the one or more compounds are each administered intermittently. In a further aspect, the one or more treatments and the one or more compounds are administered in a single pharmaceutical composition. In a further aspect, the one or more treatments are administered within a twenty-four hour period of administration of the one or more compounds.

In a further aspect, the one or more treatments is present in a therapeutically effective amount. In a further aspect, the one or more treatments is present in a prophylactically effective amount. In a further aspect, the one or more compounds is present in a therapeutically effective amount. In a further aspect, the one or more compounds is present in a prophylactically effective amount. In a further aspect, the one or more treatments and the one or more compounds are together present in a therapeutically effective amount. In a further aspect, the one or more treatments and the one or more compounds are together present in a prophylactically effective amount. In a further aspect, the one or more treatments and the one or more compounds are together present in a synergistically effective amount.

V. KITS

In one aspect, the invention relates to a kit comprising at least one compound of the formula:

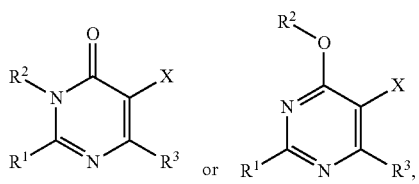

wherein X is selected from hydroxyl, fluoro, chloro, bromo, —$OR^7$, —$NR^{11}R^{12}$, —$NR^{11}COR^{12}$, —$NR^{11}CO_2R^{12}$, and —$NR^{11}CONR^{12}R^{13}$; wherein $R^1$ is optionally substituted and selected from aryl, heteroaryl, aryl-substituted alkyl, heteroaryl-substituted alkyl, —$NR^{11}R^{12}$, —$NR^{11}COR^{12}$, —$NR^{11}CO_2R^{12}$, —$NR^{11}CONR^{12}R^{13}$, —$COR^{11}$, —$CONR^{12}R^{13}$, and —$OR^7$; wherein $R^2$ is optionally substituted, where permitted, and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl; wherein $R^3$ is optionally substituted and selected from cycloalkyl, heterocycloalkyl, aryl, heteroaryl, —$NR^{11}R^7$, —$NR^{11}COR^{12}$, —$NR^{11}CO_2R^7$, —$NR^{11}CONR^{12}R^{13}$, —$NR^{11}SO_2R^{12}$, —$SO_2NR^{12}R^{13}$, —$CONR^4R^5$, and —$COR^6$; wherein $R^4$ and $R^5$ are each optionally substituted where permitted and independently selected from hydrogen, alkyl, heteroalkyl, cycloalkyl, heterocycloalkyl, aryl, and heteroaryl; or wherein —$NR^4R^5$ together form an optionally substituted ring selected from piperidinyl, morpholinyl, and piperazinyl; wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, isoxazolyl, and oxazolyl; wherein $R^7$ is selected from alkyl, heteroalkyl, cycloalkyl, heterocycloalkyl, aryl, and heteroaryl; and wherein each of $R^{11}$, $R^{12}$, and $R^{13}$, when present, is independently selected from hydrogen, alkyl, heteroalkyl, cycloalkyl, heterocycloalkyl, aryl, and heteroaryl;

or a pharmaceutically acceptable salt, hydrate, solvate, or polymorph thereof, and one or more of: (a) an antiviral agent; (b) a M2 inhibition agent; (c) a neuraminidase inhibition agent; (d) an agent known to treat flu symptoms; and/or (e) instructions for treating influenza.

In a further aspect, the antiviral agent is Arbidol. In a further aspect, the M2 inhibition agent is selected from Amantadine and Rimantadine. In a further aspect, the neuraminidase inhibition agent is selected from Zanamivir, Oseltamavir, Peramivir, and Laninamivir.

In a further aspect, the kit further comprises Vitamin D. In a further aspect, the kit further comprises an interferon. In a further aspect, the agent known to treat flu symptoms is selected from one or more of analgesic, decongestant, antihistamine, cough suppressant, and local anesthetic. In a further aspect, the compound and the at least one agent are co-formulated. In a further aspect, the compound and the at least one agent are co-packaged.

VI. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. General Methods

All chemicals (reagents and solvents) used as purchased from commercial suppliers. Parallel synthesis is accomplished with MiniBlock XT synthesizers obtained from Mettler Toledo AutoChem, accompanied by a stirring hotplate. Intermediate preparation is carried out with dried glassware, or in parallel using a 6-position MiniBlock XT synthesizer. A Thomson 2 mL 96 well filter plate (25 microns) used in plate filtrations is packed with approximately 50 mg of Celite 545 filter aid in each well. All automated weighing is done on a Bohdan Balance Automator (Mettler Toledo AutoChem), and parallel evaporations are performed on a GeneVac HT-24 system.

$^1$H NMR spectra are recorded on a Bruker-400 (400 MHz) spectrometer. Chemical shifts are reported as parts per million (ppm) and are referenced by the corresponding solvent peak. Data is reported as: chemical shift, multiplicity, coupling constants, and integration. Pre-purification and QC analysis is done on a Waters Acquity UPLC/PDA/ELSD/MS system carried out with a BEH C18 2.1×50 mm column using gradient elution. Water/acetonitrile/0.1% formic acid or 10 mM ammonium bicarbonate/acetonitrile is used for mobile phase depending on compound resolution and polarity.

Methanol with 4% Tetrahydrofuran is substituted for the acetonitrile when demanded by availability. Library purification is done either on a Berger Supercritical Fluid Chromatography (SFC) prep system utilizing a cyano 21×150 mm column and a gradient elution of 5-25% methanol at a rate of 2%/min at 50 mL/min; or a Dionex mass directed HPLC Purification System using a Phenomenex Gemini Aixia packed C18 30×50 mm, 5 μm column. Gradient methods and mobile phases are adjusted based on the pre-purification results.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

B. Synthetic Methods

1. Intermediate Preparation of 4,5-dihydroxypyrimidines

Dimethyl acetylenedicarboxylate (DMAD, 1 mL, 1 equiv.) is added to a stirred solution of 2-substituted amidoxime (8.16 mmol) in chloroform (0.335M) and maintained at 60° C. for 75 minutes to 4 hours as determined by TLC or UPLC. Upon cooling and evaporation of the solvent, the crude mixture is charged with xylenes (0.335M) and heated to 140° C. for 8 hours more before cooling slowly to rt. The resulting heavy precipitate is collected, washed with ethyl ether, then dried under vacuum to afford desired 4,5-dihydroxypyrimidine methyl esters in yields ranging from 15-50%. Spectral comparison to referenced compounds confirmed desired starting intermediates. 63 4,5-dihydroxypyrimidines analogs has been prepared to date using this methodology, including these two examples.

2. Methyl 5,6-dihydroxy-2-(pyridin-2-yl)pyrimidine-4-carboxylate

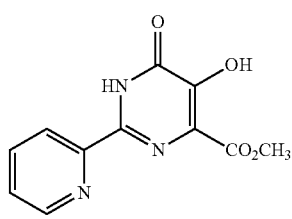 [SMILES: COC(=O)c1nc(-c2ccccn2)[nH]c(=O)c1O]

Avg. Purity (TWC & ELSD): 100%. $^1$H NMR (400 MHz, DMSO-d6) δ 12.84-12.41 (br s, 1H), 10.97-10.62 (br s, 1H), 8.70 (dd, J=4.0, 0.8 Hz, 1H), 8.21 (d, J=7.9 Hz, 1H), 8.01 (dt, J=7.8, 1.7 Hz, 1H), 7.58 (ddd, J=7.5, 4.8, 1.1 Hz, 1H), 3.87 (s, 3H). $^{13}$C NMR (101 MHz, DMSO-d6) δ 165.65, 158.44, 148.83, 148.44, 147.12, 143.94, 137.80, 125.74, 121.51, 52.29.

3. Methyl 5-hydroxy-2-(1-methyl-1H-imidazol-4-yl)-6-oxo-1,6-dihydropyrimidine-4-carboxylate

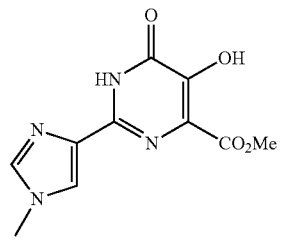 [SMILES: COC(=O)c1nc(-c2cn(C)cn2)[nH]c(=O)c1O]

$^1$H NMR (400 MHz, DMSO) δ 7.84 (s, 1H), 7.77 (s, 1H), 3.84 (s, 2H), 3.72 (s, 3H).

4. Intermediate Preparation of 2,5,6-trisubstutued-4-hydroxypyrimidines

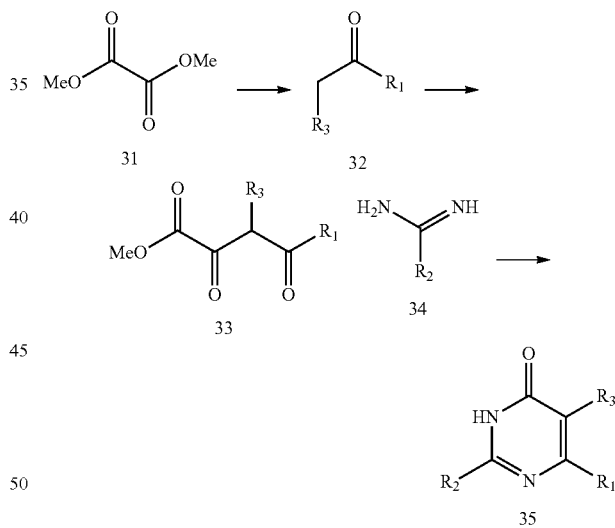

To 1.1 equivalents of sodium hydride (30.5 mmol, 1.1 equivalents, 60% in oil) in 55 mL of 10:1 ethyl ether (or tetrahydrofuran):ethanol is added to methyl formate (30.5 mmol, 1.1 equivalents). The mixture is stirred vigorously and cooled by ice bath before 32 (27.4 mmol, 1 equivalent, added as a 2M stock solution in ethyl ether) is added dropwise. Once addition is complete, the solution is refluxed for 4 hours. Once complete, appropriate amidine 34 is added, followed by ethanol (55 mL) and the remaining ethyl ether is evaporated off in vacuo. An additional 25 mL of ethanol is added, followed by 3 equivalents of DBU (1,8-diazobicyclo[5,4,0]-undec-7-ene) and the mixture is heated to 60° C. and maintained for 12 hours. The resulting mixture is diluted with ethyl acetate and water, extracted twice with ethyl acetate, with the organic layers combined, then washed with brine, dried, and concentrated again in vacuo. Product is purified by crystallization, or by flash chromatography. Typical yields ranged from 20-70% overall.

5. Ethyl 5-fluoro-6-oxo-2-(pyridin-2-yl)-1,6-dihydropyrimidine-4-carboxylate

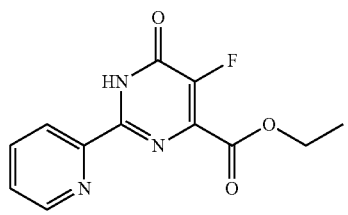 [SMILES: CCOC(=O)c1nc(-c2ccccn2)[nH]c(=O)c1F]

$^1$H NMR (400 MHz, CDCl$_3$) δ 11.40 (s, 1H), 8.59 (d, J=4.7 Hz, 1H), 8.44 (dd, J=7.9, 0.8 Hz, 1H), 7.87 (dd, J=11.0, 4.6 Hz, 1H), 7.48-7.43 (m, 1H), 4.43 (q, J=7.1 Hz, 2H), 1.38 (t, J=7.1 Hz, 3H). $^{13}$C NMR (101 MHz, CDCl$_3$) δ 162.20, 151.88, 149.14, 148.92, 148.79, 146.54, 137.80, 137.19, 126.79, 122.40, 62.53, 14.06.

6. Intermediate Preparation of 6-amino-5-hydroxy-2-substituted pyrimidin-4(3H)-one

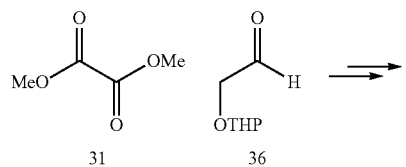

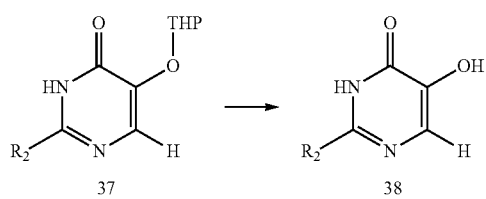

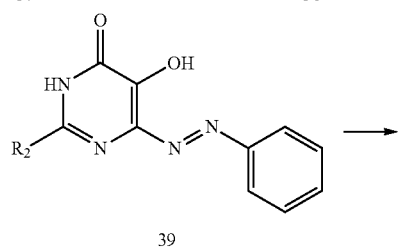

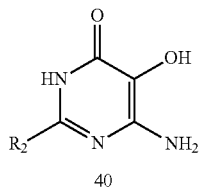

Preparation of 37 followed procedures described above for the preparation of 2,5,6-trisubstutued-4-hydroxypyrimidines, with the exception that 32 is any protected alpha-hydroxy acetaldehyde (i.e. THP protected 36). Deprotection of 37 involves dissolving 37 (5.85 mmol) in hot methanol (1M) and adding catalytic amount of toluenesulphonic acid to the homogeneous mixture. The mixture is stirred overnight at room temperature, analyzed to determine complete, then concentrated in vacuo, with solid collected by filtrate using ethyl acetate to wash to afford 38 in quantitative yield. For conversion to 39, a separate reaction vessel is established containing aniline (5.85 mmol) in water (3.8 mL) and concentrated HCl (1.9 mL) cooled in an ice bath and stirred vigorously. Sodium nitrite as a 2M solution in water (2.92 mL, 1 equivalent) is added, followed by 3 equivalents of sodium acetate (262 mg) which is added very slowly to the mixture with continuous stirring. Once addition is complete, the intermediate 38 (5.85 mmol) dissolved in 10% NaOH (4.84 mL) is added, and stirring continues at 0° C. for an hour, then warmed to room temperature. The mixture is diluted with water, and the precipitate filtered and the solids washed with more water, then dried in in vacuo to afford 39 as a blood red solid. To intermediate 39 in water at 70° C. is added in small portions sodium dithionite until a noticeable color change resulted (usually dark to yellowish). Sample is stirred at 70° C. with additional sodium dithionite added if dark color returned to mixture. Once yellowish color stabilizes for 30 minutes, the mixture is cooled in an ice bath, resulting in a precipitate. The precipitate is filtered, washing with water then dried to afford product 40 in reasonable purity (generally >75%) and yield (50-80%).

7. 6-amino-2-(pyridin-2-yl)pyrimidine-4,5-diol

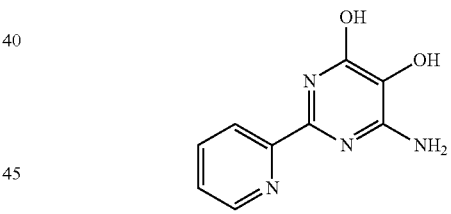

Avg. Purity (TWC & ELSD): 100%. $^1$H NMR (400 MHz, DMSO) δ 11.39 (br s, 1H), 8.72 (d, J=4.5 Hz, 1H), 8.68-8.41 (br s, 1H), 8.21 (d, J=7.9 Hz, 1H), 8.05 (td, J=7.8, 1.6 Hz, 1H), 7.65-7.56 (m, 1H), 5.98 (br s, 2H).

8. Intermediate Preparation of 2,6-disubstutued-5-(benzyloxy)-pyrimidin-4(3H)-one

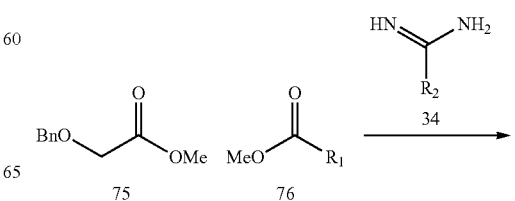

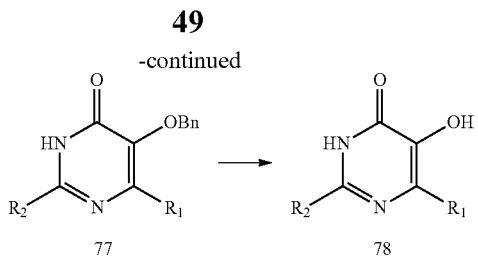

To a mixture of methyl 2-(benzyloxy)acetate 75 and ester (i.e., 76) in tetrahydrofuran (0.25M, THF) at 0° C. under a nitrogen atmosphere is added drop-wise 1.1 equivalents of 1M lithium bis(trimethylsilyl)amide in THF (tetrahydrofuran). Upon completion of the addition, the mixture is maintained at 0° C. for at least 3 hours, then allowed to warm slowly to room temperature. The reaction is then followed by HPLC. Once deemed complete, the crude product is quenched with methanol, and concentrated in vacuo. The crude product can be purified by chromatography or used directly in the cyclization step. To the crude product dissolved in methanol (0.25M), appropriate amidine 34 is added, followed by 4 to 5 equivalents of DBU (1,8-diazobicyclo[5,4,0]-undec-7-ene). The mixture is then placed under a nitrogen atmosphere, and maintained within a temperature range of 50 to 60° C. The reaction is then followed by HPLC until the starting adduct has been consumed. The mixture is then concentrated and purified by chromatography to afford 77 (and similar analogs), including the following four examples. Further, deprotection of 77 can be accomplished to produce compounds of type 78. Deprotection of 77 is done via typical hydrogenation conditions using a suitable catalyst, e.g., 10% Palladium on carbon, under a hydrogen atmosphere for 1-2 hours. Alternatively, 77 can be subjected to 1 to 33% hydrogen bromide in acetic acid (0.2M) for 1 to 2 hours. Deprotection is followed with final purification by HPLC to yield the desired final compound 78 in both cases. Typical yields ranged from 20-60% overall.

9. 2-amino-5-(benzyloxy)-3-methyl-6-(5-methyl-isoxazol-3-yl)pyrimidin-4(3H)-one

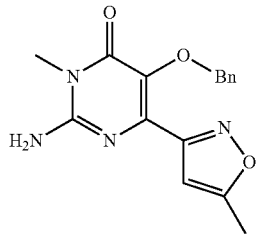

$^1$H NMR (400 MHz, DMSO) δ 7.47-7.39 (m, 2H), 7.39-7.26 (m, 3H), 7.09 (br s, 2H), 6.43 (d, J=1.1 Hz, 1H), 4.92 (s, 2H), 3.34 (s, 3H), 2.43 (d, J=0.9 Hz, 3H).

10. 5-(benzyloxy)-2-(methylamino)-6-(5-methyl-isoxazol-3-yl)pyrimidin-4-ol

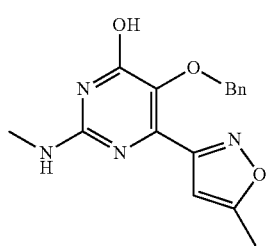 [SMILES: CNc1nc(O)c(OCc2ccccc2)c(-c2cc(C)on2)n1]

$^1$H NMR (400 MHz, DMSO) δ 11.47 (s, 1H), 7.46-7.38 (m, 2H), 7.38-7.26 (m, 4H), 6.47 (s, 1H), 4.95 (s, 2H), 2.79 (d, J=4.7 Hz, 3H), 2.44 (d, J=0.9 Hz, 3H).

11. 5-(benzyloxy)-6-((benzyloxy)methyl)-2-(methylamino)pyrimidin-4-ol

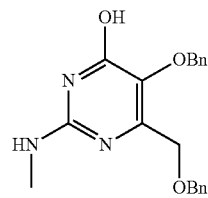 [SMILES: CNc1nc(O)c(OCc2ccccc2)c(COCc2ccccc2)n1]

$^1$H NMR (400 MHz, DMSO) δ 11.25 (br s, 1H), 7.33 (m, 10H), 6.28 (br s, 1H), 4.88 (s, 2H), 4.45 (s, 2H), 4.18 (s, 2H), 2.76 (s, 3H).

12. 3-(5,6-dihydroxy-2-(5-methylpyrazin-2-yl)pyrimidin-4-yl)-1,2,4-oxadiazol-5(4H)-one $^1$H NMR (400 MHz, DMSO) δ 13.02 (brs, 1H), 12.64 (s, 1H), 9.74 (d, J=1.4 Hz, 1H), 8.64 (d, J=1.4 Hz, 1H), 2.61 (s, 3H).

13. General Preparation of 3-hydroxy-4-oxo-4,6,7,8-tetrahydropyrrolo[1,2-a]pyrimidine-2-carboxylester

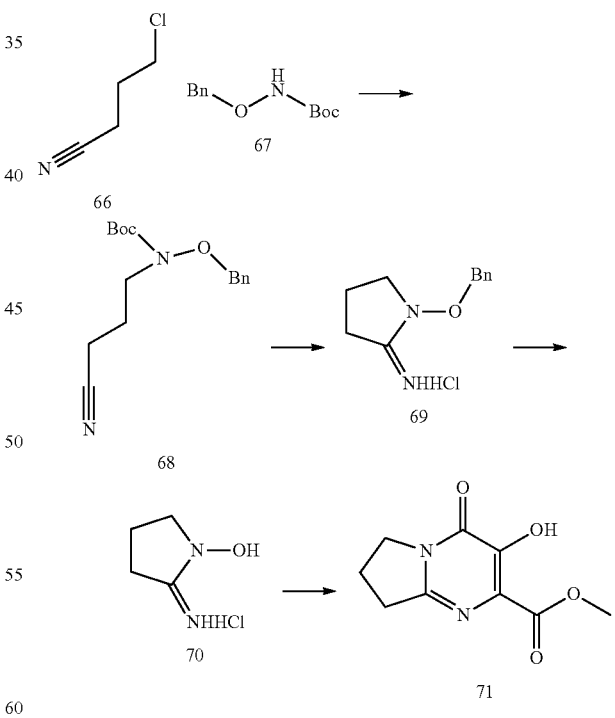

See: *J. Med. Chem.* 2008, 51, 861-874, incorporated herein by reference. To carbamate 67 (42.5 mmol, 1 equivalent) in DMF (0.4M) under nitrogen atmosphere at rt is added the unwashed sodium hydride slowly (2.2 g in oil, 1.3 equivalents, added in about 3 equal portions) then stirred for 10 minutes. Bubbling and foaming result, with a milky white mixture resulting. Sodium iodide (213 mmol, 5 equivalents) followed by the nitrile 66 (42.5 mmol, 1 equivalent) is added and the mixture is maintained at 80° C. for 6 hours, then cooled, followed by quenching any remaining sodium hydride with water dropwise. Extracted out product with ethyl acetate thrice, combined organic layers, dried and concentrated in vacuo. Flash chromatographed using a gradient method (10-30% EtOAc in Hexanes) is used to produce pure product 68 in quantitative yield (42.5 mmol). Nitrile 68 is suspended in approximately 145 mL of 4M HCl in dioxane and stirred at rt for 3 hours until deemed complete, then concentrated in vacuo to afford a solid precipitate, which is further washed with ethyl ether to produce clean cyclized product 69. Product 69 is redissolved in methanol and subjected to hydrogenation conditions (1 g of 10% Pd on charcoal, under a hydrogen atmosphere at atmospheric pressure) for 6 hours. The catalyst is filtered off through celite, and the filtrate concentrated. The resulting solid is washed with Et2O and collected to afford almost quantitative product 70 (42.4 mmol). Dimethyl acetyenedicarboxylate (1 equivalent) is added to a stirred solution of prepared amidoxime 70 (42.4 mmol) in chloroform (0.335M) containing 1.5 equivalents of triethylamine and maintained at reflux for 75 minutes to 4 hours until deemed complete. Note, temperature variations are dependent on amidoxime (i.e 6 membered cyclic amidoxime requires temperature modification). Upon cooling and evaporation of the solvent, the crude mixture is charged with xylenes (0.335M) and heated to 140° C. for 8 hours more before cooling slowly to rt. The resulting heavy precipitate is collected, washed with ethyl ether, then dried under vacuum to afford desired 1,2-cyclic-5,6-dihydroxypyrimidines-4-carboxyester (i.e 71) in yields ranging from 30-70%. Spectral comparison to referenced compounds confirmed desired starting intermediates given by this procedure.

14. Methyl 3-hydroxy-4-oxo-4,6,7,8-tetrahydropyrro[1,2-a]pyrimidine-2-carboxylate

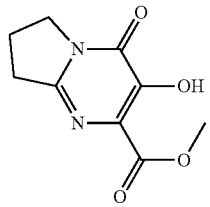

Avg. Purity (TWC & ELSD): 79.2%. $^1$H NMR (400 MHz, CDCl$_3$) δ 4.11 (dd, J=7.9, 6.8 Hz, 2H), 3.96 (s, 3H), 3.04 (t, J=8.0 Hz, 2H), 2.27-2.16 (m, 2H).

15. Methyl 3-hydroxy-4-oxo-4,6-dihydropyrido[2',3':3,4]pyrrolo[1,2-a]pyrimidine-2-carboxylate

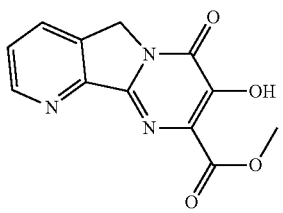 [SMILES: COC(=O)c1nc2n(c(=O)c1O)Cc1cccnc1-2]

$^1$H NMR (400 MHz, DMSO) δ 10.78 (s, 1H), 8.79 (d, J=3.7 Hz, 1H), 8.19 (d, J=7.0 Hz, 1H), 7.63 (dd, J=7.7, 4.7 Hz, 1H), 5.13 (s, 2H), 3.90 (s, 3H). $^{13}$C NMR (101 MHz, DMSO) δ 166.28, 156.70, 150.77, 149.59, 147.47, 145.52, 135.02, 132.57, 129.09, 125.20, 52.36, 48.16.

16. Preparation of 3-hydroxy-4-oxo-6,7,8,9-tetrahydro-4H-pyrido[1,2-a]pyrimidine-2-carboxylester

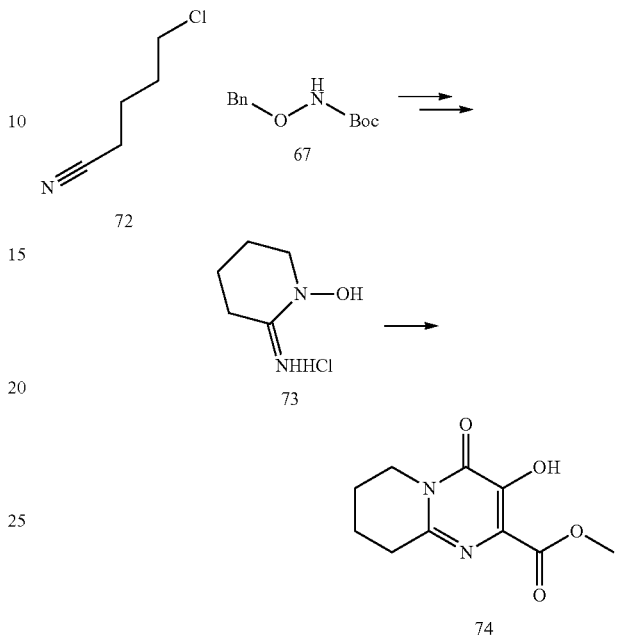

Preparation of 6-membered amidoxime 73 (and similar analogs) is similar to described above, with the exception being a one carbon longer starting nitrile, 72. To cyclicalkylamidoxime 73 (1 equivalent) in chloroform (0.335M) is added triethylamine (1.5 equivalents) at room temperature and stirred for about 10 minutes. The mixture then is cooled to −40° C. Then, dimethyl acetyenedicarboxylate (1 equivalent) is added dropwise, followed by the mixture being allowed to warm slowly to 0° C. over about 2 hours, then warmed slowly to room temperature over 30 minutes and maintained for another 60 minutes before removing and concentrating down in vacuo with no heat. Total reaction time is 4 hours before being concentrated, and flash chromatographed by gradient method (10-90% ethyl acetate in hexanes). The intermediate product is diluted with xylenes (0.335M) and the reaction is heated to 145° C. and monitored by UPLC till completion. Concentrated down to half the volume, then diluted with ethyl ether and filter off precipitates, washing solids with ethyl ether and allowing them to dry. Spectral comparison to referenced compounds confirmed desired starting intermediates given by this procedure.

17. General Intermediate Preparation of methyl 5-(protected oxy)-1,2-disubstituted-6-oxo-1,6-dihydropyrimidine-4-carboxylate

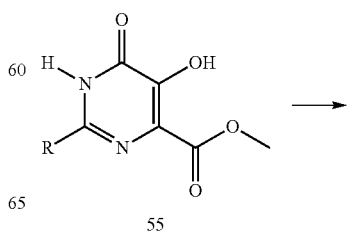

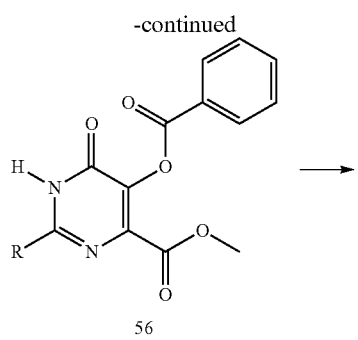

56

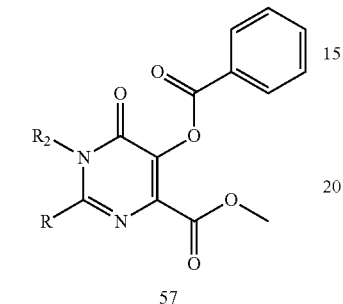

57

See: Bioorganic & Medicinal Chemistry Letters 20 (2010) 3275-3279 and references within (specifically Summa), incorporated by reference herein. To ester 55 (1 equivalent) in pyridine (0.3M) is added benzoic anhydride (1.2 equivalents) under a nitrogen atmosphere. The heavy suspension is heated to 60° C. and maintained for 3 hours before being concentrated until dryness. The product is suspended in dichloromethane, sonicated for about 5 minutes, then collected by filtration to afford 56 in pure form (two crops gives near quantitatvive yield). 56 can be produced directly with other protecting groups (THP, Benzyl for example) using the general procedure for Preparation of 2,5,6-trisubstutued-4-hydroxypyrimidines. To product 56 is added cesium carbonate (2 equivalents) and flushed with nitrogen. Anhydrous tetrahydrofuran (0.3M) is added, the mixture is stirred for 10 minutes, then the alkyl halide (2-3 equivalents) is added very slowly before the mixture then is heated to reflux and maintained for 12-18 hours before being allowed to cool and concentrated under vacuum. Crude product is purified by flash chromatography, with the slower eluting N-alkyl product 58 coming before the faster O-alkylated product. Typical ratios of N-versus O-alkylated product ranged from 3:1 to 6:1 respectively, and products are verified in comparison to published references to similar and identical products. N-alkylated yields ranged from 15-45% yield from 56 to 57.

18. Methyl 5-(benzoyloxy)-2-(4-fluorophenyl)-6-methoxypyrimidine-4-carboxylate

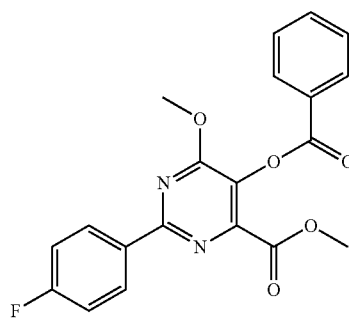

Avg. Purity (TWC & ELSD): 96.4%. $^1$H NMR (400 MHz, CDCl$_3$) δ 8.45-8.33 (m, 2H), 8.18-8.09 (m, 2H), 7.58 (dd, J=10.6, 4.3 Hz, 1H), 7.45 (t, J=7.7 Hz, 2H), 7.07 (t, J=8.7 Hz, 2H), 4.06 (s, 3H), 3.80 (s, 3H). $^{13}$C NMR (101 MHz, CDCl$_3$) δ 166.13, 163.83, 163.71, 163.42, 160.02, 147.34, 134.08, 132.55, 131.88, 130.76, 130.68, 130.51, 128.74, 128.30, 115.60, 115.39, 58.56, 54.89, 53.06.

19. Methyl 5-(benzoyloxy)-2-(4-fluorophenyl)-1-methyl-6-oxo-1,6-dihydropyrimidine-4-carboxylate

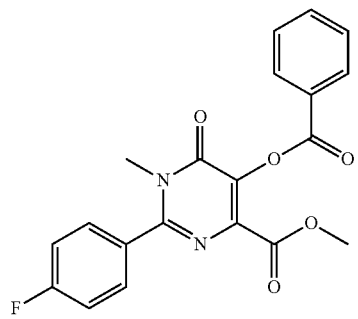 [SMILES: COC(=O)c1nc(-c2ccc(F)cc2)n(C)c(=O)c1OC(=O)c1ccccc1]

Avg. Purity (TWC & ELSD): 98.9%. $^1$H NMR (400 MHz, CDCl$_3$) δ 8.45-8.33 (m, 2H), 8.18-8.09 (m, 2H), 7.58 (dd, J=10.6, 4.3 Hz, 1H), 7.45 (t, J=7.7 Hz, 2H), 7.07 (t, J=8.7 Hz, 2H), 4.06 (s, 3H), 3.80 (s, 3H). $^{13}$C NMR (101 MHz, CDCl$_3$) δ 165.29, 163.72, 163.04, 162.75, 158.67, 156.80, 140.95, 137.47, 134.07, 130.81, 130.72, 130.62, 129.96, 128.65, 128.24, 116.32, 116.10, 53.17, 35.38.

20. Methyl 5-(benzoyloxy)-1-methyl-6-oxo-2-(pyridin-2-yl)-1,6-dihydropyrimidine-4-carboxylate

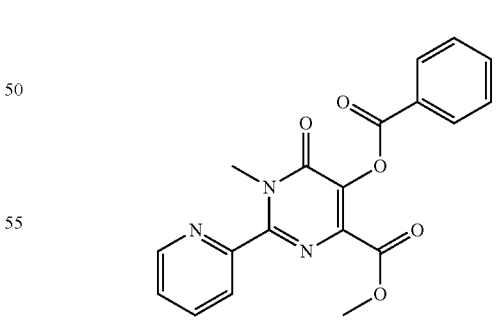

$^1$H NMR (400 MHz, CDCl$_3$) δ 8.67 (dt, J=4.8, 1.2 Hz, 1H), 8.21-8.15 (m, 2H), 7.91-7.84 (m, 2H), 7.65-7.57 (m, 1H), 7.48 (t, J=7.7 Hz, 2H), 7.42 (dd, J=9.1, 4.6 Hz, 1H), 3.80 (s, 3H), 3.64 (s, 3H). $^{13}$C NMR (101 MHz, CDCl$_3$) δ 163.68, 163.09, 158.74, 155.03, 152.24, 148.79, 140.67, 138.24, 137.64, 134.03, 130.67, 128.65, 128.33, 125.40, 125.34, 53.16, 34.60.

21. Methyl 5-(benzoyloxy)-1-methyl-2-(1-methyl-1H-imidazol-4-yl)-6-oxo-1,6-dihydropyrimidine-4-carboxylate

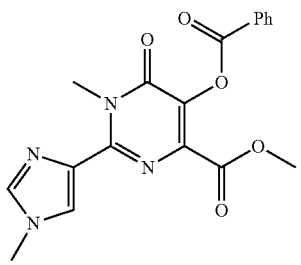 [SMILES: COC(=O)c1nc(-c2cn(C)cn2)n(C)c(=O)c1OC(=O)c1ccccc1]

$^1$H NMR (400 MHz, CDCl$_3$) δ 8.15 (s, 1H), 8.13 (d, J=1.2 Hz, 1H), 7.69 (s, 1H), 7.57 (t, J=7.4 Hz, 1H), 7.44 (t, J=7.6 Hz, 4H), 3.93 (s, 3H), 3.77 (s, 3H), 3.71 (s, 3H). $^{13}$C NMR (101 MHz, CDCl$_3$) δ 163.89, 163.42, 159.07, 151.52, 141.11, 137.74, 136.87, 136.21, 133.88, 130.60, 128.59, 128.54, 126.21, 77.39, 77.08, 76.76, 53.01, 34.21, 33.81.

22. Protocol A. General Preparation for the Amidation of 5,6-dihydroxypyrimidines-4-carboxyester

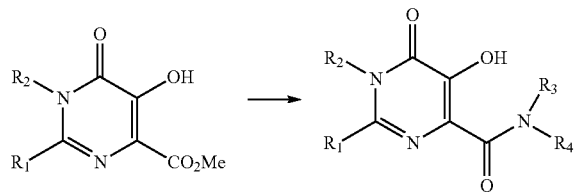

A 48-position MiniBlock XT containing 11.5×110 mm reaction tubes with stir bars was charged with a solution of starting 4,5-dihydroxypyrimidine methyl esters (0.15 mmol) in dimethylformamide or N-methyl-2-pyrrolidone (300 μL) to each vessel. 3 equivalents of the appropriate amine (0.45 mmol) from a 1M stock solution (dimethylformamide or N-methyl-2-pyrrolidone) are added accordingly to plate mapping. An inert atmosphere manifold is installed on the MiniBlock XT and the reactions are placed under a nitrogen atmosphere then gently heated to 90° C. and maintained for 8-16 hours with medium stirring. Once completed, the reactions are allowed to cool to room temperature, then diluted with 500 μL of DMSO, and transferred to a Thompson filter plate (pre-packed with celite connected to a Waters 2 mL 96-deep well plate). Following filtration and an additional washing of the filter plate with 200 μL more of DMSO, the crude products are analyzed by UPLC and purified by either Supercritical Fluid Chromatography (SFC) or Reverse Phase Liquid Chromatography (RPLC). Final purity was measured by the total wavelength current (TWC) from λ=210-400 nm on a UPLC.

23. Protocol A2. General Preparation for the Amidation of 5,6-dihydroxypyrimidines-4-carboxyester with Anilines In a 48 position reaction block containing 11.5×110 mm test tubes with a stir bar, a heat transfer condenser, and an inert atmosphere top, is added 1 equivalent ((0.05 mmol) of the 0.3M solution of methyl 5,6-dihydroxypyrimidine-4-carboxylates derivative (in NMP) followed by 3-5 equivalents of a 1M solution of the appropriate amine in NMP. The block is placed on a stir plate and heated to 160° C. while stirring for 8 hours. Once completed, the reactions are allowed to cool to room temperature, then diluted with 500 μL of DMSO, and transferred to a Thompson filter plate (pre-packed with celite connected to a Waters 2 mL 96-deep well plate). Following filtration and an additional washing of the filter plate with 200 μL more of DMSO, the crude products are analyzed by UPLC and purified by either Supercritical Fluid Chromatography (SFC) or Reverse Phase Liquid Chromatography (RPLC). Final purity is measured by the total wavelength current (TWC) from λ=210-400 nm on a UPLC.

24. Protocol B. General Preparation for the Amidation of 5-(benzoyloxy)-1,2-disubstituted-6-oxo-1,6-dihydropyrimidine-4-carboxyester

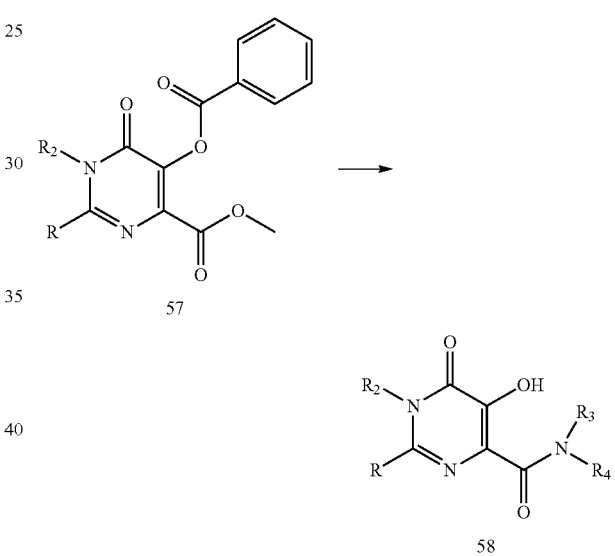

Final amidation of 57 to 58 follows the same general amidation of 5,6-dihydroxypyrimidines-4-carboxyester (see above), with the exception that 3-5 equivalents of appropriate amine were added.

25. Protocol B2. General Preparation for the Amidation of 5-(benzoyloxy)-1,2-disubstituted-6-oxo-1,6-dihydropyrimidine-4-carboxyester followed by t-butyl ester deprotection Amidation follows Protocol B, with the exception of not following the work-up involved in these protocols. To each crude products mixture (0.05 mmol scale), respectively from the previous reaction is added 10 mole equivalents of TFA followed by 0.2 mL of DCM. The XT block is replaced back on a stir plate, and permitted to stir until deemed complete by UPLC. Once completed, the reactions are then diluted with 500 μL of DMSO, and transferred to a Thompson filter plate (pre-packed with celite connected to a Waters 2 mL 96-deep well plate). Following filtration and an additional washing of the filter plate with 200 μL more of DMSO, the crude products are analyzed by UPLC and purified by either Supercritical Fluid Chromatography (SFC) or Reverse Phase Liquid Chromatography (RPLC). Final purity is measured by the total wavelength current (TWC) from λ=210-400 nm on a UPLC.

26. Protocol C. General Preparation for the Sequential Amidation of 5,6-dihydroxypyrimidines-4-carboxyester

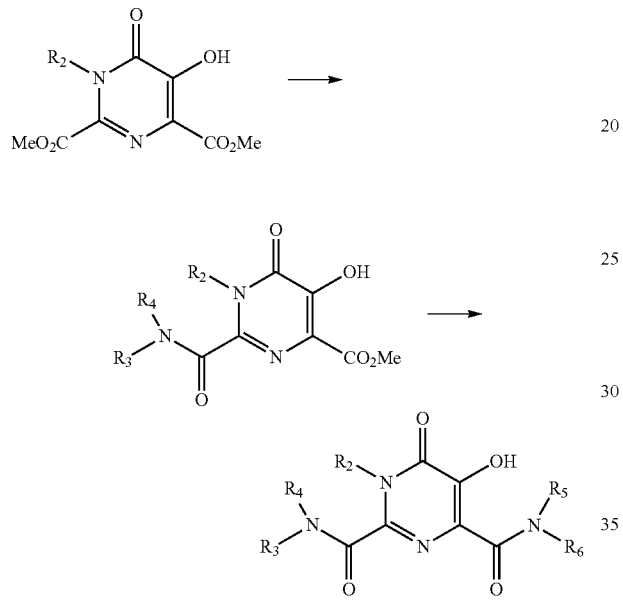

To a 48-position MiniBlock XT containing 11.5×110 mm reaction tubes with stir bars is charged with a solution of starting 4,5-dihydroxypyrimidine methyl esters (0.15 mmol) in dimethylformamide or N-methyl-2-pyrrolidone (300 μL) to each vessel. 2.5 equivalents of the appropriate amine (0.45 mmol) from a 1M stock solution (DMF or NMP) are added accordingly to plate mapping. An inert atmosphere manifold is installed on the MiniBlock XT and the reactions are placed under a nitrogen atmosphere then gently heated to 90° C. and maintained for 8-16 hours with medium stirring. 6 equivalents of the second appropriate amine (0.9 mmol, neat) are added accordingly to plate mapping. An inert atmosphere manifold is installed on the MiniBlock XT and the reactions are placed under a nitrogen atmosphere then gently heated to 90° C. and maintained for an additional 12-16 hours with medium stirring. Once completed, the reactions are allowed to cool to room temperature, then diluted with 500 μL of DMSO, and transferred to a Thompson filter plate (pre-packed with celite connected to a Waters 2 mL 96-deep well plate). Following filtration and an additional washing of the filter plate with 200 μL more of DMSO, the crude products are analyzed by UPLC, identifying the major peak as the desired product in each sample, then isolated and purified by either Supercritical Fluid Chromatography (SFC) or Reverse Phase Liquid Chromatography (RPLC). Final purity is measured by the total wavelength current (TWC) from λ=210-400 nm on a UPLC.

27. Protocol C2. General Preparation for the Sequential Amidation of 5,6-dihydroxypyrimidines-4-carboxyester

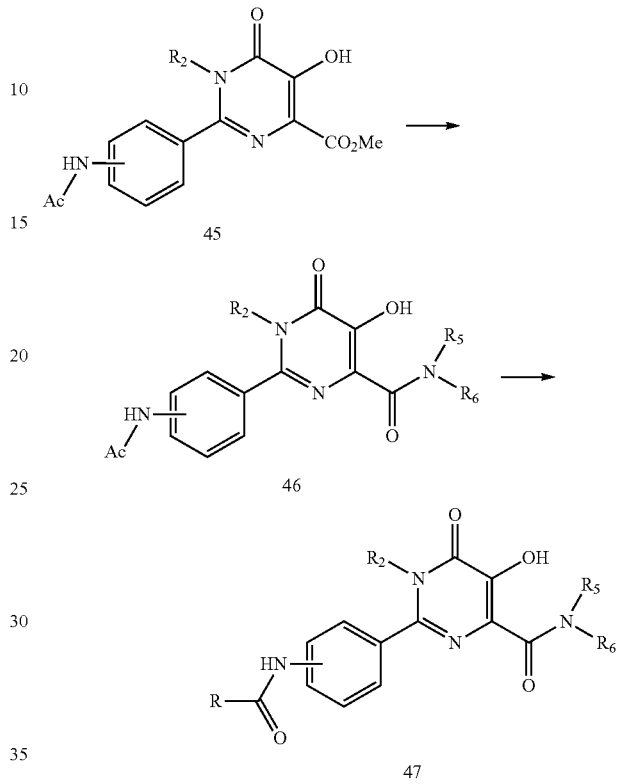

Conversion from 45 to 46 on scales ranging from 0.05 to 0.1 mmol follows either Protocol A, A2, or B, with the exception of not following the work-up involved in these protocols. With these crude reaction mixtures containing crude 46 is added 1 mL of methanol and 1 mL of 4M HCl in dioxane. The block is fitted with a sealing top then heated to 50° C. for 8 hrs when deemed completed by UPLC analysis. Once deprotection is complete, samples are concentrated in vacuo to near dryness, removing all traces of methanol. Samples are then fitted with an inert atmosphere manifold and flushed under nitrogen before adding dry DMF to an approximate 0.2M concentration. 10 equivalents of Et₃N is added followed by 2.5 equivalents of TMSCl and the mixture is stirred for 20 minutes at rt. Once time has completed, 6 equivalents of the appropriate acid chloride solution (previously prepared as a 1M stock solution in DMF) is then introduced and the reactions stirred at room temperature for at least 8 hours until deemed complete by UPLC, producing crude product 47. The reactions are then diluted with 500 μL of DMSO, and transferred to a Thompson filter plate (pre-packed with celite connected to a Waters 2 mL 96-deep well plate). Following filtration and an additional washing of the filter plate with 200 μL more of DMSO, the crude products are analyzed by UPLC, identifying the major peak as the desired product in each sample, then isolated and purified by either Supercritical Fluid Chromatography (SFC) or Reverse Phase Liquid Chromatography (RPLC). Final purity is measured by the total wavelength current (TWC) from λ=210-400 nm on a UPLC.

28. Protocol D. General Preparation for the Amidation of 6-amino-5-hydroxy-2-substituted pyrimidin-4(3H)-one

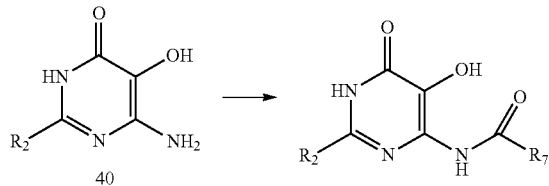

40

In a 48 position reaction block, incorporated with an inert atmosphere manifold, containing 11.5×110 mm test tubes with stir bars, 1.3 equivalent of the 1M solution of Benzotriazol-1-yloxytris(dimethylamino)-phosphonium hexafluorophosphate (commonly referred to as BOP) or 2-(1H-benzotriazole-1-yl)-1,1,3,3-tetramethyluronium hexafluorophosphate (commonly referred to as HBTU) in DMF is added followed by 1.5 equivalent of a 1M solution of triethylamine in DMF. The appropriate carboxylic acid solution (1.2 equivalent, 1M in DMF) is added followed by 1.0 equivalent of the 1M solution of the amine 40 in DMF. The inert atmosphere manifold is added to the block, and the block is placed on a stir plate at room temperature (20-25° C.) and stirred for 16 hours (overnight). Once complete, the mixtures are further diluted with DMSO while being transferred into Thompson 96 well filter plate packed with a small amount of Celilte 545 and attached to a Waters 96 well collection plate. Following filtration and an additional washing of the filter plate with 200 µL more of DMSO, the crude products are analyzed by UPLC and purified by either Supercritical Fluid Chromatography (SFC) or Reverse Phase Liquid Chromatography (RPLC). Final purity of the reverse amide product is measured by the total wavelength current (TWC) from $\lambda$=210-400 nm on a UPLC.

29. Protocol E. General Preparation for the Grignard organometalic addition of 4,5-dihydroxypyrimidines-4-carboxyester

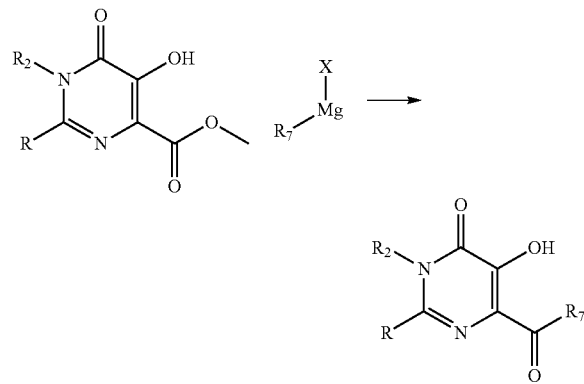

a. E1. If R2 is H or Alkylated and R does not Equal aryl.

In a 48 position reaction block containing 11.5×110 mm test tubes with a stir bar is added 1 equivalent of the 0.5M solution of methyl 5,6-dihydroxypyrimidine-4-carboxylates derivative followed by 1.2 equivalents of a 1M solution of the triethyl amine. An inert atmosphere top is attached and the system is placed under nitrogen. 1.2 equivalents of the 1M trimethylsilylchloride (TMSCl) solution is then added and the reaction stirred at rt for 15 minutes, followed by cooling to −40° C. using an acetonitrile bath with dry ice. Once the temperature is stabilized, 2 equivalents of the appropriate grinard is added accordingly at a reasonable speed by syringe. Once addition has been completed, the mixtures are stirred for 30 minutes to an hour at temperatures between −40° C. and −30° C. then quenched with saturated ammonium chloride solution (~200 uL) and allowed to warm to rt afterwards. The resulting mixture is diluted with ethyl acetate, extracted twice with ethyl acetate, the organic layers combined, and concentrated in vacuo. Each crude sample is diluted with 500 µL of DMSO, and transferred to a Thompson filter plate (pre-packed with celite connected to a Waters 2 mL 96-deep well plate). Following filtration and an additional washing of the filter plate with 200 µL more of DMSO, the crude products are analyzed by UPLC and purified by either Supercritical Fluid Chromatography (SFC) or Reverse Phase Liquid Chromatography (RPLC). Final purity is measured by the total wavelength current (TWC) from $\lambda$=210-400 nm on a UPLC. Typical yields ranged from 5-50% overall.

b. E2. If R Equals Aryl.

In a 2 mL microwave vial flushed with nitrogen containing a stir bar, sealed with an inert atmosphere top and flushed with nitrogen is added 500 µL (0.05 mmol) of the 0.1 M solution of methyl 5,6-dihydroxypyrimidine-4-carboxylates derivative followed by 2.2 equivalents of a 1 M solution of the triethyl amine. 2.2 equivalents of the 1 M TMSCl solution is then added with a syringe and the reaction stirred at rt for at least 10 minutes. Once complete, 3-3.2 equivalents of the appropriate Grignard is added accordingly at a reasonable speed by syringe. Once addition has been completed, the mixtures are microwaved at 100° C. for 30 minutes then cooled to rt afterwards and quenched with ammonium chloride solution. The resulting mixture is diluted with ethyl acetate, extracted twice with ethyl acetate, the organic layers combined, and concentrated in vacuo. Each crude sample is diluted with 500 µL of DMSO, and transferred to a Thompson filter plate (pre-packed with celite connected to a Waters 2 mL 96-deep well plate). Following filtration and an additional washing of the filter plate with 200 µL more of DMSO, the crude products are analyzed by UPLC and purified by either Supercritical Fluid Chromatography (SFC) or Reverse Phase Liquid Chromatography (RPLC). Final purity is measured by the total wavelength current (TWC) from $\lambda$=210-400 nm on a UPLC. Typical yields ranged from 5-50% overall.

c. E3. If Hindered Grignard Used.

In a 2 mL microwave vial containing a stir bar, sealed with an inert atmosphere top and flushed with nitrogen is added 500 µL (0.05 mmol) of the 0.1 M solution of methyl 5,6-dihydroxypyrimidine-4-carboxylates derivative followed by 2.2 equivalents of a 1M solution of the triethyl amine. 2.2 equivalents of the 1 M TMSCl solution is then added with a syringe and the reaction stirred at rt for at least 10 minutes. Once complete, 4.2 equivalents of the appropriate Grignard is added accordingly at a reasonable speed by syringe. Once addition has been completed, the mixture is microwaved at 100° C. for 30 minutes then cooled to rt afterwards and quenched with ammonium chloride solution (~100-200 µL), stirring for 5 minutes. The resulting mixture is diluted with ethyl acetate, extracted twice with ethyl acetate, the organic layers combined, and concentrated in vacuo. Each crude sample is diluted with 500 µL of DMSO, and transferred to a Thompson filter plate (pre-packed with celite connected to a Waters 2 mL 96-deep well plate). Following filtration and an additional washing of the filter plate with 200 μL more of DMSO, the crude products are analyzed by UPLC and purified by either Supercritical Fluid Chromatography (SFC) or Reverse Phase Liquid Chromatography (RPLC). Final purity is measured by the total wavelength current (TWC) from λ=210-400 nm on a UPLC. Typical isolated yields ranged from 5-50% overall.

30. Protocol F. General Preparation of 6-(1H-benzimidazol-2-yl)-4,5-dihydroxypyrimidines

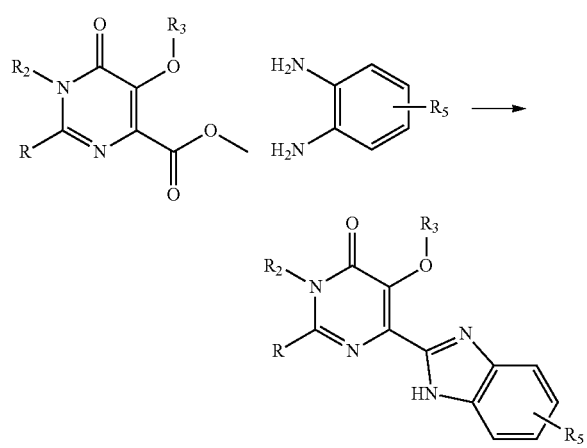

To ester (0.1 mmol) in an XT block with a cooled heat transfer block is added 500 μL of a 0.6M solution of diamine previously dissolved in 20% acetic acid in ethanol. The synthesizer is sealed with a septum top plate but not placed under any special atmosphere. The mixture then is refluxed for at least 20 hours until deemed complete by analysis; then cooled. Each crude sample is diluted with 500 μL of DMSO, and transferred to a Thompson filter plate (pre-packed with celite connected to a Waters 2 mL 96-deep well plate). Following filtration and an additional washing of the filter plate with 200 μL more of DMSO, the crude products are analyzed by UPLC and purified by either Supercritical Fluid Chromatography (SFC) or Reverse Phase Liquid Chromatography (RPLC). Final purity is measured by the total wavelength current (TWC) from λ=210-400 nm on a UPLC. Typical isolated yields ranged from 5-50% overall.

31. Protocol G. General Preparation of 5-hydroxy-2-substituted-6-(3-substituted-1,2,4-oxadiazol-5-yl)pyrimidin-4(3H)-one

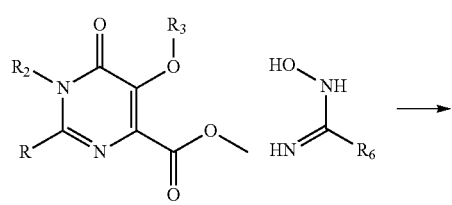

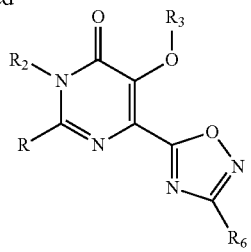

To ester (0.1 mmol) and amidoxime (3-5 equivalents) in 500 μL of ethanol is placed under nitrogen in an XT block with a cooled heat transfer block. 5 equivalents of 21% sodium ethoxide in ethanol is added by syringe and the mixture then is refluxed for at least 18 to 24 hours; then cooled. Each crude sample is diluted with 500 uL of DMSO, and transferred to a Thompson filter plate (pre-packed with celite connected to a Waters 2 mL 96-deep well plate). Following filtration and an additional washing of the filter plate with 200 μL more of DMSO, the crude products are analyzed by UPLC and purified by either Supercritical Fluid Chromatography (SFC) or Reverse Phase Liquid Chromatography (RPLC). Final purity is measured by the total wavelength current (TWC) from λ=210-400 nm on a UPLC. Typical isolated yields ranged from 5-50% overall.

32. 5,6-dihydroxy-N-(4-methylcyclohexyl)-2-(pyridin-2-yl)pyrimidine-4-carboxamide

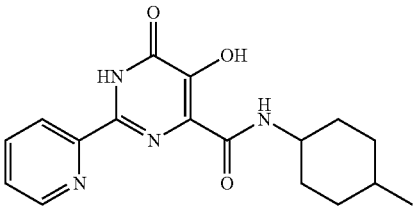 [SMILES: CC1CCC(NC(=O)c2nc(-c3ccccn3)[nH]c(=O)c2O)CC1]

Prepared according to Protocol A. Avg. Purity (TWC & ELSD): 100%. $^1$H NMR (400 MHz, DMSO) δ 9.16 (bs, 1H), 8.86 (bs, 1H), 8.76 (m, 3H), 8.65 (d, J=8.0 Hz, 1H), 8.22 (d, J=7.3 Hz, 2H), 7.80-7.65 (m, 2H), 3.98-3.72 (m, 2H), 1.98-1.51 (m, 13H), 1.51-1.30 (m, 3H), 1.01 (d, J=7.0 Hz, 4H), 0.91 (d, J=6.5 Hz, 3H). $^{13}$C NMR (101 MHz, DMSO) δ 167.21, 167.10, 158.18, 149.18, 146.22, 146.08, 142.67, 142.48, 126.71, 123.16, 122.97, 48.33, 47.73, 34.04, 33.61, 31.47, 31.37, 30.09, 27.13, 26.67, 22.19, 18.45. HRMS: m/z calcd for C17H21N4O3+ [M+H]:329.1614. found: 329.1609.

33. 5,6-dihydroxy-N-(naphthalen-1-ylmethyl)-2-(pyridin-2-yl)pyrimidine-4-carboxamide

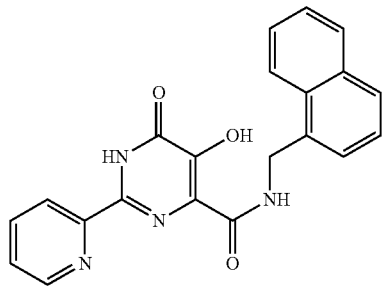 [SMILES: O=C(NCc1cccc2ccccc12)c1nc(-c2ccccn2)[nH]c(=O)c1O]

Prepared according to Protocol A. Avg. Purity (TWC & ELSD): 100%. ¹H NMR (400 MHz, DMSO-d6) δ 10.11 (s, 1H), 8.76 (dd, J=5.2, 3.4 Hz, 2H), 8.18 (t, J=7.8 Hz, 1H), 7.98-7.80 (m, 4H), 7.70 (dd, J=7.1, 5.8 Hz, 1H), 7.58 (dd, J=8.5, 1.5 Hz, 1H), 7.54-7.44 (m, 2H), 4.74 (d, J=6.4 Hz, 2H). ¹³C NMR (101 MHz, DMSO-d6) δ 168.47, 157.67, 149.43, 147.62, 147.18, 143.34, 136.10, 132.82, 132.16, 128.03, 127.56, 127.52, 126.31, 126.23, 125.93, 125.77, 125.66, 122.71, 42.42. HRMS: m/z calcd for C21H17N4O3+ [M+H]: 373.1301. found: 373.1310.

34. 5,6-dihydroxy-2-(pyridin-2-yl)-N-(1,2,3,4-tetrahydronaphthalen-1-yl)pyrimidine-4-carboxamide

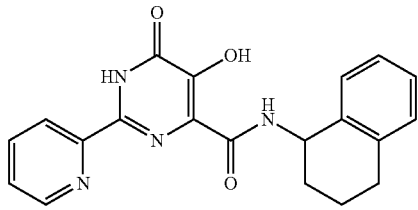 [SMILES: O=C(NC1CCCc2ccccc21)c1nc(-c2ccccn2)[nH]c(=O)c1O]

Prepared according to Protocol A. Avg. Purity (TWC & ELSD): 100%. ¹H NMR (400 MHz, DMSO) δ 9.50 (d, J=9.0 Hz, 1H), 8.73 (dd, J=15.1, 6.4 Hz, 2H), 8.06 (t, J=7.7 Hz, 1H), 7.70-7.55 (m, 1H), 7.18 (dd, J=5.4, 2.7 Hz, 4H), 5.32 (d, J=8.4 Hz, 2H), 2.96-2.68 (m, 2H), 2.13-1.93 (m, 3H), 1.82 (m, 1H). ¹³C NMR (101 MHz, DMSO) δ 168.32, 157.35, 149.84, 148.35, 147.89, 143.80, 137.25, 136.71, 128.89, 127.26, 126.83, 126.01, 122.62, 47.40, 29.40, 28.89, 21.14. HRMS: m/z calcd for C20H19N4O3+ [M+H]:363.1458. found: 363.1459.

35. 5,6-dihydroxy-N-(2-morpholinoethyl)-2-(pyridin-2-yl)pyrimidine-4-carboxamide

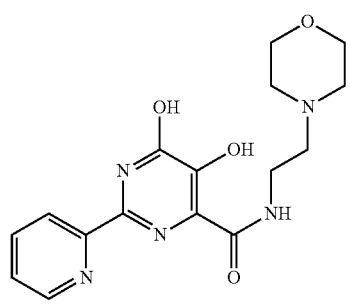 [SMILES: O=C(NCCN1CCOCC1)c1nc(-c2ccccn2)nc(O)c1O]

Prepared according to Protocol A. Avg. Purity (TWC & ELSD): 100%. ¹H NMR (400 MHz, CDCl₃) δ 8.66 (d, J=3.7, 1H), 8.43 (br s, 1H), 8.38 (d, J=7.5, 1H), 7.93 (t, J=7.6, 1H), 7.52-7.45 (m, 1H), 3.84 (s, 4H), 3.66 (d, J=5.6, 2H), 2.78 (t, J=6.0, 2H), 2.72 (m, 4H). HRMS: m/z calcd for C18H20N5O4+ [M+H]:346.1516. found: 346.1510.

36. 5,6-dihydroxy-2-(pyridin-2-yl)-N-(3-(pyrrolidin-1-yl)propyl)pyrimidine-4-carboxamide

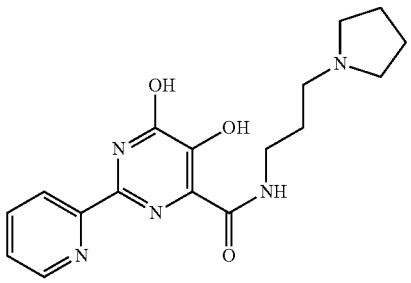 [SMILES: O=C(NCCCN1CCCC1)c1nc(-c2ccccn2)nc(O)c1O]

Prepared according to Protocol A. Avg. Purity (TWC & ELSD): 98.9%. ¹H NMR (400 MHz, CDCl₃) δ 8.75 (s, 1H), 8.63 (d, J=7.7, 1H), 8.51 (s, 1H), 8.48 (d, J=4.8, 1H), 7.78 (t, J=7.8, 1H), 7.35-7.27 (m, 1H), 3.51 (d, J=5.6, 2H), 3.07 (br s, 4H), 3.02 (dd, J=18.0, 10.9, 2H), 2.03 (dd, J=14.1, 7.7, 2H), 1.96 (s, 4H). HRMS: m/z calcd for C17H22N5O3+ [M+H]: 344.1723. found: 344.1735.

37. N-(3-(dimethylamino)-2,2-dimethylpropyl)-5,6-dihydroxy-2-(pyridin-2-yl)pyrimidine-4-carboxamide

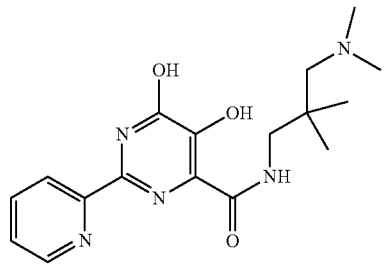 [SMILES: CN(C)CC(C)(C)CNC(=O)c1nc(-c2ccccn2)nc(O)c1O]

Prepared according to Protocol A. Avg. Purity (TWC & ELSD): 100%. ¹H NMR (400 MHz, CDCl₃) δ 9.12 (br s, 1H), 8.59-8.52 (m, 1H), 8.41 (dd, J=8.0, 0.9, 1H), 8.28 (s, 1H), 7.81 (td, J=7.8, 1.7, 1H), 7.41-7.33 (m, 1H), 3.41 (s, 2H), 2.63 (m, 8H), 1.12-1.02 (s, 6H). HRMS: m/z calcd for C17H24N5O3+ [M+H]:346.1880. found: 346.1873.

38. 5,6-dihydroxy-N-(2-Hydroxypropyl)-2-(pyridin-2-yl)pyrimidine-4-carboxamide

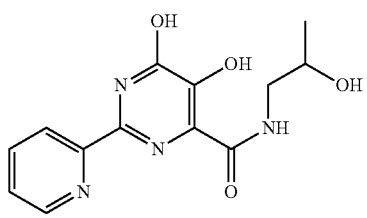 [SMILES: CC(O)CNC(=O)c1nc(-c2ccccn2)nc(O)c1O]

Prepared according to Protocol A. Avg. Purity (TWC & ELSD): 100%. ¹H NMR (400 MHz, CDCl₃) δ 12.48 (s, 1H), 11.08 (s, 1H), 8.53 (d, J=4.7, 1H), 8.21 (d, J=7.9, 1H), 8.02 (s, 1H), 7.81 (td, J=7.8, 1.5, 1H), 7.47-7.30 (m, 1H), 4.18-3.94 (m, 1H), 3.63 (ddd, J=13.9, 6.9, 3.1, 1H), 3.26 (ddd, J=13.5, 7.7, 5.5, 1H), 1.22 (t, J=15.2, 3H). HRMS: m/z calcd for C13H15N4O4+ [M+H]: 291.1094. found: 291.1094.

39. 5,6-dihydroxy-N-(4-hydroxybutyl)-2-(pyridin-2-yl)pyrimidine-4-carboxamide

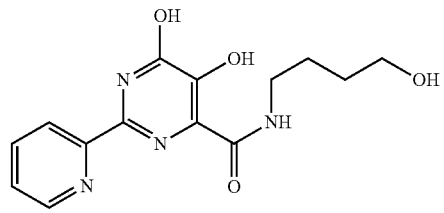 [SMILES: O=C(NCCCCO)c1nc(-c2ccccn2)nc(O)c1O]

Prepared according to Protocol A. Avg. Purity (TWC & ELSD): 95.3%. ¹H NMR (400 MHz, CDCl₃) δ 12.62 (s, 1H), 11.07 (s, 1H), 8.55 (d, J=4.8, 1H), 8.22 (d, J=7.9, 1H), 7.95-7.73 (m, 2H), 7.46-7.31 (m, 1H), 3.75-3.62 (m, 2H), 3.54-3.38 (m, 2H), 1.79-1.69 (m, 2H), 1.64 (dt, J=9.9, 6.5, 2H). HRMS: m/z calcd for C14H17N4O4+ [M+H]: 305.1251. found: 305.1258.

40. N-(2-cyanoethyl)-5,6-dihydroxy-2-(pyridin-2-yl)pyrimidine-4-carboxamide

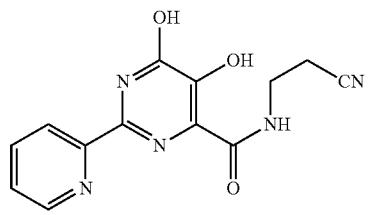 [SMILES: N#CCCNC(=O)c1nc(-c2ccccn2)nc(O)c1O]

Prepared according to Protocol A. Avg. Purity (TWC & ELSD): 100%. ¹H NMR (400 MHz, CDCl₃) δ 12.05 (s, 1H), 11.11 (s, 1H), 8.55 (m, 1H), 8.2 (m, 1H), 8.02 (s, 1H), 7.81 (m, 1H), 7.38 (m, 1H), 3.71 (q, J=6.4, 2H), 2.71 (t, J=6.3, 2H). HRMS: m/z calcd for C13H12N5O3+ [M+H]: 286.0941. found: 286.0937.

41. N-(3-(dibutylamino)propyl)-5,6-dihydroxy-2-(pyridin-2-yl)pyrimidine-4-carboxamide

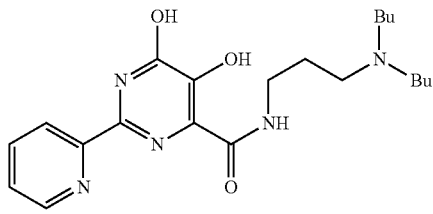

Prepared according to Protocol A. Avg. Purity (TWC & ELSD): 100%. ¹H NMR (400 MHz, CDCl₃) δ 8.80 (s, 1H), 8.61 (d, J=7.8, 1H), 8.56-8.41 (m, 2H), 7.80 (t, J=7.7, 1H), 7.40-7.29 (m, 1H), 3.51 (d, J=5.4, 2H), 2.98 (t, J=7.2, 2H), 2.92-2.77 (m, 4H), 2.07 (dd, J=13.0, 4.3, 2H), 1.68-1.45 (m, 4H), 1.37-1.17 (m, 4H), 0.85 (t, J=7.3, 6H). HRMS: m/z calcd for C21H132N5O3+ [M+H]: 402.2506. found: 402.2496.

42. 5,6-dihydroxy-N-(3-(2-oxopyrrolidin-1-yl)propyl)-2-(pyridin-2-yl)pyrimidine-4-carboxamide

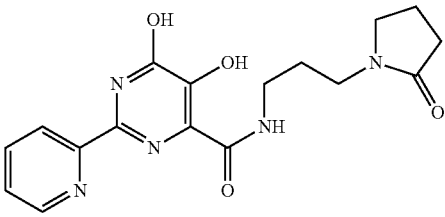 [SMILES: O=C(NCCCN1CCCC1=O)c1nc(-c2ccccn2)nc(O)c1O]

Prepared according to Protocol A. Avg. Purity (TWC & ELSD): 100%. ¹H NMR (400 MHz, CDCl₃) δ 12.61 (s, 1H), 11.05 (s, 1H), 8.94 (s, 1H), 8.65 (d, J=8.0, 1H), 8.59-8.42 (m, 1H), 7.82 (td, J=7.8, 1.7, 1H), 7.33 (ddd, J=7.5, 4.8, 1.1, 1H), 3.45-3.25 (m, 6H), 2.39 (t, J=8.1, 2H), 2.09-1.93 (m, 2H), 1.72 (dq, J=12.0, 6.0, 2H). HRMS: m/z calcd for C17H20N5O4+ [M+H]: 358.1516. found: 358.1523.

43. 5,6-dihydroxy-N-(2-methoxyethyl)-2-(pyridin-2-yl)pyrimidine-4-carboxamide

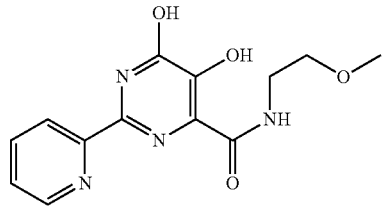 [SMILES: COCCNC(=O)c1nc(-c2ccccn2)nc(O)c1O]

Prepared according to Protocol A. Avg. Purity (TWC & ELSD): 100%. ¹H NMR (400 MHz, CDCl₃) δ 12.51 (s, 1H), 11.07 (s, 1H), 8.54 (ddd, J=4.8, 1.6, 0.9, 1H), 8.21 (dt, J=8.0, 1.0, 1H), 7.93 (s, 1H), 7.88-7.72 (m, 1H), 7.37 (ddd, J=7.6, 4.8, 1.1, 1H), 3.59 (m, 2H), 3.57-3.49 (m, 2H), 3.35 (s, 3H). HRMS: m/z calcd for C13H15N4O4+ [M+H]: 291.1094. found: 291.1096.

44. 5,6-dihydroxy-N-(3-methoxypropyl)-2-(pyridin-2-yl)pyrimidine-4-carboxamide

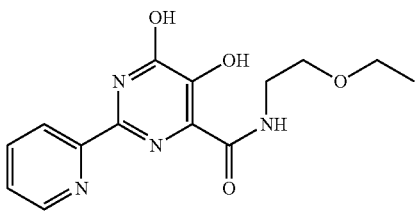 [SMILES: CCOCCNC(=O)c1nc(-c2ccccn2)nc(O)c1O]

Prepared according to Protocol A. Avg. Purity (TWC & ELSD): 100%. ¹H NMR (400 MHz, CDCl₃) δ 12.77 (s, 1H), 11.14 (s, 1H), 8.65 (ddd, J=4.8, 1.6, 0.9, 1H), 8.47-8.24 (m, 2H), 7.90 (td, J=7.8, 1.7, 1H), 7.56-7.41 (m, 1H), 3.71-3.56 (m, 4H), 3.46 (d, J=6.3, 3H), 1.97 (td, J=11.2, 5.8, 2H). HRMS: m/z calcd for C14H17N4O4+ [M+H]: 305.1251. found: 305.1257.

45. 5,6-dihydroxy-2-(pyridin-2-yl)-N-((tetrahydrofuran-2-yl)methyl)pyrimidine-4-carboxamide

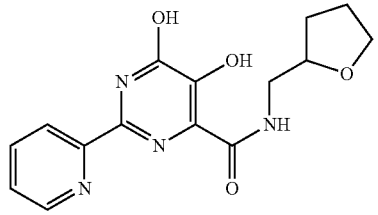 [SMILES: O=C(NCC1CCCO1)c1nc(-c2ccccn2)nc(O)c1O]

Prepared according to Protocol A. Avg. Purity (TWC & ELSD): 100%. ¹H NMR (400 MHz, CDCl₃) δ 12.54 (s, 1H), 11.07 (s, 1H), 8.61-8.46 (m, 1H), 8.31-8.13 (m, 1H), 7.94 (s, 1H), 7.81 (td, J=7.8, 1.7, 1H), 7.44-7.31 (m, 1H), 4.04 (qd, J=7.1, 3.3, 1H), 3.87 (dt, J=8.2, 6.7, 1H), 3.80-3.72 (m, 1H), 3.67 (ddd, J=13.9, 6.6, 3.3, 1H), 3.39-3.27 (m, 1H), 1.99 (dt, J=12.2, 6.9, 1H), 1.93-1.81 (m, 2H), 1.56 (ddd, J=15.2, 12.2, 7.5, 2H). HRMS: m/z calcd for C15H17N4O4+ [M+H]: 317.1251. found: 317.1236.

46. 5,6-dihydroxy-N-(1-methoxypropan-2-yl)-2-(pyridin-2-yl)pyrimidine-4-carboxamide

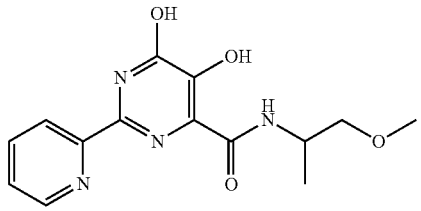 [SMILES: COCC(C)NC(=O)c1nc(-c2ccccn2)nc(O)c1O]

Prepared according to Protocol A. Avg. Purity (TWC & ELSD): 100%. ¹H NMR (400 MHz, CDCl₃) δ 12.62 (s, 1H), 11.07 (s, 1H), 8.54 (ddd, J=4.8, 1.6, 0.9, 1H), 8.19 (dt, J=8.0, 1.0, 1H), 7.85-7.7 (m, 2H), 7.47-7.28 (m, 1H), 4.39-4.16 (m, 1H), 3.49-3.39 (m, 2H), 3.36 (s, 3H) 1.27 (d, J=6.8, 3H). HRMS: m/z calcd for C14H17N4O4+ [M+H]: 305.1251. found: 305.1251.

47. N-(3-ethoxypropyl)-5,6-dihydroxy-2-(pyridin-2-yl)pyrimidine-4-carboxamide

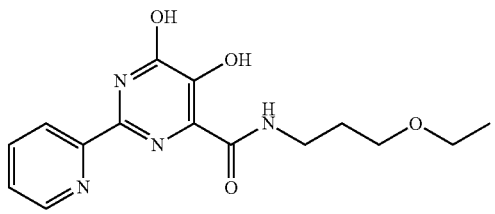 [SMILES: CCOCCCNC(=O)c1nc(-c2ccccn2)nc(O)c1O]

Prepared according to Protocol A. Avg. Purity (TWC & ELSD): 100%. ¹H NMR (400 MHz, CDCl₃) δ 12.83 (s, 1H), 11.15 (s, 1H), 8.66 (dd, J=15.0, 14.1, 1H), 8.30 (m, 1H), 8.20 (s, 1H), 7.95-7.79 (m, 1H), 7.47 (ddd, J=7.6, 4.9, 1.0, 1H), 3.67-3.49 (m, 6H), 2.04-1.89 (m, 2H), 1.33-1.18 (m, 3H). HRMS: m/z calcd for C15H19N4O4+ [M+H]: 319.1407. found: 319.1404.

48. 5,6-dihydroxy-N-propyl-2-(pyridin-2-yl)pyrimidine-4-carboxamide

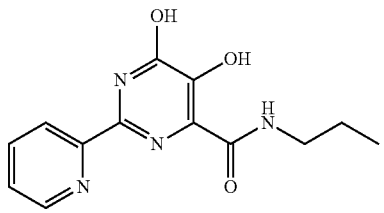 [SMILES: CCCNC(=O)c1nc(-c2ccccn2)nc(O)c1O]

Prepared according to Protocol A. Avg. Purity (TWC & ELSD): 100%. ¹H NMR (400 MHz, CDCl₃) δ 12.65 (s, 1H), 11.06 (s, 1H), 8.55 (ddd, J=4.8, 1.6, 0.9, 1H), 8.19 (dt, J=8.0, 1.0, 1H), 7.81 (td, J=7.8, 1.7, 1H), 7.64 (s, 1H), 7.45-7.32 (m, 1H), 3.45-3.29 (m, 2H), 1.74-1.55 (m, 2H), 0.95 (t, J=7.4, 3H). HRMS: m/z calcd for C13H15N4O3+ [M+H]: 275.1145. found: 275.1139.

49. N-(cyclopropylmethyl)-5,6-dihydroxy-2-(pyridin-2-yl)pyrimidine-4-carboxamide

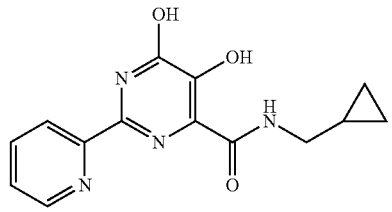 [SMILES: O=C(NCC1CC1)c1nc(-c2ccccn2)nc(O)c1O]

Prepared according to Protocol A. Avg. Purity (TWC & ELSD): 98.7%. ¹H NMR (400 MHz, CDCl₃) δ 12.65 (s, 1H), 11.08 (s, 1H), 8.67-8.47 (m, 1H), 8.34-8.13 (m, 1H), 7.83 (ddd, J=8.1, 1.6, 0.8, 1H), 7.71 (s, 1H), 7.49-7.30 (m, 1H), 3.36-3.21 (m, 2H), 1.16-0.93 (m, 1H), 0.67-0.42 (m, 2H), 0.29 (dq, J=10.4, 5.1, 2H). HRMS: m/z calcd for C14H15N4O3+ [M+H]: 287.1145. found: 287.1147.

50. Ethyl 3-(5,6-dihydroxy-2-(pyridin-2-yl)pyrimidine-4-carboxamido)butanoate

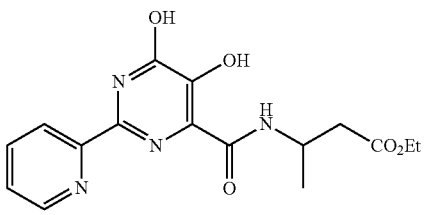 [SMILES: CCOC(=O)CC(C)NC(=O)c1nc(-c2ccccn2)nc(O)c1O]

Prepared according to Protocol A. Avg. Purity (TWC & ELSD): 100%. ¹H NMR (400 MHz, CDCl₃) δ 12.52 (s, 1H), 11.05 (s, 1H), 8.64-8.50 (m, 1H), 8.42 (d, J=8.3, 1H), 8.36-8.20 (m, 1H), 7.84 (td, J=7.8, 1.7, 1H), 7.47-7.31 (m, 1H), 4.45 (ddd, J=14.1, 6.9, 5.1, 1H), 4.29-4.04 (m, 2H), 2.71-2.50 (m, 2H), 1.33 (d, J=6.8, 3H), 1.22 (t, J=7.1, 3H). HRMS: m/z calcd for C16H19N4O5+ [M+H]: 347.1356. found: 347.1357.

51. N-cyclobutyl-5,6-dihydroxy-2-(pyridin-2-yl)pyrimidine-4-carboxamide

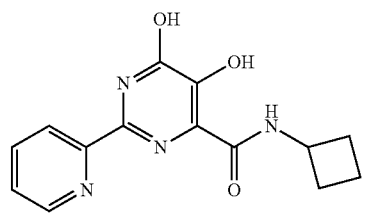 [SMILES: O=C(NC1CCC1)c1nc(-c2ccccn2)nc(O)c1O]

Prepared according to Protocol A. Avg. Purity (TWC & ELSD): 100%. ¹H NMR (400 MHz, DMSO) δ 12.92 (s, 1H), 11.82 (s, 1H), 8.61 (m, 2H), 7.94-7.86 (m, 1H), 4.42 (dd, J=16.8, 8.5, 1H), 2.31-2.15 (m, 4H), 1.76-1.62 (m, 2H). HRMS: m/z calcd for C14H15N4O3+ [M+H]: 287.1145. found: 287.1139.

52. N-(2,2-diethoxyethyl)-5,6-dihydroxy-2-(pyridin-2-yl)pyrimidine-4-carboxamide

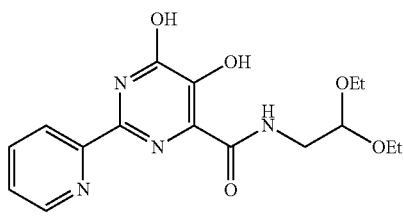 [SMILES: CCOC(CNC(=O)c1nc(-c2ccccn2)nc(O)c1O)OCC]

Prepared according to Protocol A. Avg. Purity (TWC & ELSD): 100%. ¹H NMR (400 MHz, CDCl₃) δ 12.54 (s, 1H), 11.17 (s, 1H), 8.76-8.59 (m, 1H), 8.30 (d, J=8.0, 1H), 8.12-7.83 (m, 2H), 7.61-7.40 (m, 1H), 4.67 (t, J=5.3, 1H), 3.91-3.73 (m, 2H), 3.73-3.53 (m, 4H), 1.38-1.15 (m, 6H). HRMS: m/z calcd for C16H21N4O5+ [M+H]: 349.1513. found: 349.1522.

53. 5,6-dihydroxy-N-(3-isopropdxypropyl)-2-(pyridin-2-yl)pyrimidine-4-carboxamide

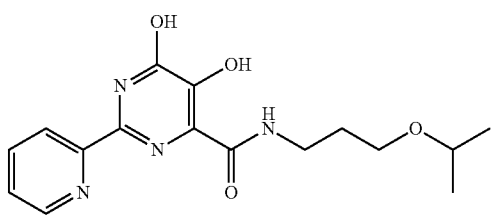 [SMILES: CC(C)OCCCNC(=O)c1nc(-c2ccccn2)nc(O)c1O]

Prepared according to Protocol A. Avg. Purity (TWC & ELSD): 100%. ¹H NMR (400 MHz, CDCl₃) δ 12.76 (s, 1H), 11.05 (s, 1H), 8.65-8.46 (m, 1H), 8.23 (dt, J=8.0, 1.0, 1H), 8.00 (s, 1H), 7.87-7.70 (m, 1H), 7.46-7.26 (m, 1H), 3.66-3.43 (m, 5H), 1.96-1.77 (m, 2H), 1.22-1.05 (m, 6H). HRMS: m/z calcd for C16H21N4O4+ [M+H]: 333.1564. found: 333.1555.

54. 5,6-dihydroxy-N-isobutyl-2-(pyridin-2-yl)pyrimidine-4-carboxamide

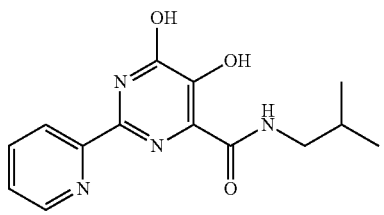 [SMILES: CC(C)CNC(=O)c1nc(-c2ccccn2)nc(O)c1O]

Prepared according to Protocol A. Avg. Purity (TWC & ELSD): 100%. ¹H NMR (400 MHz, CDCl₃) δ 12.65 (s, 1H), 11.08 (s, 1H), 8.57-8.54 (m, 1H), 8.19 (dd, J=7.9, 0.8, 1H), 7.82 (ddd, J=8.0, 1.7, 0.8, 1H), 7.71 (s, 1H), 7.41-7.36 (m, 1H), 3.25 (t, J=6.6, 2H), 1.89 (dp, J=13.4, 6.7, 1H), 0.96 (d, J=6.7, 7H). HRMS: m/z calcd for C14H17N4O3+ [M+H]: 289.1301. found: 289.1300.

55. 5,6-dihydroxy-N-(4-methoxybenzyl)-2-(pyridin-2-yl)pyrimidine-4-carboxamide

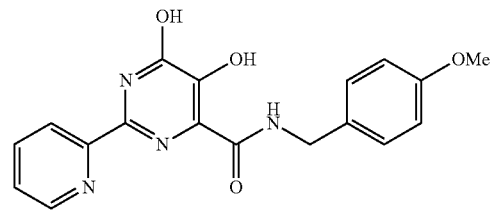 [SMILES: COc1ccc(CNC(=O)c2nc(-c3ccccn3)nc(O)c2O)cc1]

Prepared according to Protocol A. Avg. Purity (TWC & ELSD): 100%. ¹H NMR (400 MHz, CDCl₃) δ 12.52 (s, 1H), 11.11 (s, 1H), 8.53 (ddd, J=4.8, 1.6, 0.9, 1H), 8.17-8.13 (m, 1H), 7.86 (s, 1H), 7.77 (td, J=7.8, 1.7, 1H), 7.36 (ddd, J=7.6, 4.8, 1.1, 1H), 7.27-7.21 (m, 2H), 6.87-6.82 (m, 2H), 4.54 (d, J=6.1, 2H), 3.73 (d, J=7.6, 3H). HRMS: m/z calcd for C18H17N4O4+ [M+H]: 353.1251. found: 353.1246.

56. N-butyl-4,6-dihydroxy-2-(pyridin-2-yl)pyrimidine-4-carboxamide

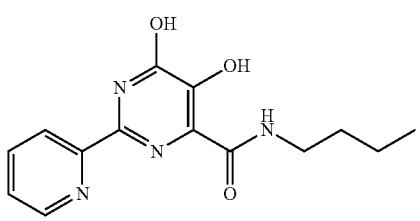 [SMILES: CCCCNC(=O)c1nc(-c2ccccn2)nc(O)c1O]

Prepared according to Protocol A. Avg. Purity (TWC & ELSD): 100%. ¹H NMR (400 MHz, CDCl₃) δ 12.67 (s, 1H), 11.07 (s, 1H), 8.56 (dd, J=4.8, 0.9, 1H), 8.21 (d, J=8.0, 1H), 7.82 (td, J=7.8, 1.6, 1H), 7.63 (s, 1H), 7.41-7.36 (m, 1H), 3.45-3.38 (m, 2H), 1.64-1.46 (m, 2H), 1.44-1.33 (m, 2H), 0.93 (t, J=7.3, 3H). HRMS: m/z calcd for C14H17N4O34+ [M+H]: 289.1301. found: 289.1299.

57. N-benzyl-5,6-dihydroxy-2-(pyridin-2-yl)pyrimidine-4-carboxamide

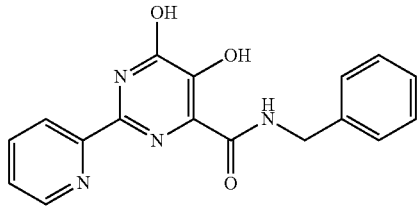 [SMILES: O=C(NCc1ccccc1)c1nc(-c2ccccn2)nc(O)c1O]

Prepared according to Protocol A. Avg. Purity (TWC & ELSD): 100%. ¹H NMR (400 MHz, CDCl₃) δ 12.47 (s, 1H), 11.12 (s, 1H), 8.57-8.53 (m, 1H), 8.16 (dd, J=8.0, 1.0, 1H), 7.93 (s, 1H), 7.78 (td, J=7.8, 1.7, 1H), 7.34-7.30 (m, 6H), 4.62 (d, J=6.2, 2H). HRMS: m/z calcd for C17H15N4O3+ [M+H]: 323.1145. found: 323.1143.

58. N-cyclopentyl-5,6-dihydroxy-2-(pyridin-2-yl)pyrimidine-4-carboxamide

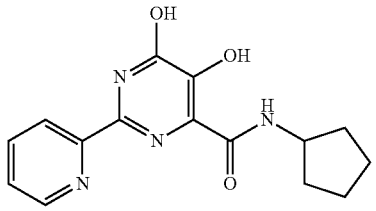 [SMILES: O=C(NC1CCCC1)c1nc(-c2ccccn2)nc(O)c1O]

Prepared according to Protocol A. Avg. Purity (TWC & ELSD): 100%. ¹H NMR (400 MHz, CDCl₃) δ 12.59 (s, 1H), 11.84-11.00 (s, 1H), 8.65 (d, J=3.8, 1H), 8.28 (d, J=7.8, 1H), 8.00-7.87 (m, 1H), 7.62 (s, 1H), 7.48 (dd, J=7.5, 4.7, 1H), 4.40 (dd, J=14.1, 7.1, 1H), 2.25-2.07 (m, 2H), 1.90-1.54 (m, 6H). HRMS: m/z calcd for C15H17N4O3+ [M+H]: 301.1301. found: 301.1301.

59. N-(4-fluorobenzyl)-5,6-dihydroxy-2-(pyridin-2-yl)pyrimidine-4-carboxamide

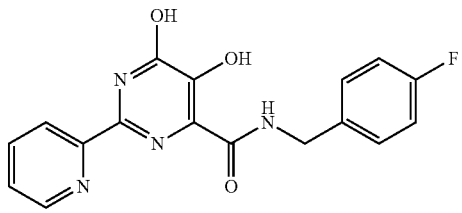 [SMILES: O=C(NCc1ccc(F)cc1)c1nc(-c2ccccn2)nc(O)c1O]

Prepared according to Protocol A. Avg. Purity (TWC & ELSD): 98.2%. ¹H NMR (400 MHz, CDCl₃) δ 12.44 (s, 1H), 11.10 (s, 1H), 8.53 (ddd, J=4.8, 1.6, 0.9, 1H), 8.15 (dt, J=8.0, 1.0, 1H), 7.91 (s, 1H), 7.77 (td, J=7.8, 1.7, 1H), 7.36 (ddd, J=7.6, 4.8, 1.1, 1H), 7.30-7.25 (m, 2H), 7.02-6.96 (m, 2H), 4.54 (dd, J=17.2, 6.0, 2H). HRMS: m/z calcd for C17H14FN4O3+ [M+H]: 341.1051. found: 341.1049.

60. 5,6-dihydroxy-N-isopentyl-2-(pyridin-2-yl)pyrimidine-4-carboxamide

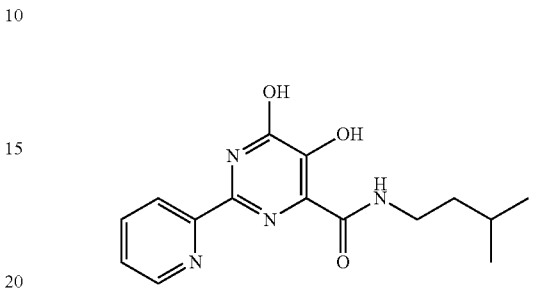

Prepared according to Protocol A. Avg. Purity (TWC & ELSD): 100%. ¹H NMR (400 MHz, CDCl₃) δ 12.76 (s, 1H), 11.18 (s, 1H), 8.65 (d, J=3.1, 1H), 8.30 (d, J=7.9, 1H), 7.92 (td, J=7.8, 1.7, 1H), 7.70 (s, 1H), 7.51-7.44 (m, 1H), 3.53 (dt, J=12.3, 4.9, 2H), 1.75 (dt, J=13.2, 6.6, 1H), 1.71-1.57 (m, 2H), 1.02 (dd, J=6.6, 3.7, 6H). HRMS: m/z calcd for C15H19N4O3+ [M+H]: 303.1458. found: 303.1449.

61. 5,6-dihydroxy-N-(2-methylbutyl)-2-(pyridin-2-yl)pyrimidine-4-carboxamide

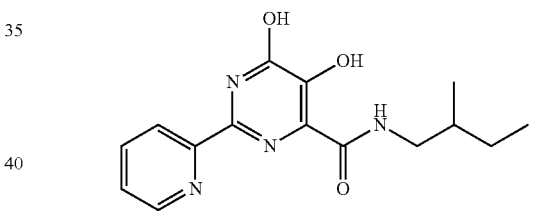

Prepared according to Protocol A. Avg. Purity (TWC & ELSD): 100%. ¹H NMR (400 MHz, CDCl₃) δ 12.76 (s, 1H), 11.17 (s, 1H), 8.65 (ddd, J=4.8, 1.6, 0.9, 1H), 8.28 (dt, J=8.0, 1.0, 1H), 7.92 (td, J=7.8, 1.7, 1H), 7.78 (s, 1H), 7.48 (ddd, J=7.6, 4.8, 1.1, 1H), 3.45 (dt, J=12.5, 6.2, 1H), 3.33 (dt, J=13.5, 6.8, 1H), 1.76 (tt, J=13.2, 6.8, 1H), 1.58-1.46 (m, 1H), 1.28 (ddd, J=22.4, 14.9, 7.5, 1H), 1.06-0.97 (m, 6H). HRMS: m/z calcd for C153H19N4O3+ [M+H]: 303.1458. found: 303.1459.

62. N-cyclohexyl-5,6-dihydroxy-2-(pyridin-2-yl)pyrimidine-4-carboxamide

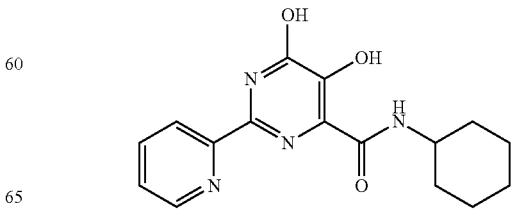

Prepared according to Protocol A. Avg. Purity (TWC & ELSD): 100%. ¹H NMR (400 MHz, CDCl$_3$) δ 12.58 (s, 1H), 11.55-10.72 (m, 1H), 8.56 (dd, J=4.8, 0.9, 1H), 8.19 (dd, J=8.0, 0.9, 1H), 7.83 (td, J=7.8, 1.7, 1H), 7.49 (d, J=8.3, 1H), 7.39 (ddd, J=7.6, 4.8, 1.1, 1H), 3.89 (tt, J=14.3, 7.1, 1H), 1.97 (d, J=12.2, 2H), 1.78-1.68 (m, 2H), 1.67-1.46 (m, 2H), 1.46-1.15 (m, 4H). HRMS: m/z calcd for C16H19N4O3+ [M+H]: 315.1458. found: 315.1453.

63. 5,6-dihydroxy-2-(pyridin-2-yl)-N-(3-(trifluoromethyl)benzyl)pyrimidine-4-carboxamide

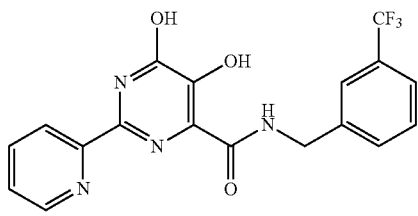 [SMILES: O=C(NCc1cccc(C(F)(F)F)c1)c1nc(-c2ccccn2)nc(O)c1O]

Prepared according to Protocol A. Avg. Purity (TWC & ELSD): 100%. ¹H NMR (400 MHz, CDCl$_3$) δ 12.48 (s, 1H), 11.20 (s, 1H), 8.65 (d, J=4.8, 1H), 8.28 (d, J=7.9, 1H), 8.11 (s, 1H), 7.89 (td, J=7.8, 1.6, 1H), 7.68-7.50 (m, 5H), 7.5-7.45 (m, 1H), 4.77 (d, J=6.3, 2H). HRMS: m/z calcd for C18H13F3N4O3+ [M+H]: 391.1019. found: 391.1008.

64. 5,6-dihydroxy-2-(pyridin-2-yl)-N-(4-(trifluoromethyl)benzyl)pyrimidine-4-carboxamide

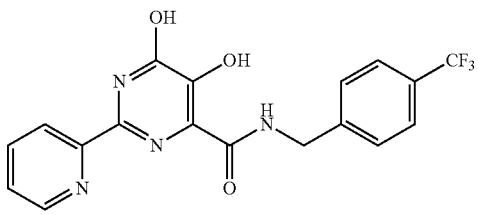 [SMILES: O=C(NCc1ccc(C(F)(F)F)cc1)c1nc(-c2ccccn2)nc(O)c1O]

Prepared according to Protocol A. Avg. Purity (TWC & ELSD): 100%. ¹H NMR (400 MHz, CDCl$_3$) δ 12.52 (s, 1H), 11.25 (s, 1H), 8.66 (s, 1H), 8.28 (m, 1H), 8.10 (s, 1H), 7.89 (m, 1H), 7.67 (m, 2H), 7.54 (m, 2H), 7.50-7.42 (m, 1H), 4.78 (d, J=5.6, 2H). HRMS: m/z calcd for C18H14F3N4O3+ [M+H]: 391.1019. found: 391.1020.

65. N-(3,3-dimethylbutyl)-5,6-dihydroxy-2-(pyridin-2-yl)pyrimidine-4-carboxamide

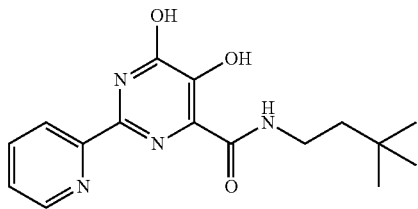 [SMILES: CC(C)(C)CCNC(=O)c1nc(-c2ccccn2)nc(O)c1O]

Prepared according to Protocol A. Avg. Purity (TWC & ELSD): 100%. ¹H NMR (400 MHz, CDCl$_3$) δ 12.75 (s, 1H), 11.17 (s, 1H), 8.67-8.63 (m, 1H), 8.30 (dd, J=8.0, 0.9, 1H), 7.91 (td, J=7.8, 1.7, 1H), 7.67 (s, 1H), 7.51-7.44 (m, 1H), 3.57-3.47 (m, 2H), 1.68-1.55 (m, 2H), 1.04 (d, J=2.0, 9H). HRMS: m/z calcd for C16H21N4O3+ [M+H]: 317.1614. found: 317.1614.

66. 5,6-dihydroxy-N-(4-methylpentan-2-yl)-2-(pyridin-2-yl)pyrimidine-4-carboxamide

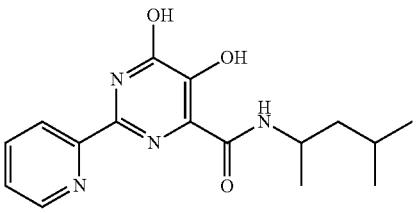 [SMILES: CC(C)CC(C)NC(=O)c1nc(-c2ccccn2)nc(O)c1O]

Prepared according to Protocol A. Avg. Purity (TWC & ELSD): 100%. ¹H NMR (400 MHz, CDCl$_3$) δ 12.85 (s, 1H), 11.17 (s, 1H), 8.67-8.63 (m, 1H), 8.29 (dd, J=8.0, 0.9, 1H), 7.93 (td, J=7.8, 1.7, 1H), 7.51-7.43 (m, 2H), 4.36-4.20 (m, 1H), 1.78-1.51 (m, 2H), 1.45 (ddd, J=13.8, 7.8, 6.2, 1H), 1.32 (d, J=6.5, 3H), 1.00 (dd, J=6.5, 4.7, 6H). HRMS: m/z calcd for C16H21N4O3+ [M+H]: 317.1614. found: 317.1612.

67. 5,6-dihydroxy-N-(2-methylcyclohexyl)-2-(pyridin-2-yl)pyrimidine-4-carboxamide

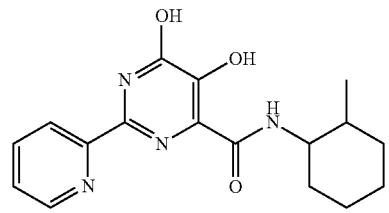 [SMILES: CC1CCCCC1NC(=O)c1nc(-c2ccccn2)nc(O)c1O]

Prepared according to Protocol A. Avg. Purity (TWC & ELSD): 100%. ¹H NMR (400 MHz, CDCl$_3$) δ 12.73 (s, 1H), 11.30 (s, 1H), 8.66 (d, J=3.1, 1H), 8.30 (dd, J=7.9, 0.9, 1H), 7.93 (td, J=7.8, 1.7, 1H), 7.51-7.45 (m, 1H), 3.67 (dd, J=20.5, 10.7, 1H), 2.09 (d, J=12.8, 1H), 1.91-1.50 (m, 8H), 1.08-0.94 (m, 3H). HRMS: m/z calcd for C17H21N4O3+ [M+H]: 329.1614. found: 329.1617.

68. N-(3,4-dichlorobenzyl)-5,6-dihydroxy-2-(pyridin-2-yl)pyrimidine-4-carboxamide

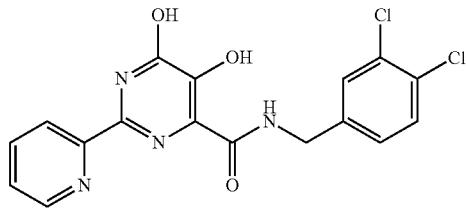 [SMILES: O=C(NCc1ccc(Cl)c(Cl)c1)c1nc(-c2ccccn2)nc(O)c1O]

Prepared according to Protocol A. Avg. Purity (TWC & ELSD): 100%. ¹H NMR (400 MHz, CDCl₃) δ 12.33 (s, 1H), 11.11 (s, 1H), 8.55 (s, 1H), 8.18 (d, J=7.9, 1H), 7.96 (s, 1H), 7.80 (s, 1H), 7.43-7.34 (m, 4H), 7.30 (s, 1H), 4.57 (m, 2H). HRMS: m/z calcd for C17H14Cl2N4O3+ [M+H]: 391.0365. found: 391.0369.

69. N-(heptan-2-yl)-5,6-dihydroxy-2-(pyridin-2-yl)pyrimidine-4-carboxamide

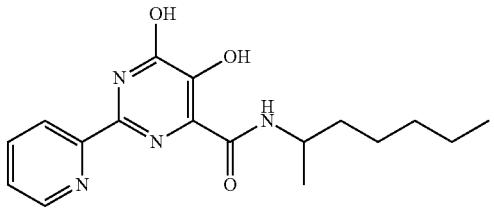 [SMILES: CCCCCC(C)NC(=O)c1nc(-c2ccccn2)nc(O)c1O]

Prepared according to Protocol A. Avg. Purity (TWC & ELSD): 100%. ¹H NMR (400 MHz, CDCl₃) δ 12.75 (s, 1H), 11.09 (s, 1H), 8.58-8.53 (m, 1H), 8.20 (dd, J=8.0, 0.9, 1H), 7.83 (td, J=7.8, 1.7, 1H), 7.39 (ddd, J=7.5, 4.8, 1.1, 2H), 4.17-3.98 (m, 1H), 1.58 1.49 (m, 3H), 1.30-1.20 (m, 8H), 0.83 (dd, J=8.8, 5.3, 3H). HRMS: m/z calcd for C17H23N4O3+ [M+H]: 331.1771. found: 331.1775.

70. N-(2-ethylhexyl)-5,6-dihydroxy-2-(pyridine-2-yl)pyrimidine-4-carboxamide

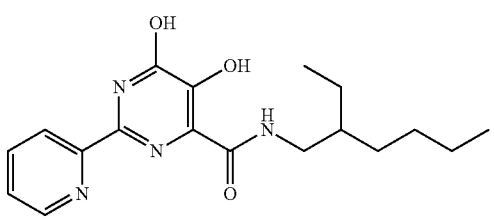 [SMILES: CCCCC(CC)CNC(=O)c1nc(-c2ccccn2)nc(O)c1O]

Prepared according to Protocol A. Avg. Purity (TWC & ELSD): 100%. ¹H NMR (400 MHz, CDCl₃) δ 12.59 (s, 1H), 11.55-11.03 (m, 1H), 8.56 (d, J=4.8, 1H), 8.17 (d, J=8.0, 1H), 7.82 (td, J=7.8, 1.7, 1H), 7.65 (s, 1H), 7.39 (ddd, J=7.6, 4.8, 1.0, 1H), 3.36 (t, J=6.3, 2H), 1.55 (dd, J=12.3, 6.2, 2H), 1.41-1.23 (m, 8H), 0.88 (dt, J=13.5, 7.2, 6H). HRMS: m/z calcd for C18H25N4O3+ [M+H]: 345.1927. found: 345.1927.

71. 5,6-dihydroxy-N-(2-hydroxyethyl)-2-(pyridin-2-yl)pyrimidine-4-carboxamide

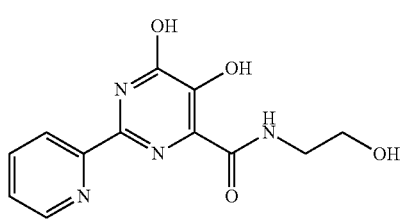 [SMILES: O=C(NCCO)c1nc(-c2ccccn2)nc(O)c1O]

Prepared according to Protocol A. Avg. Purity (TWC & ELSD): 100%. ¹H NMR (400 MHz, DMSO) δ 12.91-12.34 (m, 1H), 11.52-11.09 (m, 1H), 8.58 (d, J=4.8, 1H), 8.36 (d, J=8.0, 1H), 8.30 (s, 1H), 7.83 (td, J=7.8, 1.7, 1H), 7.43-7.38 (m, 1H), 3.72 (t, J=5.1, 2H), 3.54 (dd, J=11.0, 5.4, 2H). HRMS: m/z calcd for C12H13N4O4+ [M+H]: 277.0938. found: 277.0944.

72. 5,6-dihydroxy-N-(2-hydroxybutyl)-2-(pyridin-2-yl)pyrimidine-4-carboxamide

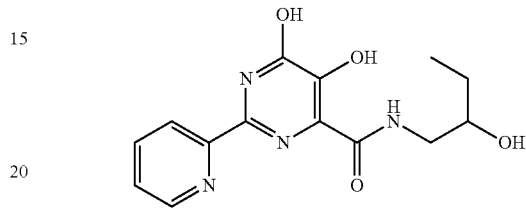

Prepared according to Protocol A. Avg. Purity (TWC & ELSD): 100%. ¹H NMR (400 MHz, DMSO) δ 12.93-12.60 (br s, 1H), 11.73-11.49 (br s, 1H), 8.61 (d, J=4.4, 1H), 8.51-8.4 m, 2H), 7.86 (t, J=6.9, 1H), 7.43 (dd, J=7.2, 5.3, 1H), 3.66-3.48 (m, 2H), 3.24 (dd, J=13.5, 5.5, 1H), 1.46 (dt, J=13.8, 6.0, 2H), 0.98-0.85 (m, 3H). HRMS: m/z calcd for C14H17N4O4+ [M+H]: 305.1251. found: 305.1246.

73. 5,6-dihydroxy-2-(pyridin-2-yl)pyrimidin-4-yl)(piperidin-1-yl)methanone

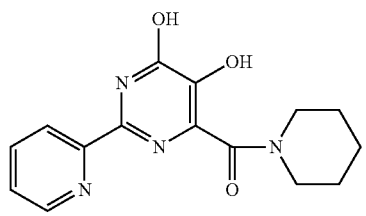 [SMILES: O=C(c1nc(-c2ccccn2)nc(O)c1O)N1CCCCC1]

Prepared according to Protocol A. Avg. Purity (TWC & ELSD): 98.2%. ¹H NMR (400 MHz, CDCl₃) δ 11.13 (s, 1H), 8.60 (d, J=3.8, 1H), 8.20 (d, J=7.2, 1H), 7.84 (m, 1H), 7.41 (m, 4.7, 1H), 3.86 (s, 4H), 1.8-1.5 (m, 6H). HRMS: m/z calcd for C15H17N4O3+ [M+H]: 301.1301. found: 301.1299.

74. 5,6-dihydroxy-N-(4-hydroxyphenethyl)-2-(pyridin-2-yl)pyrimidine-4-carboxamide

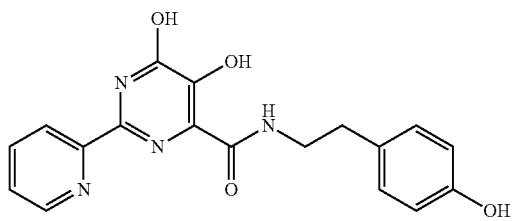 [SMILES: O=C(NCCc1ccc(O)cc1)c1nc(-c2ccccn2)nc(O)c1O]

Prepared according to Protocol A. Avg. Purity (TWC & ELSD): 100%. ¹H NMR (400 MHz, CDCl₃) δ 12.48 (s, 1H), 11.02 (s, 1H), 8.54 (d, J=4.9, 1H), 7.98 (d, J=8.0, 1H), 7.82 (t, J=7.8, 1H), 7.63 (m, 1H), 7.39-7.35 (m, 1H), 7.10 (d, J=8.3, 2H), 6.78 (d, J=8.4, 2H), 3.63 (dd, J=13.1, 6.6, 2H), 2.84 (t, J=6.8, 2H). HRMS: m/z calcd for C18H17N4O4+ [M+H]: 353.1251. found: 353.1252.

75. N-(furan-2-ylmethyl)-5,6-dihydroxy-2-(pyridin-2-yl)pyrimidine-4-carboxamide

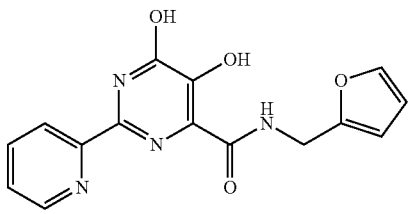 [SMILES: O=C(NCc1ccco1)c1nc(-c2ccccn2)nc(O)c1O]

Prepared according to Protocol A. Avg. Purity (TWC & ELSD): 100%. ¹H NMR (400 MHz, CDCl₃) δ 12.50 (s, 1H), 11.18 (s, 1H), 8.70-8.61 (m, 1H), 8.30 (d, J=8.0, 1H), 8.00 (m, 1H), 7.91 (td, J=7.8, 1.7, 1H), 7.51-7.44 (m, 2H), 6.40 (dt, J=8.0, 2.5, 2H), 4.70 (d, J=6.0, 2H). HRMS: m/z calcd for C15H13N4O4+ [M+H]: 313.0938. found: 313.0946.

76. N-(3,4-dimethoxybenzyl)-5,6-dihydroxy-2-(pyridin-2-yl)pyrimidine-4-carboxamide

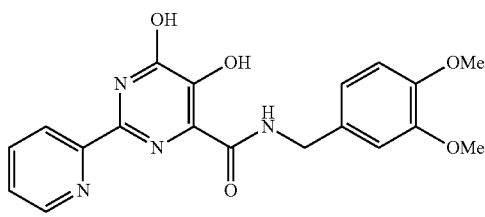 [SMILES: COc1ccc(CNC(=O)c2nc(-c3ccccn3)nc(O)c2O)cc1OC]

Prepared according to Protocol A. Avg. Purity (TWC & ELSD): 100%. ¹H NMR (400 MHz, CDCl₃) δ 12.57 (s, 1H), 11.11 (s, 1H), 8.54 (s, 1H), 8.15 (m, 1H), 7.9-7.70 (m, 2H), 7.4-7.3 (m, 1H), 6.84 (m, 3H), 4.54 (s, 2H), 3.82 (s, 6H). HRMS: m/z calcd for C19H19N4O5+ [M+H]: 383.1356. found: 383.1352.

77. N-(benzyloxy)-5,6-dihydroxy-2-(pyridin-2-yl)pyrimidine-4-carboxamide

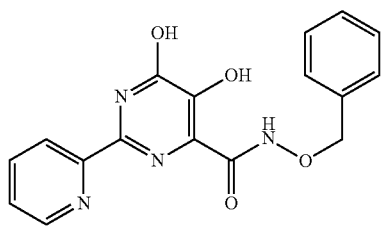 [SMILES: O=C(NOCc1ccccc1)c1nc(-c2ccccn2)nc(O)c1O]

Prepared according to Protocol A. Avg. Purity (TWC & ELSD): 100%. ¹H NMR (400 MHz, CDCl₃ and DMSO-d6) δ 12.09 (m, 2H), 11.67 (s, 1H), 8.51 (d, J=7.8, 1H), 8.44 (d, J=4.1, 1H), 7.70 (dd, J=7.8, 1.7, 1H), 7.28 (m, 3H), 7.21-7.13 (m, 3H), 4.82 (s, 2H). HRMS: m/z calcd for C17H15N4O4+ [M+H]: 339.1094. found: 339.1093.

78. 5,6-dihydroxy-2-(pyridin-2-yl)-N-(thiophen-3-ylmethyl)pyrimidine-4-carboxamide

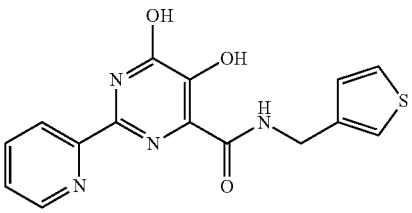 [SMILES: O=C(NCc1ccsc1)c1nc(-c2ccccn2)nc(O)c1O]

Prepared according to Protocol A. Avg. Purity (TWC & ELSD): 100%. ¹H NMR (400 MHz, CDCl₃) δ 12.52 (s, 1H), 11.09 (s, 1H), 8.55 (d, J=4.8, 1H), 8.18 (d, J=7.9, 1H), 7.90 (m, 1H), 7.79 (td, J=7.7, 1.5, 1H), 7.37 (dd, J=7.5, 4.8, 1H), 7.30 (dd, J=5.0, 3.0, 1H), 7.2 (m, 1H), 7.06 (dd, J=5.0, 1.0, 1H), 4.62 (d, J=6.2, 2H). HRMS: m/z calcd for C15H13N4O3S+ [M+H]: 329.0709. found: 329.0710.

79. 5,6-dihydroxy-N-(4-methoxyphenyl)-2-(pyridin-2-yl)pyrimidine-4-carboxamide

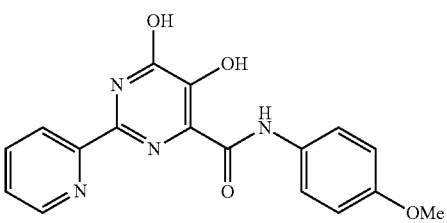 [SMILES: COc1ccc(NC(=O)c2nc(-c3ccccn3)nc(O)c2O)cc1]

Prepared according to Protocol A. Avg. Purity (TWC & ELSD): 96.8%. ¹H NMR (400 MHz, CDCl₃) δ 12.41 (s, 1H), 11.13 (s, 1H), 9.32 (s, 1H), 8.59 (d, J=4.8, 1H), 8.28 (d, J=7.9, 1H), 7.87 (td, J=7.8, 1.6, 1H), 7.56 (d, J=9.0, 2H), 7.45-7.39 (m, 1H), 6.90 (d, J=9.0, 2H), 3.77 (s, 3H). HRMS: m/z calcd for C17H15N4O4+ [M+H]: 339.1094. found: 339.1098.

80. Methyl 3-(5,6-dihydroxy-2-(pyridin-2-yl)pyrimidine-4-carboxamido)benzoate

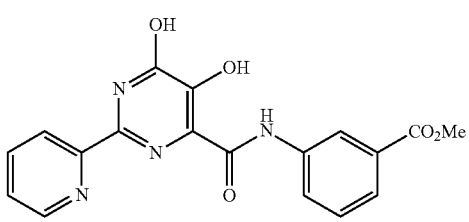 [SMILES: COC(=O)c1cccc(NC(=O)c2nc(-c3ccccn3)nc(O)c2O)c1]

Prepared according to Protocol A. Avg. Purity (TWC & ELSD): 86.7%. ¹H NMR (400 MHz, CDCl₃) δ 12.27 (s, 1H), 11.26 (s, 1H), 9.63 (s, 1H), 8.70 (d, J=4.8, 1H), 8.42 (d, J=8.1, 1H), 8.24 (s, 1H), 8.18 (d, J=8.1, 1H), 8.00 (m, 1H), 7.93 (d, J=7.8, 1H), 7.59-7.50 (m, 2H), 4.00 (s, 3H). HRMS: m/z calcd for C18H15N4O5+ [M+H]: 367.1043. found: 367.1038.

81. 5,6-dihydroxy-N-phenyl-2-(pyridin-2-yl)pyrimidine-4-carboxamide

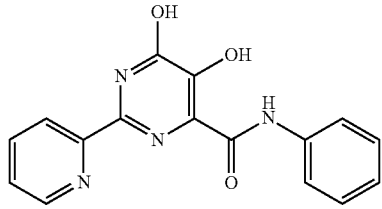 [SMILES: O=C(Nc1ccccc1)c1nc(-c2ccccn2)nc(O)c1O]

Prepared according to Protocol A. Avg. Purity (TWC & ELSD): 97.9%. $^1$H NMR (400 MHz, CDCl$_3$) δ 12.33 (s, 1H), 11.14 (s, 1H), 9.42 (s, 1H), 8.59 (d, J=4.8, 1H), 8.28 (d, J=7.9, 1H), 7.87 (td, J=7.8, 1.7, 1H), 7.67-7.62 (m, 2H), 7.42 (ddd, J=7.6, 4.8, 1.1, 1H), 7.43 (m, 1H), 7.37 (t, J=8.0, 2H), 7.16 (m, 1H). HRMS: m/z calcd for C16H13N4O3+ [M+H]: 309.0988. found: 309.0984.

82. N-(2-(1H-indol-3-yl)ethyl)-5,6-dihydroxy-2-(pyridin-2-yl)pyrimidine-4-carboxamide

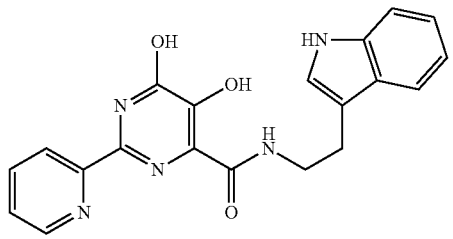 [SMILES: O=C(NCCc1c[nH]c2ccccc12)c1nc(-c2ccccn2)nc(O)c1O]

Prepared according to Protocol A. Avg. Purity (TWC & ELSD): 100%. $^1$H NMR (400 MHz, CDCl$_3$) δ 12.71 (s, 1H), 11.11 (s, 1H), 8.60 (d, J=4.8, 1H), 8.17 (s, 1H), 7.84-7.69 (m, 4H), 7.49-7.41 (m, 2H), 7.24 (m, 1H), 7.16 (dd, J=13.4, 5.3, 2H), 3.85 (m, 2H), 3.18 (t, J=6.7, 2H). HRMS: m/z calcd for C20H18N5O3+ [M+H]: 376.1410. found: 376.1419.

83. 5,6-dihydroxy-N-(4-methoxy-2-methylphenyl)-2-(pyridin-2-yl)pyrimidine-4-carboxamide

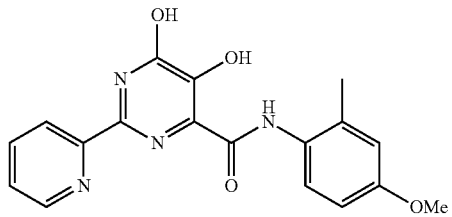 [SMILES: COc1ccc(NC(=O)c2nc(-c3ccccn3)nc(O)c2O)c(C)c1]

Prepared according to Protocol A. Avg. Purity (TWC & ELSD): 96%. $^1$H NMR (400 MHz, CDCl$_3$) δ 12.49 (s, 1H), 11.22 (s, 1H), 9.43 (s, 1H), 8.69 (d, J=4.2, 1H), 8.30 (d, J=7.9, 1H), 7.94 (m, 2H), 7.51 (ddd, J=7.6, 4.8, 1.1, 1H), 6.87 (dd, J=5.1, 2.8, 2H), 3.88-3.83 (s, 3H), 2.44 (s, 3H). HRMS: m/z calcd for C18H16N4O4+ [M+H]: 353.1251. found: 353.1254.

84. 5,6-dihydroxy-2-(pyridin-2-yl)-N-(2-(thiophen-2-yl)ethyl)pyrimidine-4-carboxamide

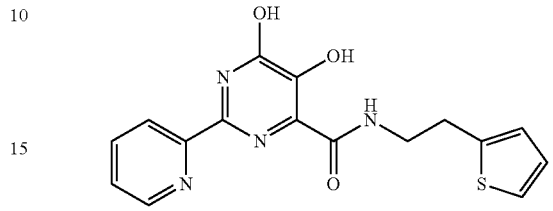

Prepared according to Protocol A. Avg. Purity (TWC & ELSD): 100%. $^1$H NMR (400 MHz, CDCl$_3$) δ 12.50 (s, 1H), 11.16 (s, 1H), 8.65 (dd, J=4.8, 0.9, 1H), 8.17 (d, J=8.0, 1H), 7.89 (m, 2H), 7.48 (ddd, J=7.6, 4.8, 1.1, 1H), 7.25 (m, 1H), 7.04 (dd, J=5.1, 3.4, 1H), 6.98 (d, J=3.4, 1H), 3.79 (q, J=6.5, 2H), 3.23 (t, J=6.6, 2H). HRMS: m/z calcd for C16H15N4O3S+ [M+H]: 343.0866. found: 343.0858.

85. N-(2,4-dimethoxybenzyl)-5,6-dihydroxy-2-(pyridin-2-yl)pyrimidine-4-carboxamide

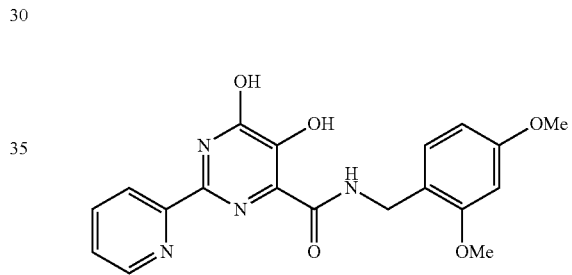

Prepared according to Protocol A. Avg. Purity (TWC & ELSD): 98.8%. $^1$H NMR (400 MHz, CDCl$_3$) δ 12.77 (s, 1H), 11.15 (s, 1H), 8.68-8.61 (m, 1H), 8.29-8.22 (m, 1H), 8.17 (m, 1H), 7.89 (td, J=7.8, 1.7, 1H), 7.46 (ddd, J=7.6, 4.8, 1.1, 1H), 7.25 (m, 1H), 6.56-6.46 (m, 2H), 4.62 (d, J=6.2, 2H), 3.94 (s, 3H), 3.84 (s, 3H). HRMS: m/z calcd for C19H18N4O5+ [M+H]: 383.1356. found: 383.1350.

86. 5,6-dihydroxy-N-(3-methoxyphenethyl)-2-(pyridin-2-yl)pyrimidine-4-carboxamide

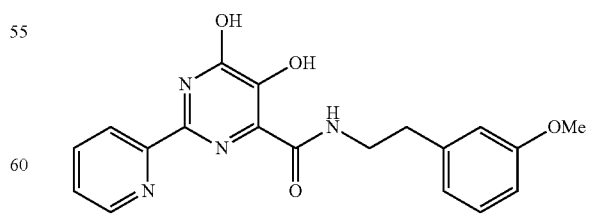

Prepared according to Protocol A. Avg. Purity (TWC & ELSD): 100%. $^1$H NMR (400 MHz, CDCl$_3$) δ 12.50 (s, 1H), 11.17 (s, 1H), 8.64 (dd, J=4.8, 0.9, 1H), 8.10 (dd, J=7.9, 0.9, 1H), 7.89 (td, J=7.8, 1.6, 1H), 7.78 (s, 1H), 7.51-7.43 (m, 1H), 7.32 (dd, J=11.7, 4.4, 1H), 6.93-6.83 (m, 3H), 3.82 (s, 3H), 3.77 (q, J=6.6, 2H), 2.98 (t, J=6.8, 2H). HRMS: m/z calcd for C19H19N4O4+ [M+H]: 367.1407. found: 367.1409.

87. 5,6-dihydroxy-2-(pyridin-2-yl)-N-O-tolylpyrimidine-4-carboxamide

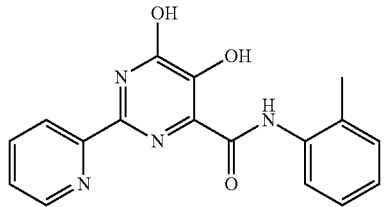 [SMILES: Cc1ccccc1NC(=O)c1nc(-c2ccccn2)nc(O)c1O]

Prepared according to Protocol A. Avg. Purity (TWC & ELSD): 97.1%. $^1$H NMR (400 MHz, CDCl$_3$) δ 12.41 (s, 1H), 11.23 (s, 1H), 9.63 (s, 1H), 8.69 (d, J=4.8, 1H), 8.30 (d, J=7.9, 1H), 8.15 (d, J=8.0, 1H), 7.96 (td, J=7.6, 1.1, 1H), 7.52 (dd, J=7.5, 4.9, 1H), 7.33 (m, 2H), 7.20 (t, J=7.5, 1H), 2.50 (s, 3H). HRMS: m/z calcd for C17H15N4O3+ [M+H]: 323.1145. found: 323.1143.

88. 5,6-dihydroxy-N-phenethyl-2-(pyridin-2-yl)pyrimidine-4-carboxamide

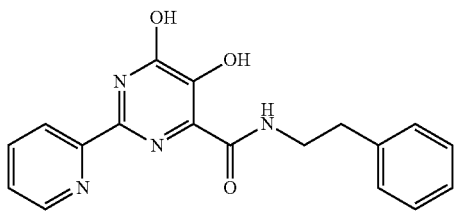 [SMILES: O=C(NCCc1ccccc1)c1nc(-c2ccccn2)nc(O)c1O]

Prepared according to Protocol A. Avg. Purity (TWC & ELSD): 100%. $^1$H NMR (400 MHz, CDCl$_3$) δ 12.37 (s, OH), 11.69-10.96 (br s, 1H), 8.66-8.62 (m, 1H), 8.10-8.07 (m, 1H), 7.88 (td, J=7.8, 1.6, 1H), 7.77 (s, 1H), 7.47 (ddd, J=7.5, 4.8, 1.1, 1H), 7.40 (dd, J=8.3, 6.8, 2H), 7.33 (t, J=6.7, 2H), 3.78 (q, J=6.7, 2H), 3.12-2.87 (m, 2H). HRMS: m/z calcd for C18H17N4O3+ [M+H]: 337.1301. found: 337.1288.

89. 5,6-dihydroxy-N-(1-phenylethyl)-2-(pyridin-2-yl)pyrimidine-4-carboxamide

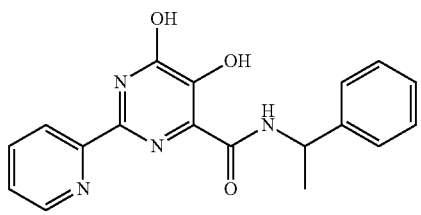 [SMILES: CC(NC(=O)c1nc(-c2ccccn2)nc(O)c1O)c1ccccc1]

Prepared according to Protocol A. Avg. Purity (TWC & ELSD): 100%. $^1$H NMR (400 MHz, CDCl$_3$) δ 12.62 (s, 1H), 11.19 (s, 1H), 8.65 (dd, J=4.8, 0.9, 1H), 8.27 (d, J=7.9, 1H), 7.91 (td, J=7.8, 1.7, 2H), 7.50-7.39 (m, 5H), 7.36 (qd, J=5.5, 2.8, 1H), 5.33 (dq, J=13.9, 6.9, 1H), 1.71 (d, J=6.9, 3H). HRMS: m/z calcd for C18H17N4O3+ [M+H]: 337.1301. found: 337.1295.

90. 5,6-dihydroxy-N-(2-morpholinophenyl)-2-(pyridin-2-yl)pyrimidine-4-carboxamide

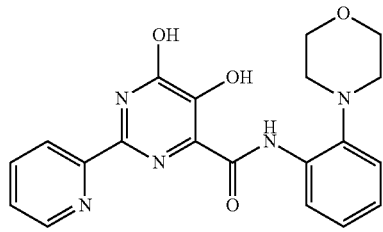 [SMILES: O=C(Nc1ccccc1N1CCOCC1)c1nc(-c2ccccn2)nc(O)c1O]

Prepared according to Protocol A. Avg. Purity (TWC & ELSD): 89.7%. $^1$H NMR (400 MHz, CDCl$_3$) δ 12.65 (s, 1H), 11.21 (s, 1H), 10.73 (s, 1H), 8.74-8.69 (m, 1H), 8.61 (d, J=7.9, 1H), 8.52-8.47 (m, 1H), 7.98 (td, J=7.8, 1.7, 1H), 7.54 (ddd, J=7.6, 4.8, 1.1, 1H), 7.35-7.2 (m, 4H), 4.06-3.93 (m, 4H), 3.09-2.92 (m, 4H). HRMS: m/z calcd for C20H20N5O4+ [M+H]: 394.1516. found: 394.1519.

91. 5,6-dihydroxy-N-(2-methoxyphenethyl)-2-(pyridin-2-yl)pyrimidine-4-carboxamide

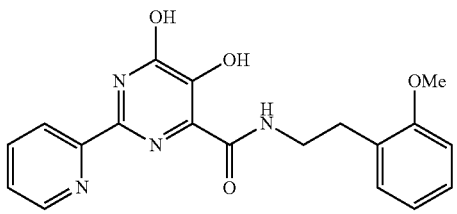 [SMILES: COc1ccccc1CCNC(=O)c1nc(-c2ccccn2)nc(O)c1O]

Prepared according to Protocol A. Avg. Purity (TWC & ELSD): 100%. $^1$H NMR (400 MHz, CDCl$_3$) δ 12.74-12.38 (m, 1H), 11.26-10.84 (m, 1H), 8.55 (d, J=4.8, 1H), 8.06 (d, J=8.0, 1H), 7.79 (td, J=7.6, 1.4, 1H), 7.69 (s, 1H), 7.41-7.35 (m, 1H), 7.25-7.1 (m, 2H), 6.84 (tt, J=14.7, 7.5, 2H), 3.78 (d, J=4.3, 3H), 3.69-3.61 (m, 2H), 2.92 (t, J=6.8, 2H), 1.50 (s, 4H). HRMS: m/z calcd for C19H19N4O4+ [M+H]: 367.1407. found: 367.1412.

92. Methyl 4-(5,6-dihydroxy-2-(pyridin-2-yl)pyrimidine-4-carboxamido)benzoate

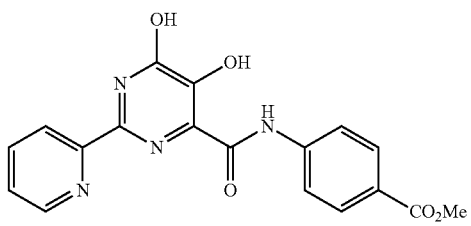 [SMILES: COC(=O)c1ccc(NC(=O)c2nc(-c3ccccn3)nc(O)c2O)cc1]

Prepared according to Protocol A. Avg. Purity (TWC & ELSD): 93.9%. $^1$H NMR (400 MHz, CDCl$_3$) δ 12.11 (s, 1H), 11.16 (s, 1H), 9.58 (s, 1H), 8.60 (d, J=4.8, 1H), 8.28 (d, J=7.9, 1H), 8.07-8.03 (m, 2H), 7.89 (td, J=7.8, 1.6, 1H), 7.74 (d, J=8.7, 2H), 7.47-7.42 (m, 1H), 4.33 (q, J=7.1, 2H), 1.35 (t, J=7.1, 3H). HRMS: m/z calcd for C19H17N4O5+ [M+H]: 381.1200. found: 381.1201.

93. 5,6-dihydroxy-N-(2-methoxyphenyl)-2-(pyridin-2-yl)pyrimidine-4-carboxamide

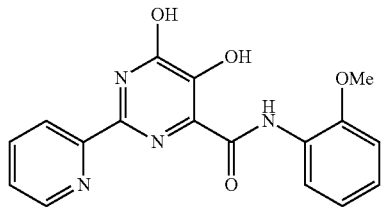

Prepared according to Protocol A. Avg. Purity (TWC & ELSD): 97.9%. ¹H NMR (400 MHz, CDCl$_3$) δ 12.34 (s, 1H), 11.10 (s, 1H), 10.20 (s, 1H), 8.62-8.57 (m, 1H), 8.38 (dd, J=8.0, 1.6, 1H), 8.31-8.25 (m, 1H), 7.87 (td, J=7.8, 1.7, 1H), 7.45-7.39 (m, 1H), 7.14-7.06 (m, 1H), 7.02-6.96 (m, 1H), 6.92 (dd, J=8.1, 1.2, 1H), 3.96 (s, 3H). HRMS: m/z calcd for C17H15N$_4$O4+ [M+H]: 339.1094. found: 339.1088.

94. 5,6-dihydroxy-2-(pyridin-2-yl)-N-p-tolylpyrimidine-4-carboxamide

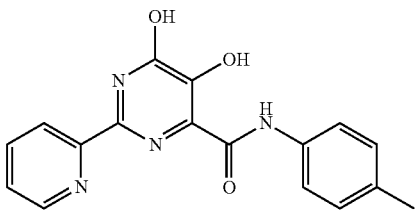 [SMILES: Cc1ccc(NC(=O)c2nc(-c3ccccn3)nc(O)c2O)cc1]

Prepared according to Protocol A. Avg. Purity (TWC & ELSD): 100%. ¹H NMR (400 MHz, CDCl$_3$) δ 12.50 (s, 1H), 11.23 (s, 1H), 9.46 (s, 1H), 8.71-8.63 (m, 1H), 8.37 (dd, J=7.9, 0.9, 1H), 7.96 (t, J=7.8, 1H), 7.62 (d, J=8.3, 2H), 7.52 (dt, J=6.0, 4.7, 1H), 7.23 (m, 2H), 2.40 (s, 3H). HRMS: m/z calcd for C17H15N4O3+ [M+H]: 323.1145. found: 323.1141.

95. 5,6-dihydroxy-2-(pyridin-2-yl)-N-M-tolylpyrimidine-4-carboxamide

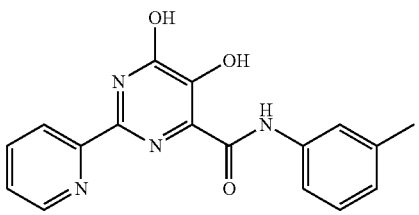 [SMILES: Cc1cccc(NC(=O)c2nc(-c3ccccn3)nc(O)c2O)c1]

Prepared according to Protocol A. Avg. Purity (TWC & ELSD): 100%. ¹H NMR (400 MHz, CDCl$_3$) δ 12.36 (s, 1H), 11.13 (s, 1H), 9.38 (s, 1H), 8.59 (dd, J=4.8, 0.9, 1H), 8.28 (d, J=7.9, 1H), 7.87 (td, J=7.8, 1.7, 1H), 7.51-7.39 (m, 2H), 7.24 (t, J=7.8, 1H), 6.98 (d, J=7.5, 1H), 2.35 (s, 3H). HRMS: m/z calcd for C17H15N4O3+ [M+H]: 323.1145. found: 323.1140.

96. 5,6-dihydroxy-N-(2-phenylpropyl)-2-(pyridin-2-yl)pyrimidine-4-carboxamide

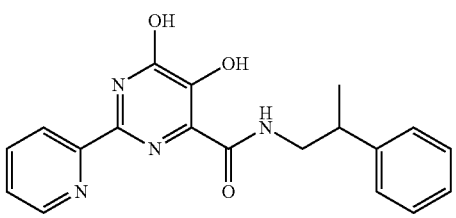 [SMILES: CC(CNC(=O)c1nc(-c2ccccn2)nc(O)c1O)c1ccccc1]

Prepared according to Protocol A. Avg. Purity (TWC & ELSD): 100%. ¹H NMR (400 MHz, CDCl$_3$) δ 12.41 (s, 1H), 11.00 (s, 1H), 8.53 (ddd, J=4.8, 1.6, 1.0, 1H), 7.82-7.72 (m, 2H), 7.52 (s, 1H), 7.4-7.3 (m, 3H), 7.26 (m, 3H), 3.79 (ddd, J=13.2, 7.5, 5.8, 1H), 3.37 (dd, J=9.0, 4.3, 1H), 3.06-2.98 (m, 1H), 1.33 (d, J=7.0, 3H). HRMS: m/z calcd for C19H19N4O3+ [M+H]: 351.1458. found: 351.1462.

97. 5,6-dihydroxy-N-(3-methyl-5-(trifluoromethyl)benzyl)-2-(pyridin-2-yl)pyrimidine-4-carboxamide

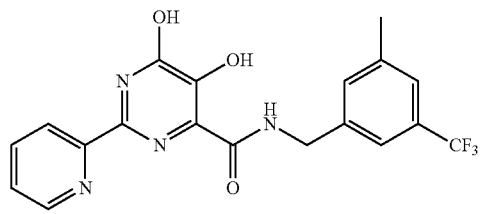 [SMILES: Cc1cc(CNC(=O)c2nc(-c3ccccn3)nc(O)c2O)cc(C(F)(F)F)c1]

Prepared according to Protocol A. Avg. Purity (TWC & ELSD): 100%. ¹H NMR (400 MHz, CDCl$_3$) δ 12.35 (s, 1H), 11.22 (s, 1H), 8.66 (d, J=4.8, 1H), 8.29 (d, J=8.0, 1H), 8.14 (s, 1H), 7.90 (td, J=7.8, 1.6, 1H), 7.51-7.44 (m, 2H), 7.33 (m, 2H), 4.76 (d, J=6.5, 2H). HRMS: m/z calcd for C18H13F4N4O3+ [M+H]: 409.0925. found: 409.0922.

98. 5,6-dihydroxy-2-(pyridin-2-yl)-N-(3-(trifluoromethyl)phenyl)pyrimidine-4-carboxamide

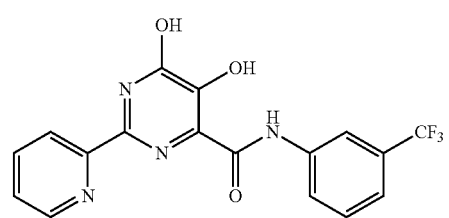 [SMILES: O=C(Nc1cccc(C(F)(F)F)c1)c1nc(-c2ccccn2)nc(O)c1O]

Prepared according to Protocol A. Avg. Purity (TWC & ELSD): 88.6%. ¹H NMR (400 MHz, CDCl$_3$) δ 12.19 (s, 1H), 11.47-11.12 (m, 1H), 9.64 (s, 1H), 8.71 (s, 1H), 8.40 (d, J=5.9, 1H), 8.00 (m, 3H), 7.64-7.49 (m, 3H). HRMS: m/z calcd for C17H1F3N4O3+ [M+H]: 377.0862. found: 377.0855.

99. N-(cyclohexylmethyl)-5,6-dihydroxy-2-(pyridin-2-yl)pyrimidine-4-carboxamide

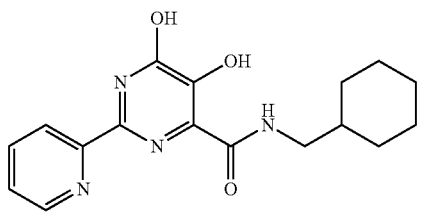 [SMILES: O=C(NCC1CCCCC1)c1nc(-c2ccccn2)nc(O)c1O]

Prepared according to Protocol A. Avg. Purity (TWC & ELSD): 100%. $^1$H NMR (400 MHz, CDCl$_3$) δ 12.79 (s, 1H), 11.44-11.04 (m, 1H), 8.66 (dd, J=4.8, 0.9, 1H), 8.30 (dd, J=8.0, 0.9, 1H), 7.93 (td, J=7.8, 1.6, 1H), 7.79 (s, 1H), 7.51-7.46 (m, 1H), 3.36 (t, J=6.6, 2H), 1.82 (m, 4H), 1.75-1.54 (m, 2H), 1.37-1.18 (m, 3H), 1.11-1.02 (m, 2H). HRMS: m/z calcd for C17H21N4O3+ [M+H]: 329.1614. found: 329.1612.

100. N-(3,5-dimethylphenyl)-5,6-dihydroxy-2-(pyridin-2-yl)pyrimidine-4-carboxamide

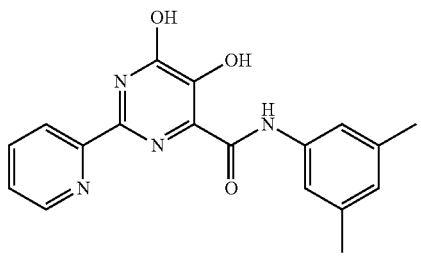 [SMILES: Cc1cc(C)cc(NC(=O)c2nc(-c3ccccn3)nc(O)c2O)c1]

Prepared according to Protocol A. Avg. Purity (TWC & ELSD): 100%. $^1$H NMR (400 MHz, CDCl$_3$) δ 12.49 (s, 1H), 11.23 (s, 1H), 9.44 (s, 1H), 8.69 (m, 1H), 8.38 (d, J=7.9, 1H), 7.97 (m, 1H), 7.53 (m, 1H), 7.37 (s, 2H), 6.90 (s, 1H), 2.40 (s, 6H). HRMS: m/z calcd for C18H17N4O3+ [M+H]: 337.1301. found: 337.1292.

101. N-benzhydryl-5,6-dihydroxy-2-(pyridin-2-yl)pyrimidine-4-carboxamide

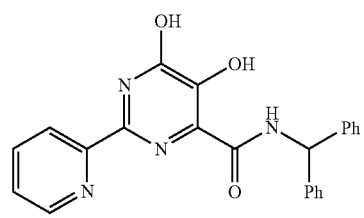 [SMILES: O=C(NC(c1ccccc1)c1ccccc1)c1nc(-c2ccccn2)nc(O)c1O]

Prepared according to Protocol A. Avg. Purity (TWC & ELSD): 98.5%. $^1$H NMR (400 MHz, CDCl$_3$) δ 12.49 (s, 1H), 11.21 (s, 1H), 8.65 (ddd, J=4.8, 1.6, 0.9, 1H), 8.32 (d, J=8.4, 1H), 8.23 (dt, J=7.9, 1.0, 1H), 7.89 (td, J=7.8, 1.7, 1H), 7.44-7.4 (m, 5H), 7.39-7.34 (m, 6H), 6.43 (d, J=8.4, 1H). HRMS: m/z calcd for C23H19N4O3+ [M+H]: 399.1458. found: 399.1465.

102. N-(2,3-dihydro-1H-inden-5-yl)-5,6-dihydroxy-2-(pyridin-2-yl)pyrimidine-4-carboxamide

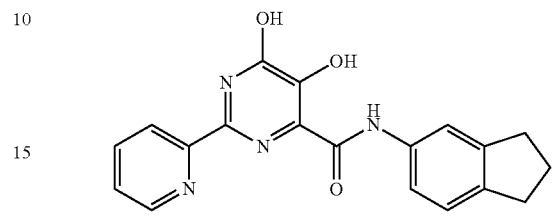

Prepared according to Protocol A. Avg. Purity (TWC & ELSD): 99.4%. $^1$H NMR (400 MHz, CDCl$_3$) δ 12.54 (s, 1H), 11.23 (s, 1H), 9.47 (s, 1H), 8.71-8.67 (m, 1H), 8.37 (d, J=7.9, 1H), 7.96 (td, J=7.8, 1.7, 1H), 7.67 (s, 1H), 7.56-7.49 (m, 1H), 7.42 (dd, J=8.0, 1.9, 1H), 2.94 (m, 4H), 2.13 (m, 2H). HRMS: m/z calcd for C19H17N4O3+ [M+H]: 349.1301. found: 349.1294.

103. N-(biphenyl-3-ylmethyl)-5,6-dihydroxy-2-(pyridin-2-yl)pyrimidine-4-carboxamide

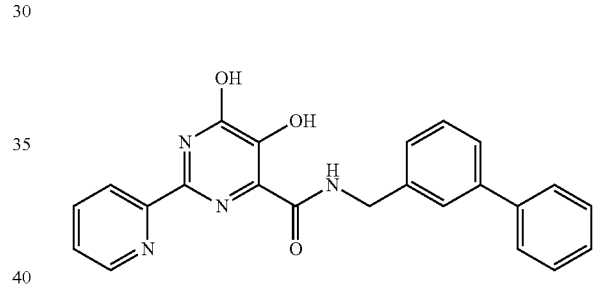

Prepared according to Protocol A. Avg. Purity (TWC & ELSD): 90.7%. $^1$H NMR (400 MHz, CDCl$_3$) δ 12.64 (s, 1H), 11.19 (s, 1H), 8.64-8.61 (m, 1H), 8.29-8.24 (m, 1H), 8.10 (s, 1H), 7.86 (td, J=7.8, 1.7, 1H), 7.64-7.56 (m, 4H), 7.50-7.35 (m, 6H), 4.78 (d, J=6.2, 2H). HRMS: m/z calcd for C23H19N4O3+ [M+H]: 399.1458. found: 399.1454.

104. 5,6-dihydroxy-N-(4-phenoxyphenyl)-2-(pyridin-2-yl)pyrimidine-4-carboxamide

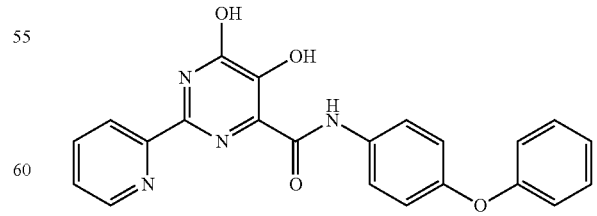

Prepared according to Protocol A. Avg. Purity (TWC & ELSD): 98.6%. $^1$H NMR (400 MHz, CDCl$_3$) δ 12.31 (s, 1H), 11.12 (s, 1H), 9.37 (s, 1H), 8.58 (ddd, J=4.8, 1.6, 0.9, 1H), 8.26 (dt, J=8.0, 1.0, 1H), 7.85 (td, J=7.8, 1.7, 1H), 7.63-7.55

(m, 2H), 7.45-7.38 (m, 1H), 7.32-7.23 (m, 2H), 7.09-6.88 (m, 5H). HRMS: m/z calcd for C22H17N4O4+ [M+H]: 401.1251. found: 401.1241.

105. N-(3,5-bis(trifluoromethyl)phenyl)-5,6-dihydroxy-2-(pyridin-2-yl)pyrimidine-4-carboxamide

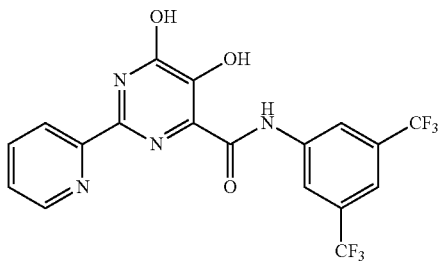 [SMILES: O=C(Nc1cc(C(F)(F)F)cc(C(F)(F)F)c1)c1nc(-c2ccccn2)nc(O)c1O]

Prepared according to Protocol A. Avg. Purity (TWC & ELSD): 99.0%. $^1$H NMR (400 MHz, CDCl$_3$) δ 12.29 (s, 1H), 11.23 (s, 1H), 8.73-8.61 (m, 1H), 8.30 (d, J=8.0, 1H), 8.20 (m, 1H), 7.93-7.85 (m, 4H), 7.48 (ddd, J=7.6, 4.8, 1.1, 1H), 4.83 (d, J=6.5, 2H). HRMS: m/z calcd for C19H13F6N4O3+ [M+H]: 459.0893. found: 459.0879.

106. N-(3-(benzyloxy)phenyl)-5,6-dihydroxy-2-(pyridin-2-yl)pyrimidine-4-carboxamide

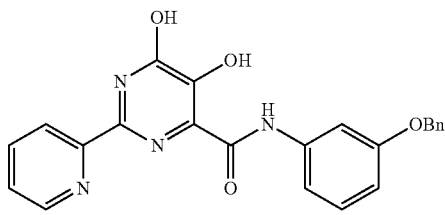 [SMILES: O=C(Nc1cccc(OCc2ccccc2)c1)c1nc(-c2ccccn2)nc(O)c1O]

Prepared according to Protocol A. Avg. Purity (TWC & ELSD): 97.8%. $^1$H NMR (400 MHz, CDCl$_3$) δ 12.30 (s, 1H), 11.13 (s, 1H), 9.41 (s, 1H), 8.62-8.55 (m, 1H), 8.26 (d, J=7.9, 1H), 7.87 (td, J=7.8, 1.7, 1H), 7.47-7.23 (m, 8H), 7.16 (s, 1H), 5.05 (s, 2H). HRMS: m/z calcd for C23H19N4O4+ [M+H]: 415.1407. found: 415.1412.

107. N-(2-(biphenyl-4-yl)ethyl)-5,6-dihydroxy-2-(pyridin-2-yl)pyrimidine-4-carboxamide

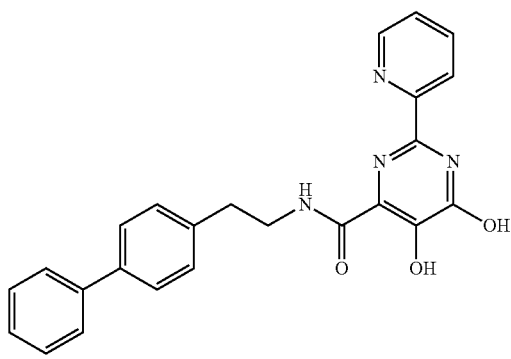 [SMILES: O=C(NCCc1ccc(-c2ccccc2)cc1)c1nc(-c2ccccn2)nc(O)c1O]

Prepared according to Protocol A. Avg. Purity (TWC & ELSD): 100%. $^1$H NMR (400 MHz, CDCl$_3$) δ 12.29-11.83 (m, 1H), 11.31-10.90 (m, 1H), 8.51 (d, J=4.8, 1H), 7.91 (d, J=7.9, 1H), 7.67 (s, 1H), 7.54 (t, J=7.5, 4H), 7.47 (td, J=7.8, 1.6, 1H), 7.39 (t, J=7.6, 2H), 7.34-7.27 (m, 4H), 3.72 (q, J=6.7, 2H), 2.95 (t, J=6.8, 2H). HRMS: m/z calcd for C24H21N4O3+ [M+H]: 413.1614. found: 413.1620.

108. N-(4-benzylphenyl)-5,6-dihydroxy-2-(pyridin-2-yl)pyrimidine-4-carboxamide

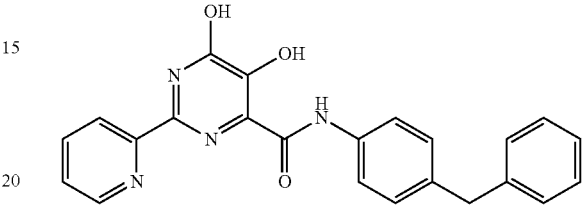

Prepared according to Protocol A. Avg. Purity (TWC & ELSD): 96.6%. $^1$H NMR (400 MHz, CDCl$_3$) δ 12.35 (s, 1H), 11.13 (s, 1H), 9.37 (s, 1H), 8.58 (d, J=4.3, 1H), 8.26 (d, J=7.9, 1H), 7.86 (td, J=7.8, 1.7, 1H), 7.55 (d, J=8.5, 2H), 7.41 (m, 1H), 7.25-7.1 (m, 7H), 3.93 (s, 2H). HRMS: m/z calcd for C23H19N4O3+ [M+H]: 399.1458. found: 399.1458.

109. N-(3-tert-butylphenyl)-5,6-dihydroxy-2-(pyridin-2-yl)pyrimidine-4-carboxamide

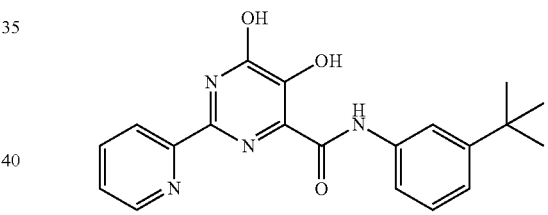

Prepared according to Protocol A. Avg. Purity (TWC & ELSD): 98.9%. $^1$H NMR (400 MHz, CDCl$_3$) δ 12.51 (s, 1H), 11.25 (s, 1H), 9.48 (s, 1H), 8.69 (d, J=4.8, 1H), 8.39 (d, J=7.9, 1H), 7.98 (td, J=7.8, 1.7, 1H), 7.73 (t, J=1.9, 1H), 7.60-7.49 (m, 2H), 7.39 (t, J=7.9, 1H), 7.27 (m, 1H), 1.39 (s, 9H). HRMS: m/z calcd for C20H21N4O3+ [M+H]: 365.1614. found: 365.1612.

110. N-(4-tert-butylphenyl)-5,6-dihydroxy-2-(pyridin-2-yl)pyrimidine-4-carboxamide

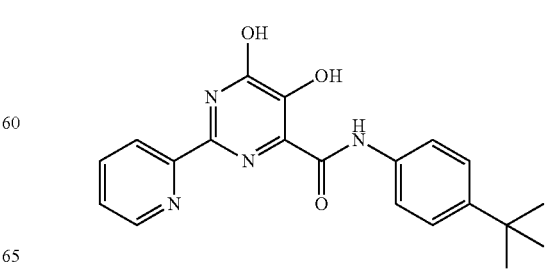

Prepared according to Protocol A. Avg. Purity (TWC & ELSD): 100%. $^1$H NMR (400 MHz, CDCl$_3$) δ 12.40 (s, 1H), 11.13 (s, 1H), 9.36 (s, 1H), 8.61-8.57 (m, 1H), 8.27 (d, J=7.9, 1H), 7.87 (td, J=7.8, 1.7, 1H), 7.57-7.51 (m, 2H), 7.45-7.34 (m, 3H), 1.31 (s, 9H). HRMS: m/z calcd for C20H21N4O3+ [M+H]: 365.1614. found: 365.1610.

111. 5,6-dihydroxy-N-(3-phenoxyphenyl)-2-(pyridin-2-yl)pyrimidine-4-carboxamide

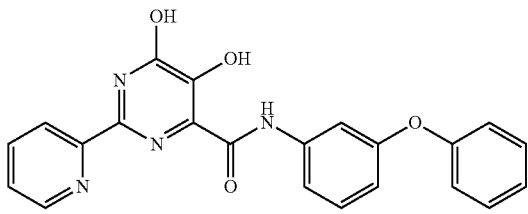 [SMILES: O=C(Nc1cccc(Oc2ccccc2)c1)c1nc(-c2ccccn2)nc(O)c1O]

Prepared according to Protocol A. Avg. Purity (TWC & ELSD): 94.9%. $^1$H NMR (400 MHz, CDCl$_3$) δ 12.32 (s, 1H), 11.23 (s, 1H), 9.50 (s, 1H), 8.68 (ddd, J=4.8, 1.6, 0.9, 1H), 8.35 (dt, J=8.0, 1.0, 1H), 7.96 (td, J=7.8, 1.7, 1H), 7.55-7.45 (m, 3H), 7.44-7.36 (m, 3H), 7.22-7.15 (m, 1H), 7.12-7.07 (m, 2H), 6.89 (ddd, J=8.2, 2.3, 1.0, 1H). HRMS: m/z calcd for C22H17N4O4+ [M+H]: 401.1251. found: 401.1251.

112. N-(2-(benzyloxy)phenyl)-5,6-dihydroxy-2-(pyridin-2-yl)pyrimidine-4-carboxamide

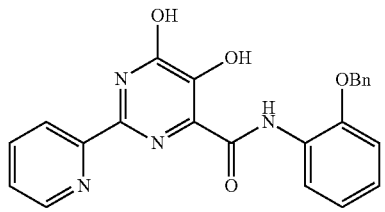 [SMILES: O=C(Nc1ccccc1OCc1ccccc1)c1nc(-c2ccccn2)nc(O)c1O]

Prepared according to Protocol A. Avg. Purity (TWC & ELSD): 99.4%. $^1$H NMR (400 MHz, CDCl$_3$) δ 12.55 (s, 1H), 11.20 (s, 1H), 10.28 (s, 1H), 8.58 (m, 2H), 7.69-7.33 (m, 9H), 7.23-7.05 (m, 3H), 5.22 (d, J=4.5, 2H). HRMS: m/z calcd for C23H19N4O4+ [M+H]: 415.1407. found: 415.1414.

113. (5,6-dihydroxy-2-M-tolylpyrimidin-4-yl)(morpholino)methanone

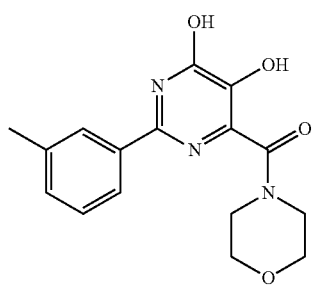 [SMILES: Cc1cccc(-c2nc(O)c(O)c(C(=O)N3CCOCC3)n2)c1]

Prepared according to Protocol A. Avg. Purity (TWC & ELSD): 100%. $^1$H NMR (400 MHz, DMSO-d$_6$) δ 12.94 (s, 1H), 10.11 (br s, 1H), 7.83 (s, 1H), 7.79 (d, J=7.5, 1H), 7.36 (m, 2H), 3.60 (m, 4H), 3.36 (m, 4H), 2.37 (s, 3H).

114. (5,6-dihydroxy-2-p-tolylpyrimidin-4-yl)(morpholino)methanone

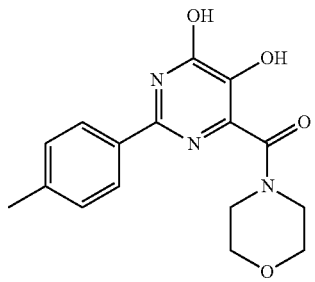 [SMILES: Cc1ccc(-c2nc(O)c(O)c(C(=O)N3CCOCC3)n2)cc1]

Prepared according to Protocol A. Avg. Purity (TWC & ELSD): 100%. $^1$H NMR (400 MHz, CDCl$_3$) δ 11.34 (br s, 2H), 7.83 (d, J=8.0, 2H), 7.35 (d, J=8.0, 2H), 4.30 (s, 1H), 3.84 (m, 4H), 3.52 (s, 1H), 3.31-3.08 (m, 1H), 2.45 (s, 3H).

115. 5,6-dihydroxy-N-(1-phenylethyl)-2-(3-(trifluoromethyl)phenyl)pyrimidine-4-carboxamide

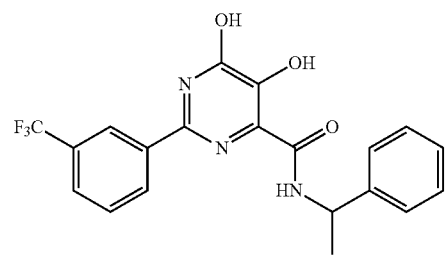 [SMILES: CC(NC(=O)c1nc(-c2cccc(C(F)(F)F)c2)nc(O)c1O)c1ccccc1]

Prepared according to Protocol A. Avg. Purity (TWC & ELSD): 100%. $^1$H NMR (400 MHz, CDCl$_3$) δ 12.51 (s, 2H), 8.32 (s, 1H), 8.26 (d, J=7.6, 1H), 7.99 (d, J=8.1, 1H), 7.83 (d, J=7.7, 1H), 7.74 (t, J=7.8, 1H), 7.43 (d, J=4.5, 3H), 7.35 (dq, J=8.6, 4.3, 1H), 5.35-5.24 (m, 1H), 1.70 (d, J=6.9, 3H).

116. 5,6-dihydroxy-N-phenyl-2-(3-(trifluoromethyl)phenyl)pyrimidine-4-carboxamide

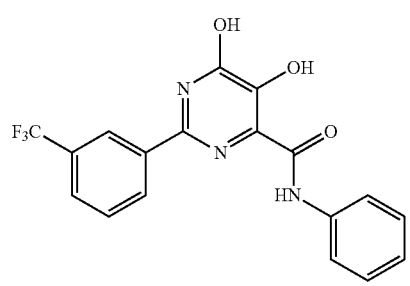 [SMILES: O=C(Nc1ccccc1)c1nc(-c2cccc(C(F)(F)F)c2)nc(O)c1O]

Prepared according to Protocol A. Avg. Purity (TWC & ELSD): 100%. $^1$H NMR (400 MHz, CDCl$_3$ and DMSO-d$_6$) δ

8.23 (s, 1H), 8.14 (s, 1H), 7.79 (s, 1H), 7.66 (d, J=7.5, 3H), 7.43-7.36 (m, 2H), 7.21 (d, J=7.5, 1H).

117. 5,6-dihydroxy-N-isopentyl-2-M-tolylpyrimidine-4-carboxamide

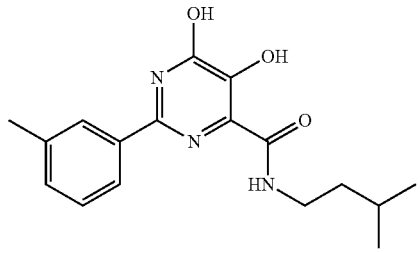 [SMILES: Cc1cccc(-c2nc(O)c(O)c(C(=O)NCCC(C)C)n2)c1]

Prepared according to Protocol A. Avg. Purity (TWC & ELSD): 100%. ¹H NMR (400 MHz, CDCl₃) δ 12.50 (s, 1H), 11.85-11.55 (m, 1H), 7.86-7.77 (m, 2H), 7.46 (t, J=7.7, 1H), 7.38 (d, J=7.6, 1H), 3.52 (dd, J=15.0, 6.2, 2H), 2.50 (s, 3H), 1.73 (td, J=13.3, 6.7, 1H), 1.59 (dd, J=14.8, 7.1, 2H), 1.01 (d, J=6.6, 6H).

118. 5,6-dihydroxy-N-isopentyl-2-p-tolylpyrimidine-4-carboxamide

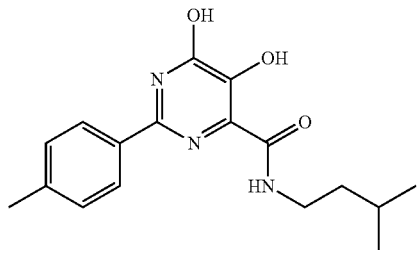 [SMILES: Cc1ccc(-c2nc(O)c(O)c(C(=O)NCCC(C)C)n2)cc1]

Prepared according to Protocol A. Avg. Purity (TWC & ELSD): 100%. ¹H NMR (400 MHz, CDCl₃) δ 12.48 (s, 1H), 11.71 (br s, 1H), 7.90 (d, J=8.3, 2H), 7.80 (t, J=5.9, 1H), 7.37 (d, J=8.0, 2H), 3.55-3.46 (m, 2H), 2.46 (s, 3H), 1.72 (td, J=13.3, 6.6, 1H), 1.63-1.53 (m, 2H), 1.01 (d, J=6.6, 6H).

119. 5,6-dihydroxy-N-(2-methoxyethyl)-2-M-tolylpyrimidine-4-carboxamide

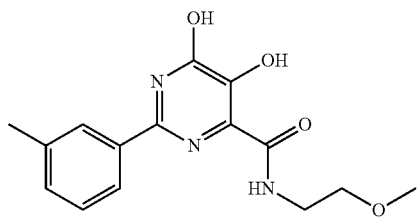

Prepared according to Protocol A. Avg. Purity (TWC & ELSD): 100%. ¹H NMR (400 MHz, CDCl₃) δ 12.38 (s, 1H), 11.42 (br s, 1H), 8.13 (s, 1H), 7.83 (s, 1H), 7.79 (d, J=7.8, 1H), 7.46 (t, J=7.7, 1H), 7.38 (d, J=7.6, 1H), 3.69 (m, 2H), 3.63 (m, 2H), 3.45 (s, 3H), 2.50 (s, 3H).

120. 5,6-dihydroxy-N-(2-methoxyethyl)-2-p-tolylpyrimidine-4-carboxamide

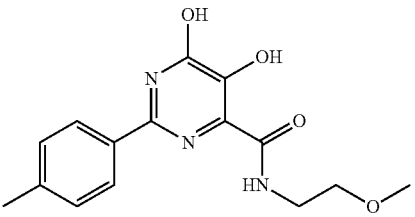

Prepared according to Protocol A. Avg. Purity (TWC & ELSD): 100%. ¹H NMR (400 MHz, CDCl₃) δ 12.37 (s, 1H), 11.73-11.29 (br s, 1H), 8.12 (s, 1H), 7.90 (d, J=8.1, 2H), 7.37 (d, J=7.9, 2H), 3.69 (dd, J=10.4, 5.6, 2H), 3.62 (t, J=4.8, 2H), 3.45 (s, 3H), 2.46 (s, 3H).

121. (5,6-dihydroxy-2-p-tolylpyrimidin-4-yl)(4-methylpiperazin-1-yl)methanone

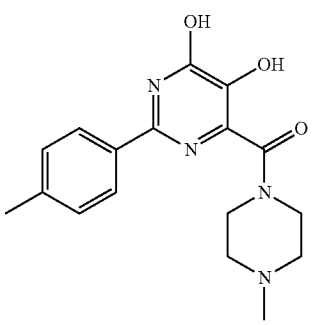 [SMILES: Cc1ccc(-c2nc(O)c(O)c(C(=O)N3CCN(C)CC3)n2)cc1]

Prepared according to Protocol A. Avg. Purity (TWC & ELSD): 95.6%. ¹H NMR (400 MHz, CDCl₃) δ 7.84 (d, J=8.1, 2H), 7.34 (d, J=7.9, 2H), 4.24 (s, 2H), 3.87 (s, 2H), 2.62-2.51 (m, 4H), 2.44 (s, 3H), 2.38 (s, 3H).

122. N-benzyl-5,6-dihydroxy-2-M-tolylpyrimidine-4-carboxamide

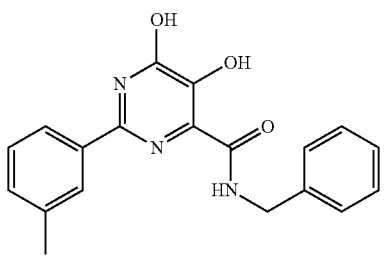 [SMILES: Cc1cccc(-c2nc(O)c(O)c(C(=O)NCc3ccccc3)n2)c1]

Prepared according to Protocol A. Avg. Purity (TWC & ELSD): 100%. ¹H NMR (400 MHz, CDCl₃) δ 12.43-12.13 (s, 1H), 11.64-11.10 (br s, 1H), 8.06 (s, 1H), 7.73-7.62 (m, 2H), 7.38-7.22 (m, 7H), 4.61 (d, J=6.3, 2H), 2.38 (s, 3H).

123. N-benzyl-5,6-dihydroxy-2-(3-(trifluoromethyl)phenyl)pyrimidine-4-carboxamide

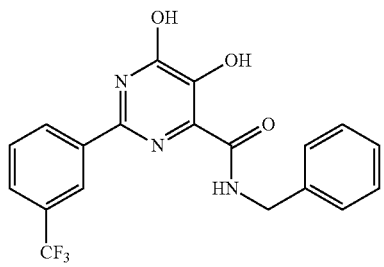 [SMILES: O=C(NCc1ccccc1)c1nc(-c2cccc(C(F)(F)F)c2)nc(O)c1O]

Prepared according to Protocol A. Avg. Purity (TWC & ELSD): 100%. $^1$H NMR (400 MHz, CDCl$_3$ and DMSO-d$_6$) δ 8.17 (s, 1H), 8.09 (d, J=8.0, 1H), 7.75 (d, J=7.8, 1H), 7.61 (t, J=7.9, 1H), 7.39-7.29 (m, 5H), 4.64 (s, 2H).

124. 5,6-dihydroxy-N-propyl-2-M-tolylpyrimidine-4-carboxamide

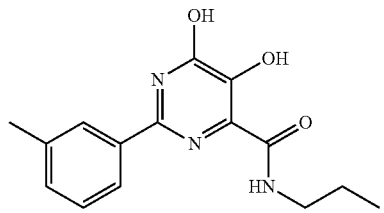 [SMILES: CCCNC(=O)c1nc(-c2cccc(C)c2)nc(O)c1O]

Prepared according to Protocol A. Avg. Purity (TWC & ELSD): 97.8%. $^1$H NMR (400 MHz, CDCl$_3$) δ 12.50 (s, 1H), 11.74 (s, 1H), 7.83 (m, 3H), 7.46 (t, J=7.6, 1H), 7.38 (d, J=7.6, 1H), 3.47 (dd, J=14.1, 6.5, 2H), 2.50 (s, 3H), 1.79-1.66 (m, 2H), 1.05 (t, J=7.4, 3H).

125. 5,6-dihydroxy-N-(pyridin-4-ylmethyl)-2-M-tolylpyrimidine-4-carboxamide

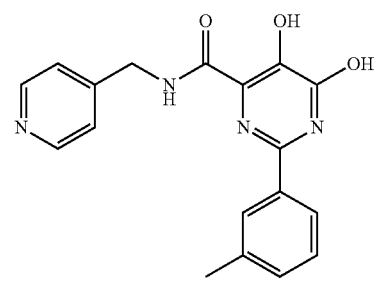 [SMILES: Cc1cccc(-c2nc(O)c(O)c(C(=O)NCc3ccncc3)n2)c1]

Prepared according to Protocol A. Avg. Purity (TWC & ELSD): 98.5%. $^1$H NMR (400 MHz, CDCl$_3$) δ 8.44 (s, 2H), 7.62 (d, J=10.2, 2H), 7.28 (m, 5H), 4.59 (s, 2H), 2.35 (s, 3H).

126. 5,6-dihydroxy-N-(pyridin-4-ylmethyl)-2-(3-(trifluoromethyl)phenyl)pyrimidine-4-carboxamide

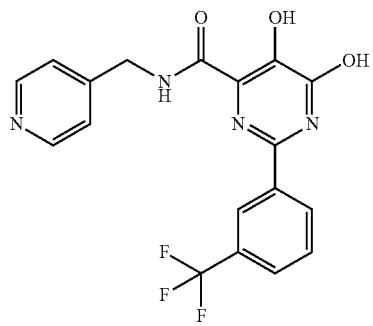 [SMILES: O=C(NCc1ccncc1)c1nc(-c2cccc(C(F)(F)F)c2)nc(O)c1O]

Prepared according to Protocol A. Avg. Purity (TWC & ELSD): 100%. $^1$H NMR (400 MHz, CDCl$_3$ and DMSO-d$_6$) δ 8.40 (dd, J=4.6, 1.6, 2H), 8.16 (s, 1H), 8.06 (d, J=8.0, 1H), 7.68 (d, J=7.8, 1H), 7.55 (t, J=7.9, 1H), 7.23 (d, J=6.1, 2H), 4.57 (s, 2H).

127. N-(cyclopropylmethyl)-5,6-dihydroxy-2-M-tolylpyrimidine-4-carboxamide

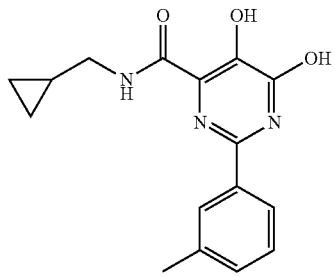 [SMILES: Cc1cccc(-c2nc(O)c(O)c(C(=O)NCC3CC3)n2)c1]

Prepared according to Protocol A. Avg. Purity (TWC & ELSD): 100%. $^1$H NMR (400 MHz, CDCl$_3$) δ 12.50 (s, 1H), 11.58 (s, 1H), 7.92 (s, 1H), 7.86-7.78 (m, 2H), 7.47 (t, J=7.7, 1H), 7.39 (d, J=7.6, 1H), 3.41-3.31 (m, 2H), 2.51 (s, 3H), 1.14 (m, 1H), 0.68-0.58 (m, 2H), 0.36 (m, 2H).

128. N-(cyclopropylmethyl)-5,6-dihydroxy-2-p-tolylpyrimidine-4-carboxamide

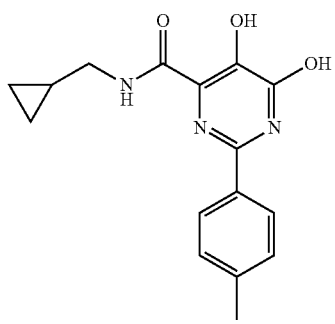 [SMILES: Cc1ccc(-c2nc(O)c(O)c(C(=O)NCC3CC3)n2)cc1]

Prepared according to Protocol A. Avg. Purity (TWC & ELSD): 100%. $^1$H NMR (400 MHz, CDCl$_3$) δ 12.34 (s, 1H), 11.53 (s, 1H), 7.77 (d, J=8.2, 3H), 7.23 (d, J=8.0, 2H), 3.24-3.16 (m, 2H), 2.31 (s, 3H), 1.04-0.91 (m, 1H), 0.53-0.44 (m, 2H), 0.21 (q, J=4.7, 2H).

129. N-(furan-2-ylmethyl)-5,6-dihydroxy-2-M-tolylpyrimidine-4-carboxamide

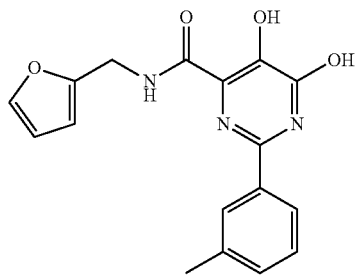 [SMILES: Cc1cccc(-c2nc(O)c(O)c(C(=O)NCc3ccco3)n2)c1]

Prepared according to Protocol A. Avg. Purity (TWC & ELSD): 100%. $^1$H NMR (400 MHz, CDCl$_3$) δ 7.65 (d, J=8.6, 2H), 7.39-7.29 (m, 3H), 6.32 (dt, J=8.0, 2.5, 2H), 4.61 (s, 2H), 3.35 (dt, J=3.3, 1.6, 1H), 2.42 (s, 3H).

130. N-(furan-2-ylmethyl)-5,6-dihydroxy-2-(3-(trifluoromethyl)phenyl)pyrimidine-4-carboxamide

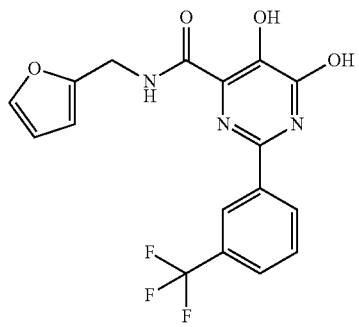 [SMILES: O=C(NCc1ccco1)c1nc(-c2cccc(C(F)(F)F)c2)nc(O)c1O]

Prepared according to Protocol A. Avg. Purity (TWC & ELSD): 100%. $^1$H NMR (400 MHz, CDCl$_3$ and DMSO-d$_6$) δ 8.18 (s, 1H), 8.10 (d, J=8.1, 1H), 7.76 (d, J=8.0, 1H), 7.63 (t, J=7.7, 1H), 7.38 (d, J=1.0, 1H), 6.36-6.28 (m, 2H), 4.62 (s, 2H).

131. 5,6-dihydroxy-N-morpholino-2-M-tolylpyrimidine-4-carboxamide

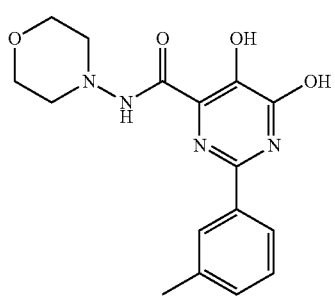 [SMILES: Cc1cccc(-c2nc(O)c(O)c(C(=O)NN3CCOCC3)n2)c1]

Prepared according to Protocol A. Avg. Purity (TWC & ELSD): 95.1%. $^1$H NMR (400 MHz, CDCl$_3$) δ 12.13 (s, 1H), 11.68-11.18 (br s, 1H), 8.52 (s, 1H), 7.77 (d, J=9.7, 2H), 7.47 (t, J=7.6, 1H), 7.40 (d, J=7.5, 1H), 3.97-3.87 (m, 4H), 3.11-3.00 (m, 4H), 2.57-2.46 (m, 3H).

132. 5,6-dihydroxy-N-(1-phenylethyl)-2-M-tolylpyrimidine-4-carboxamide

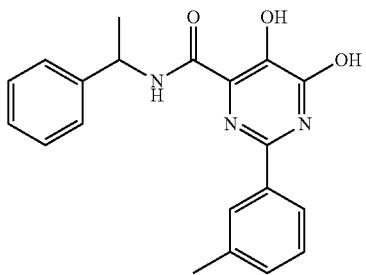 [SMILES: Cc1cccc(-c2nc(O)c(O)c(C(=O)NC(C)c3ccccc3)n2)c1]

Prepared according to Protocol A. Avg. Purity (TWC & ELSD): 99.0%. $^1$H NMR (400 MHz, CDCl$_3$) δ 12.38 (s, 1H), 11.41 (s, 1H), 8.04 (d, J=8.4, 1H), 7.76 (d, J=9.9, 2H), 7.48-7.30 (m, 6H), 5.44-5.21 (m, 1H), 2.46 (d, J=21.8, 3H), 1.67 (s, 3H).

133. 5,6-dihydroxy-N-(1-phenylethyl)-2-p-tolylpyrimidine-4-carboxamide

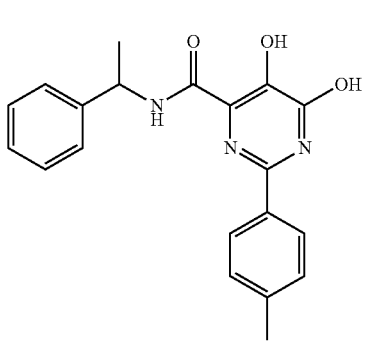 [SMILES: Cc1ccc(-c2nc(O)c(O)c(C(=O)NC(C)c3ccccc3)n2)cc1]

Prepared according to Protocol A. Avg. Purity (TWC & ELSD): 98.9%. $^1$H NMR (400 MHz, CDCl$_3$) δ 12.34 (s, 1H), 11.90 (s, 1H), 8.06 (d, J=8.3, 1H), 7.91 (t, J=12.2, 2H), 7.46-7.30 (m, 7H), 5.30 (dq, J=14.0, 7.0, 1H), 2.45 (s, 3H), 1.68 (d, J=6.9, 3H).

134. N-benzyl-5,6-dihydroxy-2-p-tolylpyrimidine-4-carboxamide

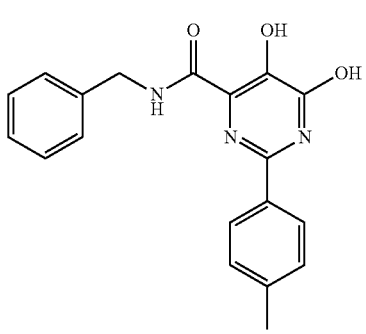 [SMILES: Cc1ccc(-c2nc(O)c(O)c(C(=O)NCc3ccccc3)n2)cc1]

Prepared according to Protocol A. Avg. Purity (TWC & ELSD): 97.2%. ¹H NMR (400 MHz, CDCl₃) δ 12.30 (s, 1H), 10.77-9.93 (m, 2H), 8.02 (s, 1H), 7.67 (d, J=8.2, 1H), 7.34-7.21 (m, 4H), 4.60 (d, J=6.2, 2H), 2.35 (s, 3H).

135. 5,6-dihydroxy-N-isopentyl-2-(3-(trifluoromethyl)phenyl)pyrimidine-4-carboxamide

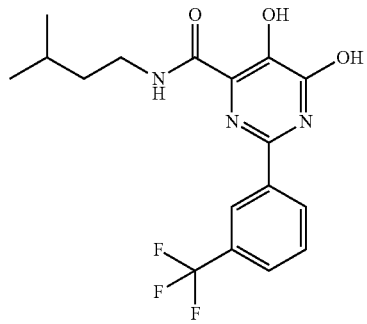 [SMILES: CC(C)CCNC(=O)c1nc(-c2cccc(C(F)(F)F)c2)nc(O)c1O]

Prepared according to Protocol A. Avg. Purity (TWC & ELSD): 100.0%. ¹H NMR (400 MHz, CDCl₃) δ 12.67 (s, 1H), 8.35 (s, 1H), 8.29 (d, J=7.9, 1H), 7.83 (d, J=7.8, 1H), 7.75 (t, J=7.6, 1H), 3.54 (dd, J=14.9, 6.2, 2H), 1.75 (tt, J=13.2, 6.6, 1H), 1.61 (dd, J=14.7, 7.1, 3H), 1.01 (t, J=8.6, 6H).

136. 5,6-dihydroxy-N-propyl-2-p-tolylpyrimidine-4-carboxamide

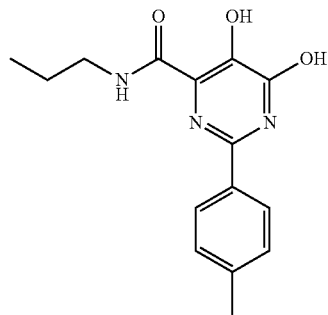 [SMILES: CCCNC(=O)c1nc(-c2ccc(C)cc2)nc(O)c1O]

Prepared according to Protocol A. Avg. Purity (TWC & ELSD): 96.1%. ¹H NMR (400 MHz, CDCl₃) δ 12.54 (s, 1H), 12.54 (s, 1H), 11.64-10.70 (br s, 1H), 7.90 (d, J=8.3, 2H), 7.40 (d, J=7.9, 2H), 3.50 (dd, J=14.1, 6.5, 2H), 2.50 (s, 3H), 1.75 (tt, J=18.1, 9.1, 5H), 1.09 (t, J=7.4, 3H).

137. N-(4-ethylcyclohexyl)-5,6-dihydroxy-2-(1-methyl-1H-imidazol-2-yl)pyrimidine-4-carboxamide

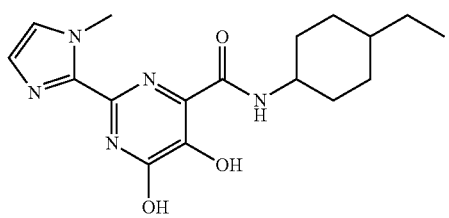 [SMILES: CCC1CCC(NC(=O)c2nc(-c3nccn3C)nc(O)c2O)CC1]

Prepared according to Protocol A. Avg. Purity (TWC & ELSD): 100%. ¹H NMR (400 MHz, DMSO) δ 12.53 (br s, 1H), 8.41-8.12 (br s, 1H), 7.46 (s, 1H), 7.10 (s, 1H), 4.03 (dd, J=16.7, 5.1 Hz, 3H), 3.66 (m, 1H), 2-0.9 (m, 8H), 0.89 (dd, J=15.6, 8.6 Hz, 3H). HRMS: m/z calcd for C17H24N5O3+ [M+H]: 346.1879. found: 346.1872.

138. 5,6-dihydroxy-2-(1-methyl-1H-imidazol-4-yl)-N-(4-methylcyclohexyl)pyrimidine-4-carboxamide

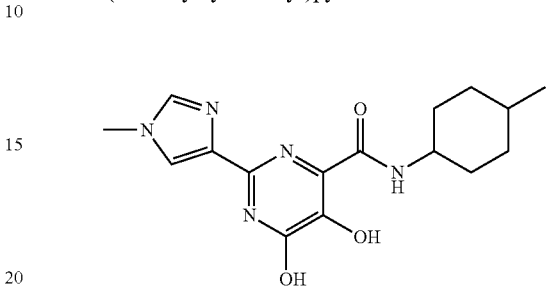

Prepared according to Protocol A. Avg. Purity (TWC & ELSD): 99.17%. ¹H NMR (400 MHz, DMSO) δ 12.53 (br d, 1H), 12.0 (br s, 1H), 8.41-8.12 (br d, 1H), 7.46 (s, 1H), 7.10 (s, 1H), 4.03 (dd, J=16.7, 5.1 Hz, 1H), 3.66 (s, 3H), 2.0-0.9 (m, 9H), 0.89 (dd, J=15.6, 8.6 Hz, 3H). HRMS: m/z calcd for C16H22N5O3+ [M+H]: 2.1723. found: 332.1721.

139. N-(4-(tert-butyl)cyclohexyl)-5,6-dihydroxy-2-(2-methyl-1H-imidazol-5-yl)pyrimidine-4-carboxamide

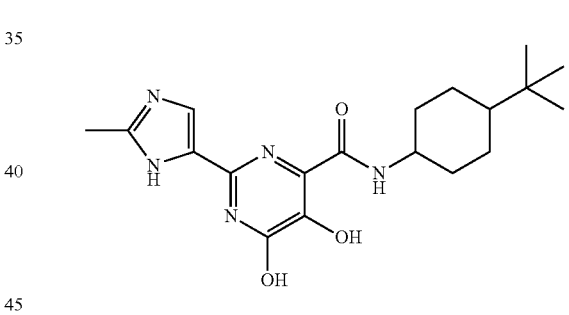

Prepared according to Protocol A. Avg. Purity (TWC & ELSD): 100%. ¹H NMR (400 MHz, DMSO) δ 12.09 (br s, 1H), 7.96-7.80 (m, 1H), 7.78 (s, 1H), 3.72 (s, 3H), 3.35 (obscured, 1H), 1.99-0.97 (m, 9H), 9 (s, 3H). HRMS: m/z calcd for C19H28N5O3+ [M+H]: 374.2192. found: 374.2191.

140. 5,6-dihydroxy-2-(2-methyl-1H-imidazol-5-yl)-N-(4-methylcyclohexyl)pyrimidine-4-carboxamide

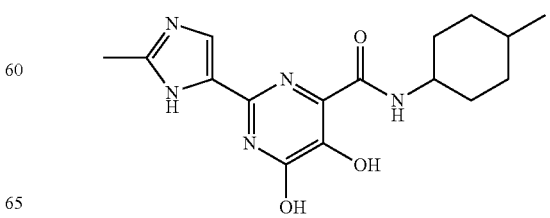

Prepared according to Protocol A. Avg. Purity (TWC & ELSD): 100%. $^1$H NMR (400 MHz, DMSO) δ 12.36 (s, 1H), 12.08 (s, 1H), 8.36 (s, 1H), 8.07 (s, 1H), 7.78 (d, J=4.7 Hz, 1H), 3.92 (s, 1H), 3.72 (d, J=29.5 Hz, 3H), 1.92-1.13 (m, 9H), 1.13-0.71 (m, 3H). HRMS: m/z calcd for C16H22N5O3+ [M+H]: 332.1723. found: 332.1721.

141. N-(4-(tert-butyl)cyclohexyl)-5,6-dihydroxy-2-(1-methyl-1H-imidazol-4-yl)pyrimidine-4-carboxamide

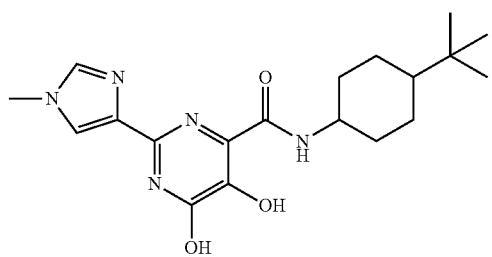 [SMILES: Cn1cnc(-c2nc(O)c(O)c(C(=O)NC3CCC(C(C)(C)C)CC3)n2)c1]

Prepared according to Protocol A. Avg. Purity (TWC & ELSD): 100%. $^1$H NMR (400 MHz, DMSO) δ 12.08 (s, 1H), 8.1 (m, 1H), 7.8 (m, 1H), 4.19-4.02 (m, 1H), 3.74 (d, J=7.8 Hz, 3H), 1.99-1.33 (m, 5H), 1.33-0.99 (m, 4H), 0.99-0.73 (m, 9H). HRMS: m/z calcd for C19H28N5O3+ [M+H]: 374.2192. found: 374.2194.

142. N-(4-ethylcyclohexyl)-5,6-dihydroxy-2-(2-methyl-1H-imidazol-5-yl)pyrimidine-4-carboxamide

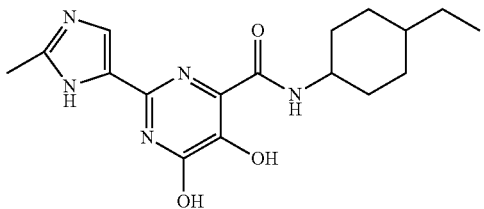 [SMILES: CCC1CCC(NC(=O)c2nc(-c3cnc(C)[nH]3)nc(O)c2O)CC1]

Prepared according to Protocol A. Avg. Purity (TWC & ELSD): 93.24%. $^1$H NMR (400 MHz, DMSO) δ 12.22 (br s, 1H), 11.82 (br s, 1H), 8.20 (br s, 1H), 7.92-7.69 (m, 1H), 7.65 (m, 1H), 3.61-3.36 (obscured, 1H), 1.74-0.72 (m, 11H), 0.72-0.46 (m, 3H). HRMS: m/z calcd for C17H24N5O3+ [M+H]: 346.1879. found: 346.1878.

143. 5,6-dihydroxy-2-(2-methyl-1H-imidazol-5-yl)-N-(3-methylcyclohexyl)pyrimidine-4-carboxamide

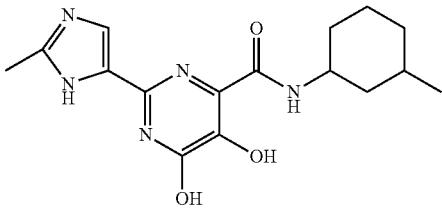

Prepared according to Protocol A. Avg. Purity (TWC & ELSD): 100%. $^1$H NMR (400 MHz, DMSO) δ 12.43 (s, 1H), 12.07 (s, 1H), 8.42 (s, 1H), 8.08 (m/z, 1H), 7.78 (s, 1H), 4.14 (s, 1H), 3.73 (s, 3H), 1.92-1.04 (m, 9H), 1.04-0.67 (m, 3H). HRMS: m/z calcd for C16H22N5O3+ [M+H]: 332.1723. found: 332.1725.

144. N-(4-ethylcyclohexyl)-5,6-dihydroxy-2-(1-methyl-1H-imidazol-4-yl)pyrimidine-4-carboxamide

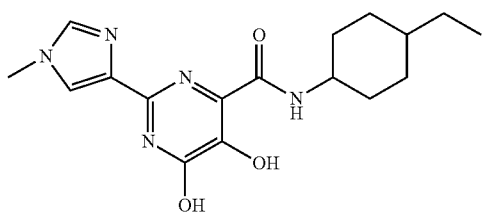 [SMILES: CCC1CCC(NC(=O)c2nc(-c3cn(C)cn3)nc(O)c2O)CC1]

Prepared according to Protocol A. Avg. Purity (TWC & ELSD): 91.88%. $^1$H NMR (400 MHz, DMSO) δ 12.21 (br s, 1H), 11.84 (br s, 1H), 8.18 (s, 1H), 7.87 (s, 1H), 7.76 (s, 1H), 7.51 (s, 1H), 3.59-3.36 (m, 3H), 1.83-0.5 (m, 14H). HRMS: m/z calcd for C17H24N5O3+ [M+H]: 346.1879. found: 346.1880.

145. (5,6-dihydroxy-2-(3-(trifluoromethyl)benzyl)pyrimidin-4-yl)(thiophen-3-yl)methanone

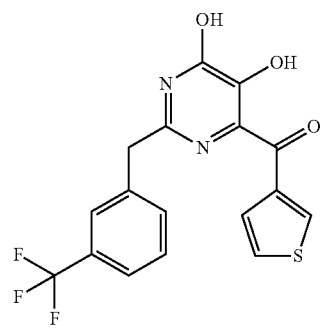 [SMILES: O=C(c1ccsc1)c1nc(Cc2cccc(C(F)(F)F)c2)nc(O)c1O]

Prepared according to Protocol A. $^1$H NMR (400 MHz, CDCl$_3$ and MeOD) δ 8.36 (s, 1H), 7.50 (d, J=4.9 Hz, 1H), 7.41 (s, 2H), 7.34-7.27 (m, 2H), 7.03 (d, J=5.0 Hz, 1H), 3.82 (s, 2H). HRMS: m/z calcd for C17H12N2O3F3S+ [M+H]: 381.0521. found: 381.0527.

146. 2-benzoyl-3-hydroxy-7,8-dihydropyrrolo[1,2-a]pyrimidin-4(6H)-one

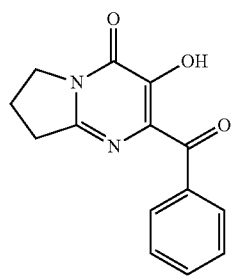 [SMILES: O=C(c1ccccc1)c1nc2n(c(=O)c1O)CCC2]

Prepared according to Protocol E. ¹H NMR (400 MHz, CDCl₃) δ 12.60 (s, 1H), 8.24 (dd, J=7.1, 6.0 Hz, 2H), 7.68-7.59 (m, 1H), 7.52 (m, 2H), 4.22 (dd, J=14.0, 6.8 Hz, 2H), 3.10 (dd, J=14.9, 7.2 Hz, 2H), 2.45-2.17 (m, 2H). HRMS: m/z calcd for C14H13N2O3+ [M+H]:257.0926. found: 257.0917.

147. 3-hydroxy-2-isobutyryl-7,8-dihydropyrrolo[1,2-a]pyrimidin-4(6H)-one

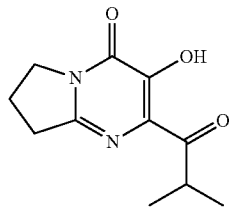 [SMILES: CC(C)C(=O)c1nc2n(c(=O)c1O)CCC2]

Prepared according to Protocol E. ¹H NMR (400 MHz, CDCl₃) δ 12.47 (s, 1H), 4.22-4.16 (m, 2H), 3.92-3.88 (m, 1H), 3.07 (t, J=7.9 Hz, 2H), 2.37-2.25 (m, 2H), 1.22 (d, J=6.9 Hz, 6H). HRMS: m/z calcd for C11H15N2O3+ [M+H]: 223.1083. found: 223.1084.

148. 3-hydroxy-2-(thiophene-3-carbonyl)-7,8-dihydropyrrolo[1,2-a]pyrimidin-4(6H)-one

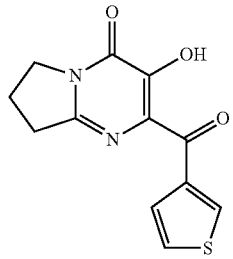 [SMILES: O=C(c1ccsc1)c1nc2n(c(=O)c1O)CCC2]

Prepared according to Protocol E. ¹H NMR (400 MHz, CDCl₃) δ 13.19 (s, 1H), 9.27 (dd, J=3.0, 1.2 Hz, 1H), 7.95 (dd, J=5.2, 1.2 Hz, 1H), 7.36 (dd, J=5.2, 3.0 Hz, 1H), 4.26-4.18 (m, 2H), 3.14 (t, J=7.9 Hz, 2H), 2.39-2.27 (m, 2H). HRMS: m/z calcd for C12H11N2O3S+ [M+H]:263.0490. found: 263.0493.

149. (5,6-dihydroxy-2-(4-methoxybenzyl)pyrimidin-4-yl)(2-methoxyphenyl)methanone

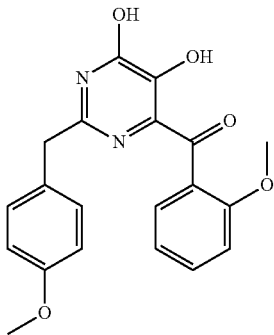 [SMILES: COc1ccc(Cc2nc(O)c(O)c(C(=O)c3ccccc3OC)n2)cc1]

Prepared according to Protocol E. ¹H NMR (400 MHz, CDCl₃) δ 12.09 (s, 1H), 11.30 (s, 1H), 7.57-7.51 (m, 1H), 7.47 (dd, J=7.6, 1.7 Hz, 1H), 7.19 (d, J=8.6 Hz, 2H), 7.08 (t, J=7.5 Hz, 1H), 7.00 (d, J=8.4 Hz, 1H), 6.85 (d, J=8.6 Hz, 2H), 3.83 (s, 2H), 3.81 (s, 3H), 3.76 (s, 3H). HRMS: m/z calcd for C20H19N2O5+ [M+H]:367.1294. found: 367.1285.

150. 3-hydroxy-2-(2-(m-tolyl)acetyl)-7,8-dihydropyrrolo[1,2-a]pyrimidin-4(6H)-one

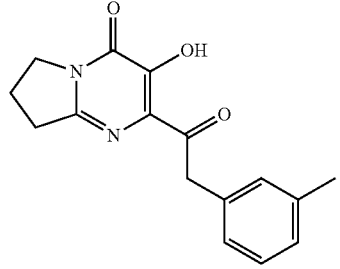 [SMILES: Cc1cccc(CC(=O)c2nc3n(c(=O)c2O)CCC3)c1]

Prepared according to Protocol E. ¹H NMR (400 MHz, CDCl₃) δ 12.18 (s, 1H), 7.29 (d, J=4.2 Hz, 2H), 7.25 (d, J=7.2 Hz, 1H), 7.13 (s, 2H), 4.37 (m, 2H), 4.23-4.14 (m, 2H), 3.16-3.06 (m, 2H), 2.41-2.24 (m, 5H). HRMS: m/z calcd for C16H17N2O3+ [M+H]:285.1239. found: 285.1242.

151. (5,6-dihydroxy-2-(4-methoxybenzyl)pyrimidin-4-yl)(3-methoxyphenyl)methanone

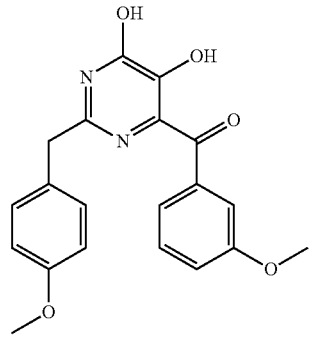 [SMILES: COc1ccc(Cc2nc(O)c(O)c(C(=O)c3cccc(OC)c3)n2)cc1]

Prepared according to Protocol E. ¹H NMR (400 MHz, CDCl₃ and MeOD) δ 7.61 (d, J=7.9 Hz, 1H), 7.54 (s, 1H), 7.16 (t, J=8.0 Hz, 1H), 7.05 (d, J=8.6 Hz, 2H), 6.98 (dd, J=8.6, 2.2 Hz, 1H), 6.71 (d, J=8.7 Hz, 2H), 3.69 (s, 2H), 3.66 (s, 3H), 3.64 (s, 3H). HRMS: m/z calcd for C20H19N2O5+ [M+H]: 367.1294. found: 367.1292.

152. (5,6-dihydroxy-2-(4-methoxybenzyl)pyrimidin-4-yl)(phenyl)methanone

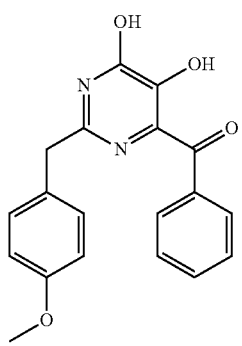 [SMILES: COc1ccc(Cc2nc(O)c(O)c(C(=O)c3ccccc3)n2)cc1]

Prepared according to Protocol E. ¹H NMR (400 MHz, CDCl₃ and MeOD) δ 7.89 (d, J=8.1 Hz, 2H), 7.36 (t, J=7.4 Hz, 1H), 7.20-7.14 (m, 2H), 6.99 (d, J=8.4 Hz, 2H), 6.65 (d, J=8.6 Hz, 2H), 3.62 (s, 2H), 3.58 (s, 3H). HRMS: m/z calcd for C19H17N2O4+ [M+H]:337.1188. found: 337.1184.

153. (5,6-dihydroxy-2-(3-methylbenzyl)pyrimidin-4-yl)(2-methoxyphenyl)methanone

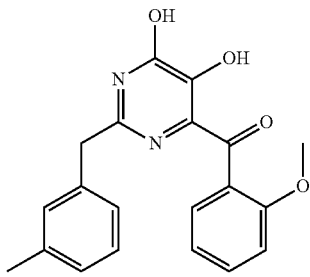

Prepared according to Protocol E. ¹H NMR (400 MHz, CDCl₃) δ 12.07 (s, 1H), 11.24 (s, 1H), 7.58-7.51 (m, 1H), 7.51-7.44 (m, 1H), 7.25-7.17 (m, 1H), 7.09 (dd, J=11.4, 6.9 Hz, 4H), 7.01 (d, J=8.1 Hz, 1H), 3.86 (s, 2H), 3.74 (d, J=4.6 Hz, 3H), 2.33 (d, J=4.4 Hz, 3H). HRMS: m/z calcd for C20H19N2O4+ [M+H]:351.1345. found: 351.1340.

154. (5,6-dihydroxy-2-(2-(trifluoromethyl)benzyl)pyrimidin-4-yl)(2-methoxyphenyl)methanone

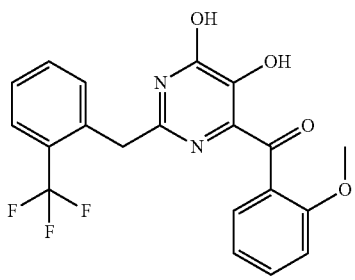 [SMILES: COc1ccccc1C(=O)c1nc(Cc2ccccc2C(F)(F)F)nc(O)c1O]

Prepared according to Protocol E. ¹H NMR (400 MHz, CDCl₃) δ 12.09 (s, 1H), 10.88 (s, 1H), 7.68 (d, J=7.1 Hz, 1H), 7.50-7.38 (m, 3H), 7.35 (dd, J=7.6, 1.7 Hz, 1H), 7.29 (s, 1H), 6.97 (t, J=7.5 Hz, 1H), 6.87 (d, J=8.4 Hz, 1H), 4.10 (s, 2H), 3.65 (s, 3H). HRMS: m/z calcd for C20H16N2O4F3+ [M+H]:405.1062. found: 405.1061.

155. (5,6-dihydroxy-2-(3-methylbenzyl)pyrimidin-4-yl)(phenyl)methanone

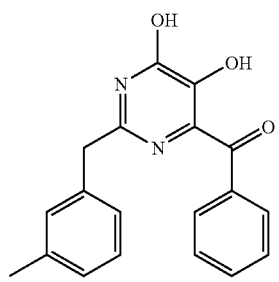 [SMILES: Cc1cccc(Cc2nc(O)c(O)c(C(=O)c3ccccc3)n2)c1]

Prepared according to Protocol E. ¹H NMR (400 MHz, CDCl₃) δ 12.73 (s, 1H), 11.49 (s, 1H), 8.27 (d, J=8.2 Hz, 2H), 7.64 (t, J=6.9 Hz, 1H), 7.47 (dd, J=10.3, 4.9 Hz, 2H), 7.27 (s, 1H), 7.21-7.13 (m, 3H), 4.01 (s, 2H), 2.37 (d, J=4.7 Hz, 3H). HRMS: m/z calcd for C19H17N2O3+ [M+H]:321.1239. found: 321.1239.

156. (5,6-dihydroxy-2-(2-(trifluoromethyl)benzyl)pyrimidin-4-yl)(phenyl)methanone

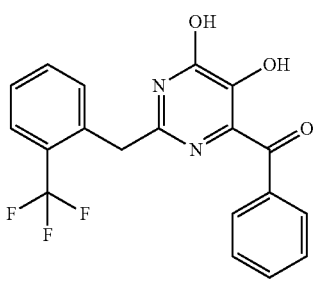 [SMILES: O=C(c1ccccc1)c1nc(Cc2ccccc2C(F)(F)F)nc(O)c1O]

Prepared according to Protocol E. ¹H NMR (400 MHz, CDCl₃) δ 12.89 (s, 1H), 11.40 (s, 1H), 8.08 (d, J=7.5 Hz, 2H), 7.78 (d, J=7.8 Hz, 1H), 7.63-7.48 (m, 3H), 7.44 (d, J=7.6 Hz, 1H), 7.33 (t, J=7.8 Hz, 2H), 4.27 (s, 2H). HRMS: m/z calcd for C19H14N2O3F3+ [M+H]:375.0957. found: 375.0960.

157. (5,6-dihydroxy-2-(naphthalen-1-ylmethyl)pyrimidin-4-yl)(3-methoxyphenyl)methanone

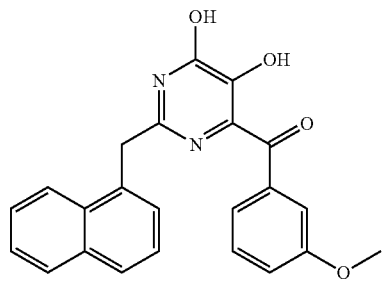 [SMILES: COc1cccc(C(=O)c2nc(Cc3cccc4ccccc34)nc(O)c2O)c1]

Prepared according to Protocol E. ¹H NMR (400 MHz, CDCl₃) δ 12.64 (s, 1H), 10.08 (s, 1H), 8.03 (s, 1H), 7.92 (d, J=6.8 Hz, 2H), 7.82 (s, 2H), 7.53 (s, 4H), 7.35 (d, J=7.5 Hz, 1H), 7.21 (d, J=5.2 Hz, 1H), 4.48 (s, 2H), 3.91 (d, J=6.6 Hz, 3H). HRMS: m/z calcd for C23H19N2O4+ [M+H]: 387.1345. found: 387.1339.

158. (5,6-dihydroxy-2-(naphthalen-1-ylmethyl)pyrimidin-4-yl)(phenyl)methanone

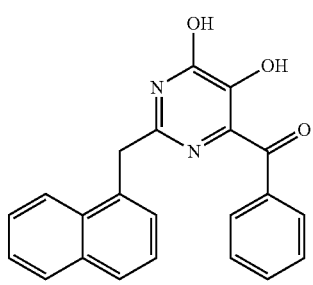 [SMILES: O=C(c1ccccc1)c1nc(Cc2cccc3ccccc23)nc(O)c1O]

Prepared according to Protocol E. ¹H NMR (400 MHz, CDCl₃) δ 12.73 (s, 1H), 11.05 (s, 1H), 8.11 (d, J=7.7 Hz, 2H), 8.04 (s, 1H), 7.93 (dd, J=16.2, 7.4 Hz, 2H), 7.64-7.45 (m, 5H), 7.40 (d, J=7.5 Hz, 2H), 4.51 (s, 2H). HRMS: m/z calcd for C22H17N2O3+ [M+H]:357.1239. found: 357.1234.

159. 1-(5,6-dihydroxy-2-(4-methoxybenzyl)pyrimidin-4-yl)-2-(M-tolyl)ethanone

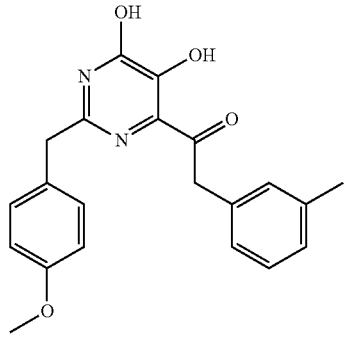 [SMILES: COc1ccc(Cc2nc(O)c(O)c(C(=O)Cc3cccc(C)c3)n2)cc1]

Prepared according to Protocol E. ¹H NMR (400 MHz, CDCl₃) δ 11.89 (s, 1H), 10.86 (s, 1H), 7.10 (dd, J=14.1, 8.6 Hz, 3H), 6.97 (d, J=6.7 Hz, 3H), 6.79-6.71 (m, 2H), 4.21 (d, J=19.1 Hz, 2H), 3.81 (s, 2H), 3.67 (d, J=2.7 Hz, 3H), 2.22-2.10 (m, 3H). HRMS: m/z calcd for C21H21N2O4+ [M+H]: 365.1501. found: 365.1493.

160. 1-(5,6-dihydroxy-2-(2-(trifluoromethyl)benzyl)pyrimidin-4-yl)-2-(m-tolyl)ethanone

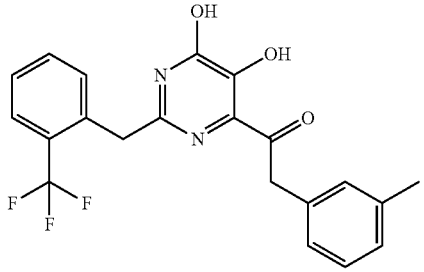 [SMILES: Cc1cccc(CC(=O)c2nc(Cc3ccccc3C(F)(F)F)nc(O)c2O)c1]

Prepared according to Protocol E. ¹H NMR (400 MHz, CDCl₃) δ 11.97 (s, 1H), 11.46-10.75 (m, 1H), 7.78 (d, J=7.8 Hz, 1H), 7.60 (t, J=7.5 Hz, 1H), 7.49 (t, J=7.7 Hz, 1H), 7.44 (d, J=7.7 Hz, 1H), 7.17 (t, J=7.6 Hz, 1H), 7.08 (d, J=7.6 Hz, 1H), 7.01 (d, J=7.9 Hz, 1H), 6.89 (d, J=7.6 Hz, 1H), 4.24 (s, 2H), 4.18 (s, 2H), 2.32 (d, J=8.3 Hz, 3H). HRMS: m/z calcd for C21H18N2O3F3+ [M+H]:403.1270. found: 403.1266.

161. 1-(5,6-dihydroxy-2-(3-(trifluoromethyl)benzyl)pyrimidin-4-yl)-2-(m-tolyl)ethanone

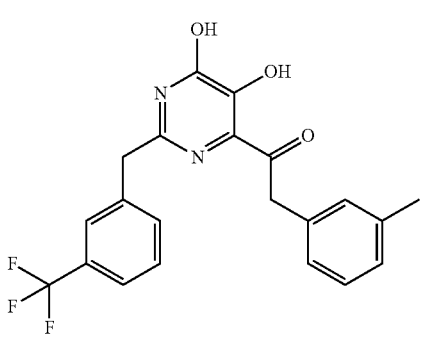 [SMILES: Cc1cccc(CC(=O)c2nc(Cc3cccc(C(F)(F)F)c3)nc(O)c2O)c1]

Prepared according to Protocol E. ¹H NMR (400 MHz, CDCl₃) δ 12.10 (s, 1H), 7.70 (s, 1H), 7.59 (t, J=6.4 Hz, 2H), 7.50 (t, J=7.6 Hz, 1H), 7.21 (t, J=7.6 Hz, 1H), 7.10 (d, J=7.6 Hz, 1H), 7.06 (s, 1H), 7.01 (d, J=7.6 Hz, 1H), 4.29 (d, J=17.3 Hz, 2H), 4.10 (s, 2H), 2.33 (d, J=7.6 Hz, 3H). HRMS: m/z calcd for C21H18N2O3F3+ [M+H]:403.1270. found: 403.1266.

162. 3-hydroxy-2-(2-methoxybenzoyl)-7,8-dihydropyrrolo-[1,2-a]pyrimidin-4(6H)-one

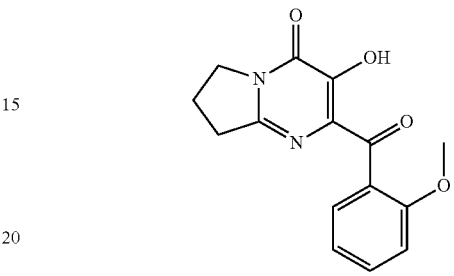

Prepared according to Protocol E. ¹H NMR (400 MHz, CDCl₃) δ 12.21 (s, 1H), 7.56-7.48 (m, 1H), 7.45 (dd, J=7.6, 1.5 Hz, 1H), 7.06 (dt, J=14.4, 6.8 Hz, 2H), 4.24-4.13 (m, 2H), 3.82 (s, 3H), 2.98 (t, J=7.9 Hz, 2H), 2.34-2.20 (m, 2H). HRMS: m/z calcd for C15H15N2O4+ [M+H]:287.1032. found: 287.1028.

163. (5,6-dihydroxy-2-(3-methylbenzyl)pyrimidin-4-yl)(3-methoxyphenyl)methanone

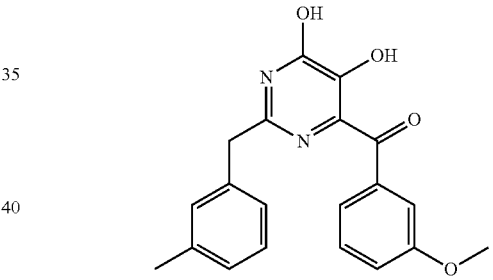

Prepared according to Protocol E. ¹H NMR (400 MHz, CDCl₃) δ 12.63 (s, 1H), 11.05 (s, 1H), 7.92 (d, J=7.7 Hz, 1H), 7.83 (s, 1H), 7.39 (t, J=8.0 Hz, 1H), 7.31-7.24 (m, 1H), 7.22-7.12 (m, 4H), 4.03 (d, J=24.8 Hz, 2H), 3.88 (s, 3H), 2.37 (s, 3H). HRMS: m/z calcd for C20H19N2O4+ [M+H]: 351.1345. found: 351.1343.

164. (5,6-dihydroxy-2-(3-(trifluoromethyl)benzyl)pyrimidin-4-yl)(2-methoxyphenyl)methanone

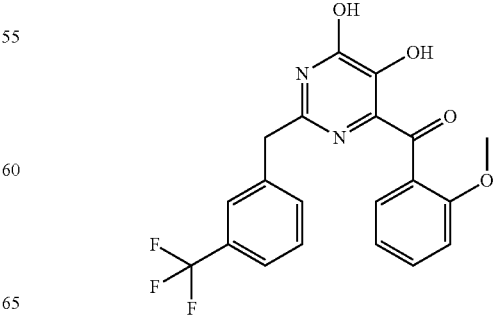

Prepared according to Protocol E. ¹H NMR (400 MHz, CDCl₃) δ 12.70 (s, 1H), 12.15 (s, 1H), 7.58-7.49 (m, 4H), 7.44-7.36 (m, 2H), 7.04 (dd, J=13.5, 6.0 Hz, 1H), 6.94 (d, J=8.4 Hz, 1H), 3.99 (s, 2H), 3.66 (s, 3H). HRMS: m/z calcd for C20H16N2O4F3+ [M+H]:405.1062. found: 405.1068.

165. 1-(5,6-dihydroxy-2-(3-methylbenzyl)pyrimidin-4-yl)-2-(M-tolyl)ethanone

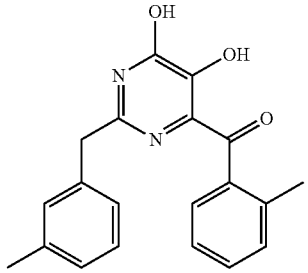

Prepared according to Protocol E. ¹H NMR (400 MHz, CDCl₃) δ 12.05 (s, 1H), 10.26 (s, 1H), 7.27-7.21 (m, 1H), 7.14 (m, 5H), 4.36 (d, J=21.6 Hz, 2H), 3.98 (s, 2H), 2.35 (d, J=15.1 Hz, 6H). HRMS: m/z calcd for C21H21N2O3+ [M+H]: 349.1552. found: 349.1552.

166. (5,6-dihydroxy-2-(2-(trifluoromethyl)phenyl)pyrimidin-4-yl)(o-tolyl)methanone

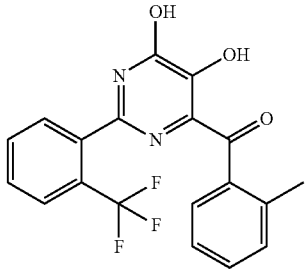 [SMILES: Cc1ccccc1C(=O)c1nc(-c2ccccc2C(F)(F)F)nc(O)c1O]

Prepared according to Protocol E. ¹H NMR (400 MHz, CDCl₃) δ 13.01-12.13 (br s, 1H), 11.23-10.27 (br s, 1H), 7.78 (m, 1H), 7.66 (m, 2H), 7.57 (m, 2H), 7.39 (m, 1H), 7.25 m, 2H), 2.37 (d, J=47.7 Hz, 3H). HRMS: m/z calcd for C19H14N2O3F3+ [M+H]:375.0957. found: 375.0956.

167. (5,6-dihydroxy-2-(5-methylpyridin-2-yl)pyrimidin-4-yl)(o-tolyl)methanone

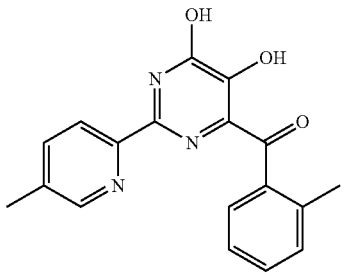

Prepared according to Protocol E. ¹H NMR (400 MHz, CDCl₃) δ 11.47-10.90 (s, 1H), 8.43 (s, 1H), 7.89 (d, J=8.1 Hz, 1H), 7.67 (d, J=7.8 Hz, 1H), 7.61-7.56 (m, 1H), 7.49 (dd, J=10.6, 4.4 Hz, 1H), 7.36 (dd, J=7.5, 4.1 Hz, 2H), 2.47 (d, J=6.7 Hz, 3H), 2.43 (d, J=7.0 Hz, 3H). HRMS: m/z calcd for C18H16N3O3+ [M+H]:322.1192. found: 322.1187.

168. 2-(BIS (4-fluorophenyl)(hydroxy)methyl)-6,7,8,9-tetrahydro-2H-pyrido[1,2-a]pyrimidine-3,4-dione

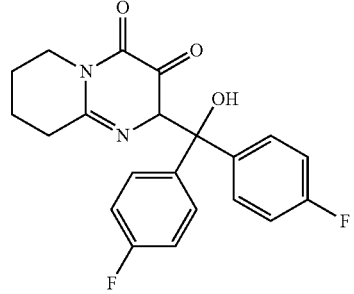 [SMILES: O=C1C(=O)N2CCCCC2=NC1C(O)(c1ccc(F)cc1)c1ccc(F)cc1]

Prepared according to Protocol E2. ¹H NMR (400 MHz, CDCl₃) δ 7.46-7.33 (m, 4H), 7.08-6.95 (m, 4H), 6.28 (s, 1H), 6.17 (s, 1H), 4.02 (t, J=6.2 Hz, 2H), 2.93 (t, J=6.6 Hz, 2H), 2.08-1.97 (m, 2H), 1.97-1.86 (m, 2H).

169. 6-(3-phenyl-1,2,4-oxadiazol-5-yl)-2-(pyridin-2-yl)pyrimidine-4,5-diol

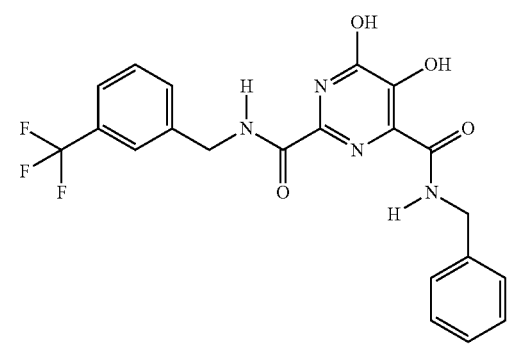 [SMILES: O=C(NCc1cccc(C(F)(F)F)c1)c1nc(O)c(O)c(C(=O)NCc2ccccc2)n1]

Prepared according to Protocol E2. ¹H NMR (400 MHz, CDCl₃) δ13.06 (s, 1H), 10.41 (s, 1H), 7.86 (d, J=23.4, 2H), 7.59-7.43 (m, 4H), 7.38-7.30 (m, 5H), 4.78-4.55 (m, 4H).

170. N4-benzyl-5,6-dihydroxy-N2-(2-methoxyethyl)pyrimidine-2,4-dicarboxamide

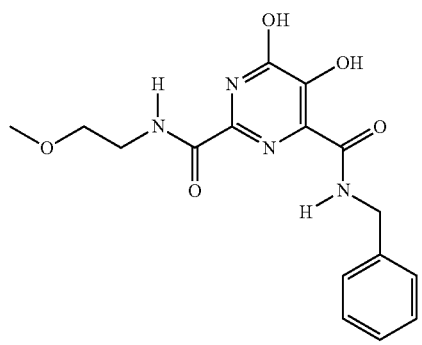 [SMILES: COCCNC(=O)c1nc(O)c(O)c(C(=O)NCc2ccccc2)n1]

Prepared according to Protocol C. ¹H NMR (400 MHz, CDCl₃) δ 13.03 (s, 1H), 10.92-10.12 (m, 1H), 7.81 (d, J=66.2, 2H), 7.40 (d, J=5.8, 5H), 4.69 (d, J=6.2, 2H), 3.74-3.45 (m, 4H), 3.37 (d, J=6.7, 3H).

171. 5,6-dihydroxy-N-isobutyl-2-(morpholine-4-carbonyl)pyrimidine-4-carboxamide

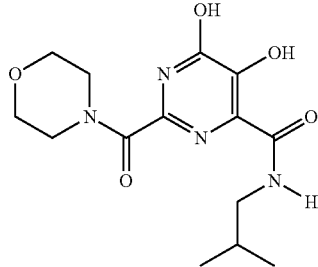 [SMILES: CC(C)CNC(=O)c1nc(C(=O)N2CCOCC2)nc(O)c1O]

Prepared according to Protocol C. ¹H NMR (400 MHz, CDCl₃) δ 4.24 (m, 2H), 3.78 (m, 2H), 3.31 (t, J=6.5 Hz, 2H), 1.92 (dd, J=13.4, 6.6 Hz, 1H), 1.01 (d, J=6.7 Hz, 6H).

172. 5,6-dihydroxy-N4-isobutyl-N2-(3-(trifluoromethyl)benzyl)pyrimidine-2,4-dicarboxamide

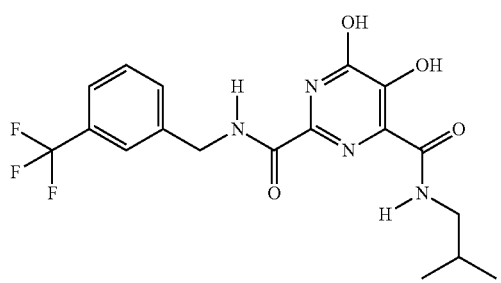 [SMILES: CC(C)CNC(=O)c1nc(C(=O)NCc2cccc(C(F)(F)F)c2)nc(O)c1O]

Prepared according to Protocol C. ¹H NMR (400 MHz, CDCl₃) δ 13.25 (s, 1H), 10.53 (s, 1H), 7.77 (s, 1H), 7.70-7.36 (m, 5H), 4.75 (t, J=13.1, 2H), 3.38-3.19 (m, 2H), 2.04-1.81 (m, 1H), 1.09-0.84 (m, 6H).

173. 5,6-dihydroxy-N4-isobutyl-N2-(2-methoxyethyl)pyrimidine-2,4-dicarboxamide

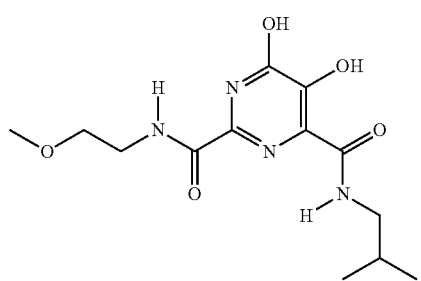 [SMILES: COCCNC(=O)c1nc(O)c(O)c(C(=O)NCC(C)C)n1]

Prepared according to Protocol C. ¹H NMR (400 MHz, CDCl₃) δ 13.01 (s, 1H), 10.80-10.05 (m, 1H), 7.52 (t, J=46.3, 3H), 3.54 (dd, J=10.7, 5.3, 2H), 3.48 (t, J=4.8, 2H), 3.31 (s, 3H), 3.20 (t, J=6.6, 2H), 1.91-1.76 (m, 2H), 0.89 (dd, J=12.3, 5.9, 6H).

174. N4-(4-fluorobenzyl)-5,6-dihydroxy-N2-isobutylpyrimidine-2,4-dicarboxamide

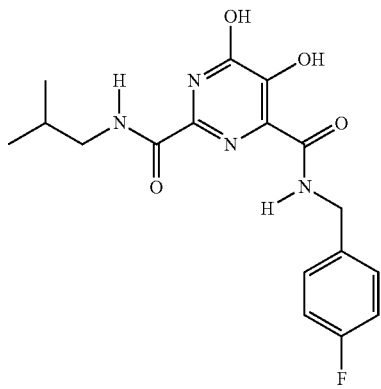 [SMILES: CC(C)CNC(=O)c1nc(O)c(O)c(C(=O)NCc2ccc(F)cc2)n1]

Prepared according to Protocol C. ¹H NMR (400 MHz, CDCl₃) δ 7.36 (dd, J=8.5, 5.4 Hz, 2H), 7.10 (t, J=8.6 Hz, 2H), 4.66 (d, J=6.3 Hz, 2H), 3.27 (t, J=6.7 Hz, 2H), 1.91 (dd, J=13.5, 6.8 Hz, 1H), 0.97 (d, J=6.7 Hz, 6H).

175. N4-(4-fluorobenzyl)-5,6-dihydroxy-N2-(3-(trifluoromethyl)benzyl)pyrimidine-2,4-dicarboxamide

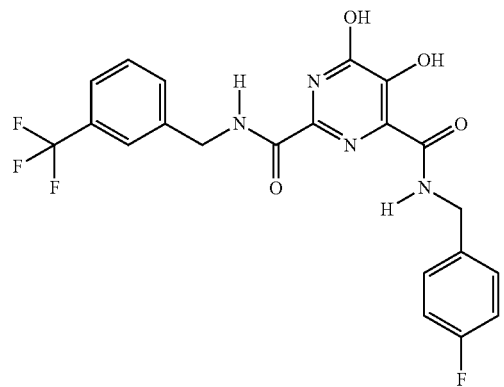 [SMILES: O=C(NCc1cccc(C(F)(F)F)c1)c1nc(O)c(O)c(C(=O)NCc2ccc(F)cc2)n1]

Prepared according to Protocol C. ¹H NMR (400 MHz, CDCl₃) δ 13.01 (s, 1H), 10.49 (s, 1H), 7.87 (d, J=22.2, 2H), 7.51 (d, J=17.1, 5H), 7.02 (d, J=8.3, 3H), 4.65 (d, J=28.3, 4H).

176. N4-(4-fluorobenzyl)-5,6-dihydroxy-N2-(2-methoxyethyl)pyrimidine-2,4-dicarboxamide

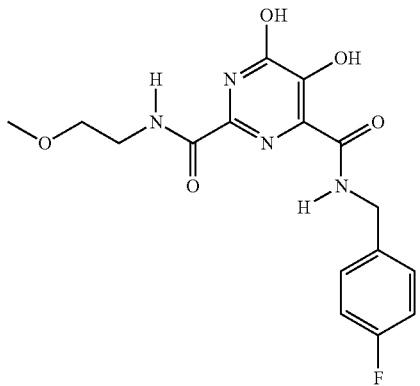 [SMILES: COCCNC(=O)c1nc(O)c(O)c(C(=O)NCc2ccc(F)cc2)n1]

Prepared according to Protocol C. $^1$H NMR (400 MHz, CDCl$_3$) δ 13.38-12.54 (s, 1H), 10.91-10.05 (s, 1H), 7.85 (s, 1H), 7.69 (s, 1H), 7.37 (dd, J=8.6, 5.3, 2H), 7.09 (t, J=8.6, 2H), 4.65 (d, J=6.2, 2H), 3.64 (dd, J=10.3, 5.9, 2H), 3.60-3.54 (m, 2H), 3.38 (s, 3H).

177. 6-(3-phenyl-1,2,4-oxadiazol-5-yl)-2-(pyridin-2-yl)pyrimidine-4,5-diol

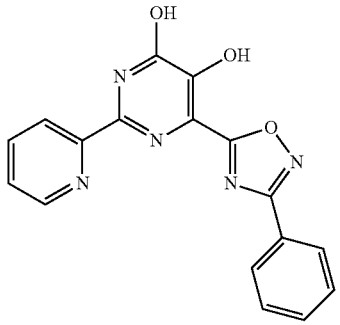 [SMILES: Oc1nc(-c2ccccn2)nc(-c2nc(-c3ccccc3)no2)c1O]

Prepared according to Protocol C. $^1$H NMR (400 MHz, DMSO) δ 8.57 (s, 1H), 8.41 (d, J=7.8 Hz, 1H), 8.10 (d, J=7.8 Hz, 2H), 7.85 (d, J=8.9 Hz, 1H), 7.48 (s, 3H), 7.36 (s, 1H).

178. 2-(pyridin-2-yl)-6-(3-(3-(trifluoromethyl)phenyl)-1,2,4-oxadiazol-5-yl)pyrimidine-4,5-diol

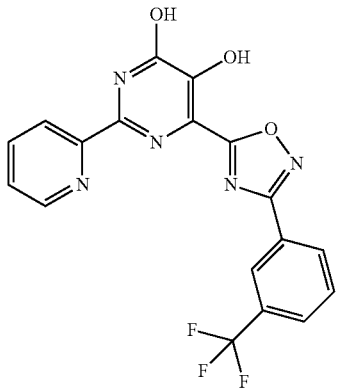 [SMILES: Oc1nc(-c2ccccn2)nc(-c2nc(-c3cccc(C(F)(F)F)c3)no2)c1O]

Prepared according to Protocol G. $^1$H NMR (400 MHz, DMSO) δ 8.58 (s, 1H), 8.37 (d, J=14.0 Hz, 3H), 7.86 (s, 2H), 7.66 (s, 1H), 7.38 (s, 1H).

179. 2-(pyridin-2-yl)-6-(3-(thiophen-2-yl)-1,2,4-oxadiazol-5-yl)pyrimidine-4,5-diol

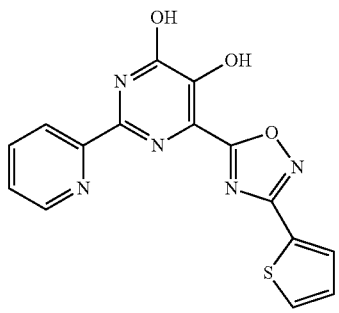 [SMILES: Oc1nc(-c2ccccn2)nc(-c2nc(-c3cccs3)no2)c1O]

Prepared according to Protocol G. $^1$H NMR (400 MHz, DMSO) δ 8.54 (d, J=5.0 Hz, 1H), 8.34 (d, J=8.1 Hz, 1H), 7.81 (d, J=3.7 Hz, 2H), 7.52 (d, J=4.0 Hz, 1H), 7.37-7.27 (m, 1H), 7.17-7.08 (m, 1H).

180. 6-(3-butyl-1,2,4-oxadiazol-5-yl)-2-(3-methylpyridin-2-yl)pyrimidine-4,5-diol

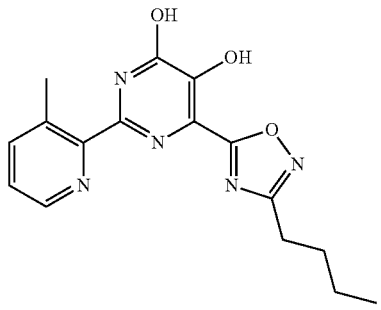 [SMILES: CCCCc1noc(-c2nc(-c3ncccc3C)nc(O)c2O)n1]

Prepared according to Protocol G. $^1$H NMR (400 MHz, CDCl$_3$) δ 11.66 (s, 1H), 10.59 (s, 1H), 8.52 (d, J=2.9 Hz, 1H), 7.73 (d, J=7.7 Hz, 1H), 7.39 (dd, J=7.7, 4.6 Hz, 1H), 3.0 (s, 3H), 3.0-2.90 (m, 2H), 1.99-1.8 (m, 2H), 1.49 (dd, J=14.9, 7.4 Hz, 2H), 1.01 (dd, J=8.7, 6.0 Hz, 3H).

181. 2-(3-methylpyridin-2-yl)-6-(3-phenyl-1,2,4-oxadiazol-5-yl)pyrimidine-4,5-diol

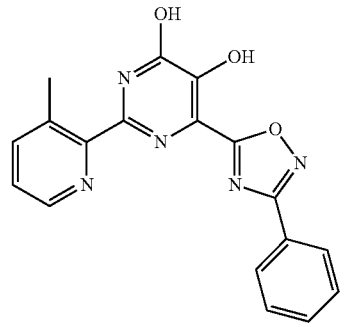 [SMILES: Cc1cccnc1-c1nc(O)c(O)c(-c2nc(-c3ccccc3)no2)n1]

Prepared according to Protocol G. $^1$H NMR (400 MHz, DMSO) δ 8.44 (s, 1H), 8.08 (d, J=3.4 Hz, 2H), 7.66 (d, J=6.9 Hz, 1H), 7.48 (s, 3H), 7.29 (s, 1H), 2.82 (s, 3H).

182. 2-(3-methylpyridin-2-yl)-6-(3-(thiophen-2-yl)-1,2,4-oxadiazol-5-yl)pyrimidine-4,5-diol

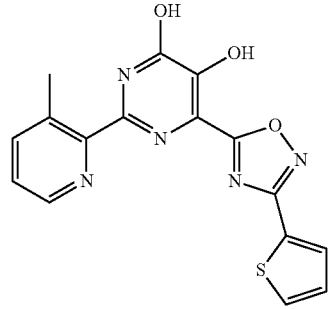 [SMILES: Cc1cccnc1-c1nc(O)c(O)c(-c2nc(-c3cccs3)no2)n1]

Prepared according to Protocol G. $^1$H NMR (400 MHz, DMSO) δ 12.28 (s, 1H), 11.40-10.86 (br s, 1H), 8.49 (m, 1H), 7.98-7.78 (m, 2H), 7.71 (m, 1H), 7.64 (s, 1H), 7.37 m, 1H), 7.19 (m, 1H), 2.79 (d, J=2.5 Hz, 3H).

183. 2-(3-methylpyridin-2-yl)-6-(3-(p-tolyl)-1,2,4-oxadiazol-5-yl)pyrimidine-4,5-diol

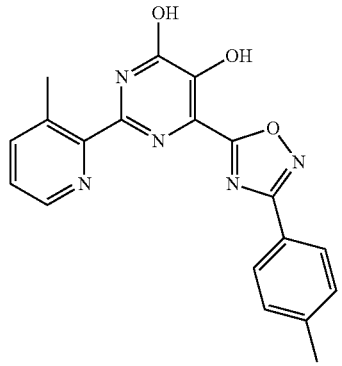 [SMILES: Cc1ccc(-c2noc(-c3nc(-c4ncccc4C)nc(O)c3O)n2)cc1]

Prepared according to Protocol G. $^1$H NMR (400 MHz, CDCl$_3$) δ 11.59 (s, 1H), 10.52 (s, 1H), 8.43 (d, J=3.5 Hz, 1H), 7.96 (d, J=8.2 Hz, 2H), 7.65 (d, J=7.7 Hz, 1H), 7.29 (d, J=7.8 Hz, 3H), 2.90 (s, 3H), 2.39 (s, 3H).

184. 6-(3-butyl-1,2,4-oxadiazol-5-yl)-2-(3-(trifluoromethyl)phenyl)pyrimidine-4,5-diol

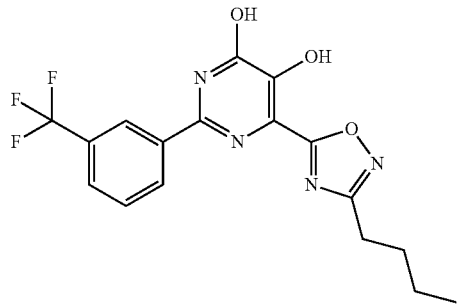 [SMILES: CCCCc1noc(-c2nc(-c3cccc(C(F)(F)F)c3)nc(O)c2O)n1]

Prepared according to Protocol G. $^1$H NMR (400 MHz, DMSO) δ 13.40 (s, 1H), 11.28-10.33 (br s, 1H), 8.42 (s, 1H), 8.36 (d, J=7.9 Hz, 1H), 7.93 (s, 2H), 7.74 (d, J=7.9 Hz, 1H), 7.64 (t, J=7.8 Hz, 1H), 2.86-2.76 (m, 2H), 1.74 (dt, J=15.1, 7.5 Hz, 2H), 1.46-1.31 (m, 2H), 0.92 (t, J=7.4 Hz, 3H).

185. 6-(5-fluoro-1H-benzo[D]imidazol-2-yl)-2-(3-(trifluoromethyl)phenyl)pyrimidine-4,5-diol

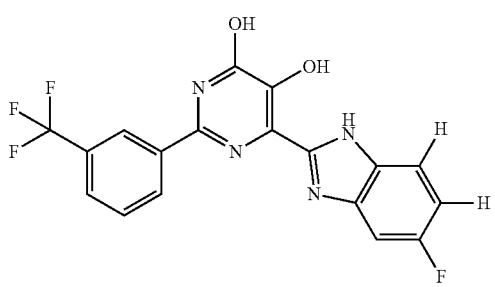 [SMILES: Oc1nc(-c2cccc(C(F)(F)F)c2)nc(-c2nc3cc(F)ccc3[nH]2)c1O]

Prepared according to Protocol G. $^1$H NMR (400 MHz, DMSO) δ 8.61 (s, 1H), 8.47 (d, J=8.0 Hz, 1H), 7.70 (d, J=8.1 Hz, 1H), 7.60 (t, J=6.7 Hz, 2H), 7.29 (d, J=10.5 Hz, 2H), 7.01 (s, 1H).

186. Ethyl 2-(5,6-dihydroxy-2(3-(trifluoromethyl)phenyl)pyrimidin-4-yl)-1H-benzo[D]imidazole-5-carboxylate

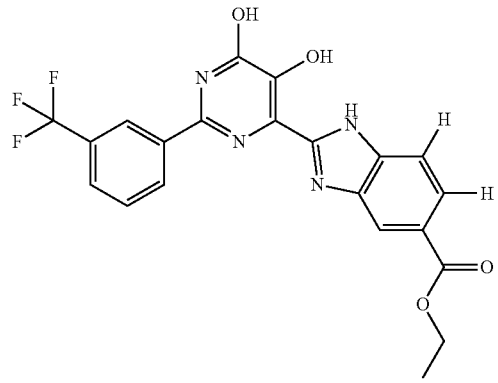 [SMILES: CCOC(=O)c1ccc2[nH]c(-c3nc(-c4cccc(C(F)(F)F)c4)nc(O)c3O)nc2c1]

Prepared according to Protocol F. $^1$H NMR (400 MHz, DMSO) δ 13.29 (s, 1H), 13.11 (s, 1H), 8.64 (s, 1H), 8.54 (d, J=7.7 Hz, 1H), 8.38 (s, 1H), 8.29 (s, 1H), 7.95 (s, 1H), 7.73 (d, J=7.7 Hz, 1H), 7.65 (t, J=7.7 Hz, 1H), 4.34 (q, J=7.0 Hz, 2H), 1.38 (t, J=7.1 Hz, 3H).

187. 6-(5-fluoro-1H-benzo[D]imidazol-2-yl)-2-(3-(trifluoromethyl)phenyl)pyrimidine-4,5-diol

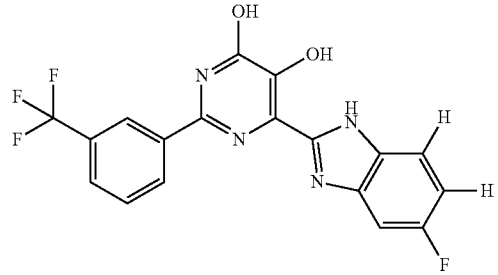

Prepared according to Protocol F. $^1$H NMR (400 MHz, DMSO) δ 13.00 (s, 1H), 8.62 (s, 1H), 8.49 (d, J=7.9 Hz, 1H), 7.70 (d, J=7.8 Hz, 1H), 7.61 (m, 2H), 7.31 (s, 1H), 7.01 (dd, J=12.8, 5.5 Hz, 1H).

188. Ethyl 2-(5,6-dihydroxy-2-(pyridin-2-yl)pyrimidin-4-yl)-1H-benzo[D]imidazole-5-carboxylate

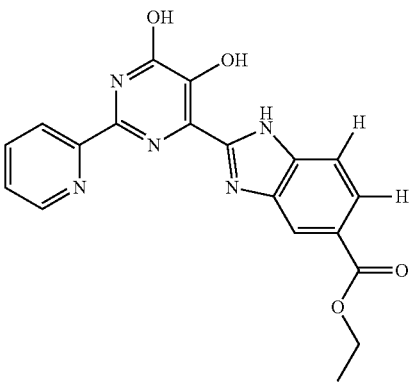 [SMILES: CCOC(=O)c1ccc2[nH]c(-c3nc(-c4ccccn4)nc(O)c3O)nc2c1]

Prepared according to Protocol F. ¹H NMR (400 MHz, DMSO) δ 13.47-13.01 (m, 2H), 11.60 (s, 2H), 8.68 (s, 1H), 8.64 (d, J=4.3 Hz, 1H), 8.40-8.26 (m, 1H), 7.95 (m, 3H), 7.51-7.42 (m, 1H), 4.34 (q, J=7.1 Hz, 2H), 1.38 (t, J=7.1 Hz, 3H).

189. 6-(5-fluoro-1H-benzo[D]imidazol-2-yl)-2-(4-fluorophenyl)pyrimidine-4,5-diol

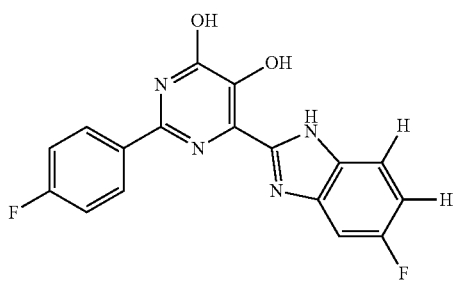

Prepared according to Protocol F. ¹H NMR (400 MHz, DMSO) δ 13.08 (s, 1H), 12.88 (s, 1H), 8.45-8.24 (m, 2H), 7.62 (m, 1H), 7.26 (m, 1H), 7.20 (m, 2H), 7.04 (s, 1H).

190. N-(5-(benzyloxy)-4-hydroxy-6-(5-methylisoxazol-3-yl)pyrimidin-2-yl)-4-(tert-butyl)-N-methylbenzamide

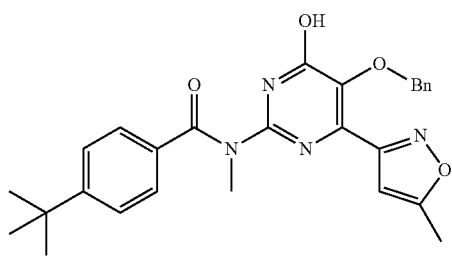 [SMILES: Cc1cc(-c2nc(N(C)C(=O)c3ccc(C(C)(C)C)cc3)nc(O)c2OCc2ccccc2)no1]

Prepared according to Protocol D. ¹H NMR (400 MHz, CDCl₃) δ 14.73 (br s, 1H), 8.19-8.12 (m, 2H), 7.42-7.32 (m, 3H), 7.32-7.23 (m, 2H), 7.18 (m, 2H), 6.42 (d, J=1.1 Hz, 1H), 5.16 (s, 2H), 3.61 (s, 3H), 2.35 (d, J=1.0 Hz, 3H), 1.27 (s, 9H).

191. +/−trans-N-(5-(benzyloxy)-4-hydroxy-6-(pyridin-2-yl)pyrimidin-2-yl)-4-isopropylcyclohexanecarboxamide

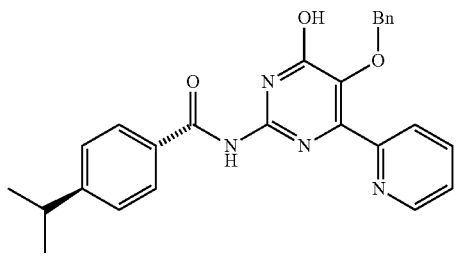

Prepared according to Protocol D. ¹H NMR (400 MHz, MeOD) δ 8.58 (s, 1H), 8.40 (s, 1H), 7.73 (t, J=8.0 Hz, 1H), 7.31 (d, J=20.2 Hz, 3H), 7.15 (s, 3H), 5.21 (s, 2H), 2.31 (s, 1H), 1.90 (d, J=12.7 Hz, 2H), 1.76 (s, 2H), 1.45 (m, 4H), 1.01 (s, 4H), 0.79 (dd, J=9.3, 6.8 Hz, 6H).

192. 4-(tert-butyl)-N-(4,5-dihydroxy-6-(5-methyl-isoxazol-3-yl)pyrimidin-2-yl)-N-methylbenzamide

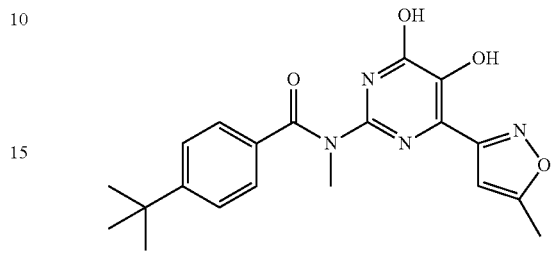

Prepared according to Protocol D. ¹H NMR (400 MHz, CD₃OD) δ 15.02 (s, 1H), 13.34 (s, 1H), 8.28-7.99 (m, 2H), 7.38 (dd, J=10.9, 8.3 Hz, 2H), 6.65 (s, 1H), 3.67 (s, 3H), 2.46 (s, 3H), 1.28 (s, 9H).

193. 4-(tert-butyl)-N-(5-hydroxy-1-methyl-4-(5-methylisoxazol-3-yl)-6-oxo-1,6-dihydropyrimidin-2-yl)benzamide

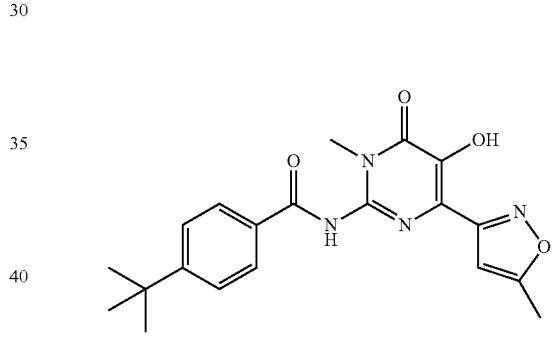

Prepared according to Protocol D. ¹H NMR (400 MHz CD₃OD) δ 8.63 (s, 1H), 7.97 (br s, 1H), 7.55-7.31 (m, 4H), 6.50 (s, 1H), 3.45 (s, 3H), 2.45 (s, 3H), 1.28 (s, 9H).

194. +/−trans-N-(4,5-dihydroxy-6-(pyridin-2-yl)pyrimidin-2-yl)-4-isopropylcyclohexanecarboxamide

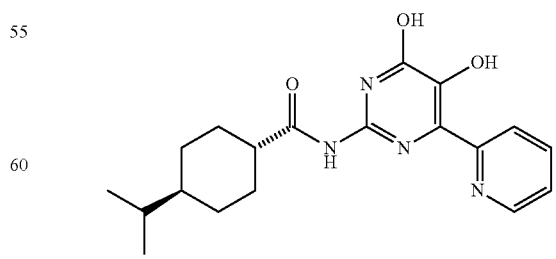

Prepared according to Protocol D. ¹H NMR (400 MHz, CD₃OD) δ 8.51 (d, J=4.9 Hz, 1H), 8.26 (d, J=8.2 Hz, 1H), 7.94 (t, J=7.8 Hz, 1H), 7.39 (s, 1H), 2.29 (s, 1H), 1.88 (d, J=12.7 Hz, 2H), 1.76 (m, 2H), 1.45 (m, 3H), 1.1 (m, 3H), 0.81 (d, J=6.8 Hz, 6H).

195. 4-(tert-butyl)-N-(4,5-dihydroxy-6-(piperidin-2-yl)pyrimidin-2-yl)benzamide

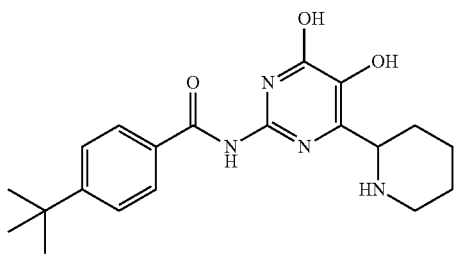 [SMILES: CC(C)(C)c1ccc(C(=O)Nc2nc(O)c(O)c(C3CCCCN3)n2)cc1]

Prepared according to Protocol D. For this example, deprotection using palladium on carbon hydrogenation conditions afforded the reduced pyridine analog. $^1$H NMR (400 MHz, DMSO) δ 8.00 (d, J=8.4 Hz, 2H), 7.49 (d, J=7.9 Hz, 2H), 3.9 (m, 1H), 3.1 (m, 2H), 1.81 (m, 2H), 1.62 (m, 1H), 1.49 (s, 3H), 1.31 (s, 9H).

196. N-(4,5-dihydroxy-6-(pyridin-2-yl)pyrimidin-2-yl)-4-methylcyclohexanecarboxamide

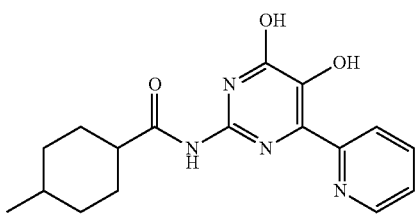 [SMILES: CC1CCC(C(=O)Nc2nc(O)c(O)c(-c3ccccn3)n2)CC1]

Prepared according to Protocol D. $^1$H NMR (400 MHz, CDCl$_3$) δ 8.49 (s, 1H), 8.12 (d, J=7.9 Hz, 1H), 7.83 (d, J=1.8 Hz, 1H), 7.33-7.26 (m, 1H), 2.43 (s, 1H), 2.18 (s, 1H), 2.0-1.2 (m, 8H), 0.90 (d, J=6.8 Hz, 1.5H), 0.86 (d, J=6.5 Hz, 1.5H).

197. 4-(tert-butyl)-N-(4,5-dihydroxy-6-(pyridin-2-yl)pyrimidin-2-yl)benzamide

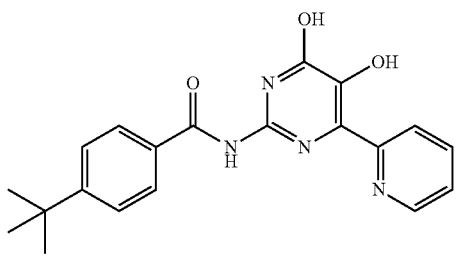 [SMILES: CC(C)(C)c1ccc(C(=O)Nc2nc(O)c(O)c(-c3ccccn3)n2)cc1]

Prepared according to Protocol D. $^1$H NMR (400 MHz, CDCl$_3$) δ 12.22 (s, 1H), 11.1 (br s, 1H), 8.47 (d, J=4.3 Hz, 1H), 8.16 (d, J=7.8 Hz, 1H), 7.97 (d, J=8.2 Hz, 1H), 7.81 (d, J=8.2 Hz, 2H), 7.48 (d, J=6.5 Hz, 2H), 7.41 (d, J=8.4 Hz, 1H), 7.34-7.26 (m, 1H), 1.29 (s, 9H).

198. N-benzyl-2-(4,5-dihydroxy-6-(5-methylisoxazol-3-yl)pyrimidin-2-yl)acetamide

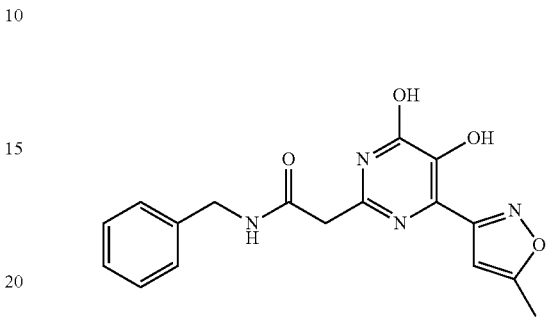

Prepared according to Protocol A. $^1$H NMR (400 MHz, DMSO) δ 11.41 (brs, 1H), 8.46 (brs, 1H), 7.40 (t, J=7.8H, 1H), 7.29 (m, 3H), 7.06 (d, J=6.8 Hz, 2H), 6.31 (s, 1H), 5.88 (brs, 2H), 4.23 (d, J=5.7 Hz, 2H), 2.39 (s, 3H).

199. N-benzyl-4,5-dihydroxy-6-(1-methyl-1H-imidazol-4-yl)pyrimidine-2-carboxamide

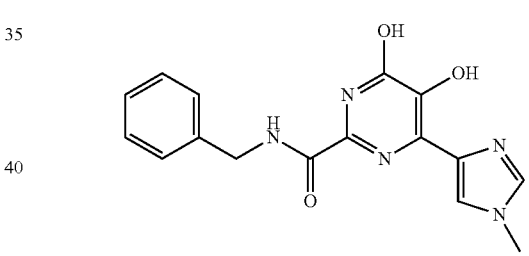

Prepared according to Protocol A. $^1$H NMR (400 MHz, DMSO) δ 9.38 (t, J=6.7 Hz, 1H), 7.96 (d, J=7.3 Hz, 2H), 7.34 (d, J=4.5 Hz, 4H), 7.26 (s, 1H), 4.49 (d, J=6.3 Hz, 2H), 3.80 (s, 3H).

200. 4-(tert-butyl)-N-(5-hydroxy-6-oxo-4-(2H-tetrazol-5-yl)-1,6-dihydropyrimidin-2-yl)benzamide

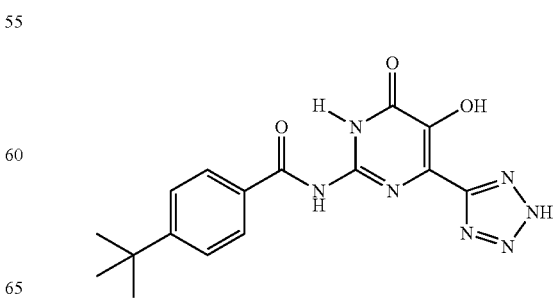

Prepared according to Protocol A. $^1H$ NMR (400 MHz, DMSO) δ 12.69 (br s, 1H), 11.85 (s, 1H), 8.14 (d, J=8.2 Hz, 2H), 7.68 (d, J=8.5 Hz, 2H), 6.64 (brs, 1H), 1.44 (s, 9H).

201. 4-(tert-butyl)-N-(5-hydroxy-4-(3-hydroxyisoxazol-5-yl)-6-oxo-1,6-dihydropyrimidin-2-yl)benzamide

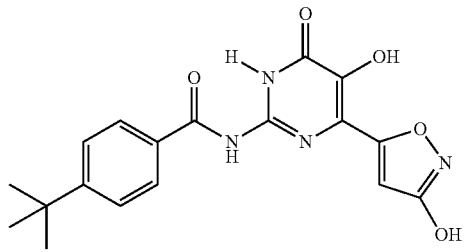 [SMILES: CC(C)(C)c1ccc(C(=O)Nc2nc(-c3cc(O)no3)c(O)c(=O)[nH]2)cc1]

Prepared according to Protocol A. $^1H$ NMR (400 MHz, DMSO) δ 8.04 (d, J=8.3 Hz, 2H), 7.63 (d, J=8.4 Hz, 2H), 6.22 (s, 1H), 1.34 (s, 9H).

C. Example Compounds

Table 1 provides a listing of exemplary compounds of the present invention. The listing of compounds in Table 1 is not limiting of the compounds or methods of the present invention, but is illustrative of compounds that form the present invention or can be used in connection with the present invention.

Lengthy table referenced here

US09328075-20160503-T00001

Please refer to the end of the specification for access instructions.

D. Screening

An increased throughput dual-luciferase reporter IRdRp gene assay is used in screening the compounds of the present invention. In the assay, 293T cells are transfected with four IRdRp plasmids containing the genes for PB2, PB1, PA and NP from the strain A/Vietnam/1203/04 (H1N1). Additionally, the firefly luciferase reporter plasmid (pLuci), under the control of an influenza M gene segment, and a renilla luciferase reporter plasmid (phRL-CMV) under the control of a CMV promoter, are transfected. Twenty-four hours later, the luciferase levels reflect the expression and resulting activity of IRdRp. It is the renilla luciferase expression levels that are used to normalize for transfection efficiency. Inhibition of IRdRp by the screened compounds is measured by reduced firefly luciferase levels relative to the renilla luciferase levels. As a control, ribavirin was a positive control, as a known anti-IRdRp agent when converted to the corresponding triphosphate in vitro.

10 μM of compound is initially used in the screens, with the following criteria acting as positive hits if the compound inhibition of the firefly reporter is greater than 30%. Based on the above initial screening, compounds are then subjected to dose response studies, with ribavirin used as the control. $EC_{50}$ values of less than 30 μM and tightly fitted dose response curves determined positive hits.

Once these are completed, the compound is subjected to a growth inhibition study using A/Puerto Rico/8/34 (H1N1). This assay uses near confluent MDCK cell monolayers grown in 24-well plates. The plates are washed with viral growth medium and then are infected with 1 mL of virus stock dilution (multiplicity of infection (MOI)=0.01). The cells are inculated for an hour, and unbound virus is removed by washing the cells with viral growth media. Cells are supplemented with fresh growth media containing the test compound (20 μM) and 1 ug/mL of TPCK-treated trypsin. The compounds are tested in triplicate. Cells are then incubated at 35 degrees C. Supernatant aliquots are removed at 24 and 48 hours post infection to determine viral titers.

As further screening of compounds, a preliminary viral replication dose response study is carried out. Oseltamivir acid and DMSO are used as positive and negative controls, respectively, in 96 well plates seeded with MDCK cells. Each well has an MOI of 0.04 with A/Puerto Rico/8/34 (H1N1) and the compounds in varying amounts. A three fold dilution of compound, starting at 20 μM, is used, and each dilution is duplicated. After a 24 hour incubation, virus amounts are determined by hemagglutination assay. When there is at least an eight-fold drop in HA titer in comparison to untreated wells, the score is inhibition. This assay provides results indicating anti-influenza activity in vitro. As alternative virus strains to test, A/Brosbame/59/07 (H1N1, A/Brisbane/10/07 (H3N2) and B/Brisbane/60/08 are useful. Additionally, H1N1 virus A/California/4/09 and H9N2 and H7N7 avian influenza viruse strains are useful, as well.

E. Cytotoxicity Testing

A cell ine cytotox assay of HEK-293 embryo kidney cells, MDCK cells are used. Results are read at 72 hours. The HEK293, MDCK cell lines are available to be purchased from the American Type Culture Collection (ATCC, Manassas, Va.). The culturing of these cells is per the recommendations from ATCC. The cell media are also available from the ATCC. The MycoAlert Mycoplasma Detection Kit available from Lonza is used to test for contamination.

Cells are exponentially grown in plates of Corning 384 wells and incubated overnight at 37 degrees C. in a humidified, 5% CO2 incubator. DMSO inhibitor stock solution is added the next day to a final concentration of 25 uM, 0.25% DMSO and diluted to a third for a total of ten concentrations. A Promega Cell Titer Gio Reagent is used to determine cytotoxicity after a 72 hour incubation period. Luminescence is measured using an Envision plate reader available from Perkin Elmer.

Summary of the results for compounds from both the screen and the dose response of the focused compound library are provided in Table 2. For examples deemed inactive, only percent inhibition of the Firefly reporter activity at 10 μM is shown in brackets. ND means not determined. Active compounds $IC_{50}$ displayed in μM, with follow-up growth response percentage at 20 μM (48 hours), cytotoxicity in both HEK293 and MDCK cell lines, and in a few cases solubility measurements for a select few are displayed.

TABLE 2
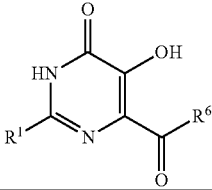
| R¹ | R⁶ | Mini-Genome Firefly IC50 μM | Growth Inhibition (%) 20 μM 48 h | HEK293 Cytotox CC₅₀ μM | MDCK Cytotox CC₅₀ μM | Solubility PBS (pH 7.4) μM | AVG SOL PBS (pH 7.4) mg/mL |
|---|---|---|---|---|---|---|---|
| 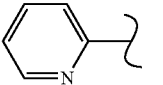 | 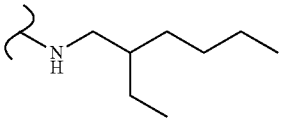 | 4.3 | 94 | <25 | >25 | 54.6 | 18.8 |
| 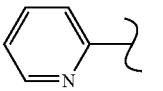 | 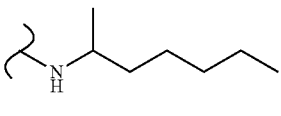 | 14.1 | 88 | <25 | >25 | ND | ND |
| 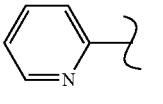 | 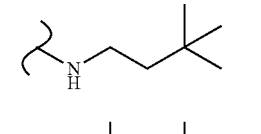 | 10.1 | 88 | <25 | >25 | ND | ND |
| 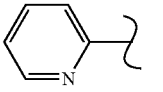 | 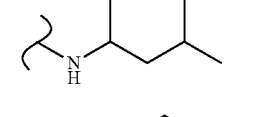 | 12.9 | 50 | >25 | >25 | ND | ND |
| Phenyl | 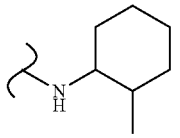 | [2.1%] | ND | ND | ND | ND | ND |
| 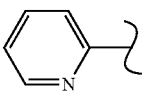 | 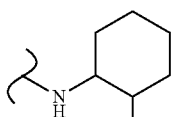 | 5.5 | 97 | <25 | 5.5 | ND | ND |
| 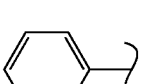 | 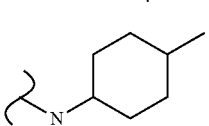 | 5.6 | 88 | <25 | >25 | 64.2 | 21.0 |
| 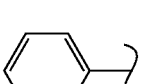 | 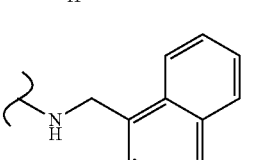 | 9.1 | 94 | <25 | >25 | 2.3 | 0.9 |
| 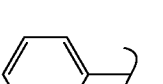 | 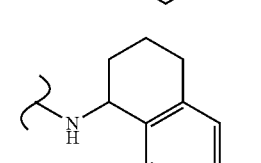 | 3.6 | 97 | 2.6 | 7.0 | 64.5 | 23.4 |
| 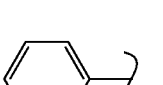 | 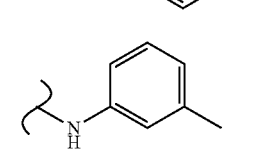 | 27.1 | 75 | <25 | >25 | ND | ND |

TABLE 2-continued
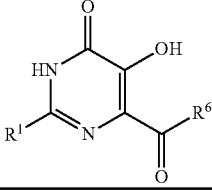
| R¹ | R⁶ | Mini-Genome Firefly IC50 μM | Growth Inhibition (%) 20 μM 48 h | HEK293 Cytotox CC₅₀ μM | MDCK Cytotox CC₅₀ μM | Solubility PBS (pH 7.4) μM | AVG SOL PBS (pH 7.4) mg/mL |
|---|---|---|---|---|---|---|---|
| 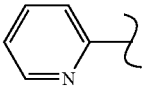 | 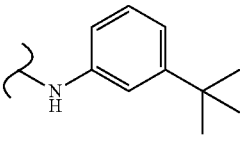 | 5.9 | 94 | <25 | >25 | ND | ND |
| 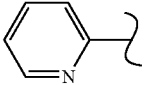 | 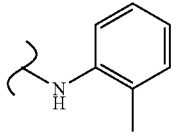 | 8.9 | 94 | >25 | >25 | ND | ND |
| 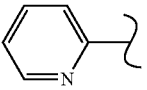 | 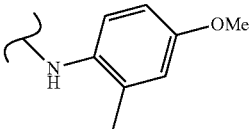 | 10.0 | 0 | <25 | >25 | ND | ND |
| 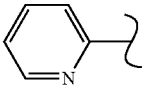 | 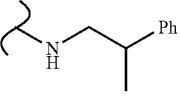 | 20.5 | 50 | <25 | >25 | ND | ND |
| 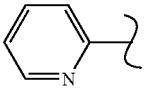 | 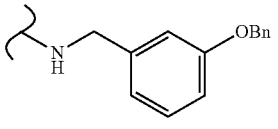 | [10.0%] | ND | ND | ND | ND | ND |
| 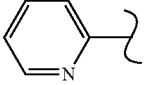 | 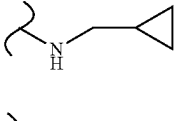 | [12.5%] | ND | ND | ND | ND | ND |
| 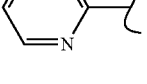 | 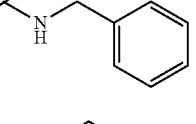 | [7.4%] | ND | ND | ND | ND | ND |
| 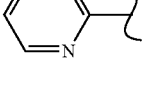 | 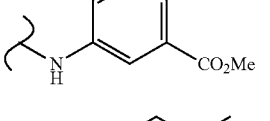 | [7.8%] | ND | ND | ND | ND | ND |
| 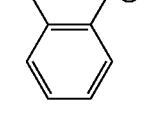 | 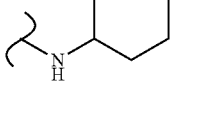 | [7.6%] | ND | ND | ND | ND | ND |
| 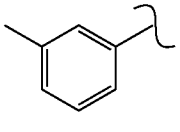 | 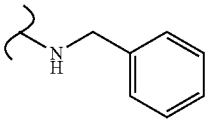 | [0%] | ND | ND | ND | ND | ND |

TABLE 2-continued

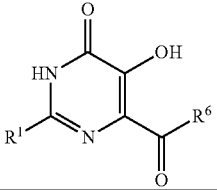

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

LENGTHY TABLES

The patent contains a lengthy table section. A copy of the table is available in electronic form from the USPTO web site (http://seqdata.uspto.gov/?pageRequest=docDetail&DocID=US09328075B2). An electronic copy of the table will also be available from the USPTO upon request and payment of the fee set forth in 37 CFR 1.19(b)(3).

What is claimed is:

1. A compound of the formula:

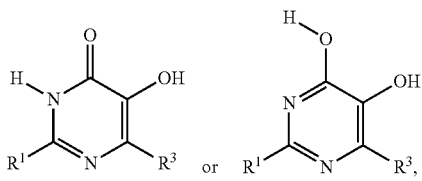

wherein $R^1$ is an optionally substituted heteroaryl;
wherein $R^3$ is optionally substituted and selected from cycloalkyl, heterocycloalkyl, aryl, heteroaryl, —CONR$^4$R$^5$, and —COR$^6$;
wherein $R^4$ and $R^5$ are each optionally substituted and independently selected from hydrogen, alkyl, heteroalkyl, cycloalkyl, heterocycloalkyl, aryl, and heteroaryl; wherein at least one of $R^4$ or $R^5$ is not hydrogen, and provided that when $R^1$ is a heteroaryl group having 6 or more ring members, then neither $R^3$ nor $R^4$ is hydrogen; or wherein —NR$^4$R$^5$ together form an optionally substituted ring selected from piperidinyl, morpholinyl, and piperazinyl; and
wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, and oxazolyl, or a pharmaceutically acceptable salt thereof.

2. A method for treating influenza in a subject, the method comprising: administering to the subject an effective amount of the compound of claim 1, or a pharmaceutically acceptable salt thereof, thereby treating the influenza.

3. The method of claim 2, wherein the compound is an endonuclease inhibitor.

4. The method of claim 2, wherein the compound is a RNA dependent RNA polymerase inhibitor.

5. The method of claim 2, wherein the influenza is Influenza A.

6. The method of claim 2, wherein the influenza is Influenza B.

7. The method of claim 2, wherein the influenza is H1N1, H2N2, H3N2, H5N1, or any combination of H1N1, H2N2, H3N2, and H5N1.

8. The method of claim 2, wherein the influenza is drug resistant.

9. A therapeutic method comprising co-administration of one or more treatments selected from Oseltamavir, Zanamivir, Amantadine, Rimantadine, Arbidol, Laninamivir, Peramivir, Vitamin D, and an interferon, with one or more compounds of claim 1, or a pharmaceutically acceptable salt thereof.

10. The method of claim 9, wherein the one or more treatments and the one or more compounds are administered simultaneously.

11. The method of claim 9, wherein the one or more treatments and the one or more compounds are administered in a single pharmaceutical composition.

12. The compound of claim 1, wherein $R^3$ is a five-membered heterocycle selected from:

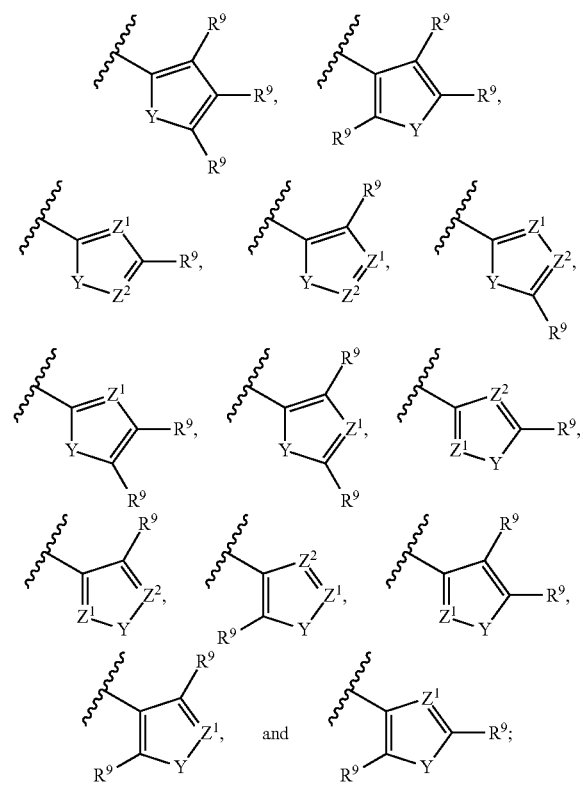

wherein Y is selected from O, S, and N—$R^8$;
wherein $Z^1$ is selected from N and C—$R^9$; and
wherein $Z^2$ is selected from N and C—$R^9$,
wherein each $R^8$ is independently selected from hydrogen, methyl, ethyl, propyl, and butyl; and
wherein each $R^9$ is independently selected from hydrogen, cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl.

13. The compound of claim 1, wherein $R^3$ is a six-membered heterocycle selected from:

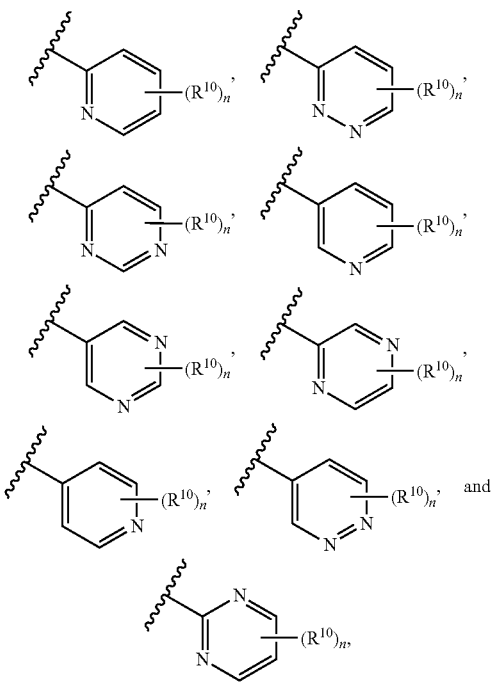

wherein n is an integer from 0-2; and
wherein each $R^{10}$ is independently selected from hydrogen, cyano, acyl, fluoro, chloro, bromo, iodo, methyl, ethyl, propyl, butyl, pentyl, hexyl, hydroxyl, acetoxyl, methoxyl, ethoxyl, propoxyl, and butoxyl.

14. The method of claim 2, wherein the compound is an influenza endonuclease inhibitor.

15. The method of claim 9, wherein the compound is an endonuclease inhibitor.

16. The method of claim 9, wherein the compound is an influenza endonuclease inhibitor.

17. The compound of claim 1, wherein the compound is an endonuclease inhibitor.

18. The compound of claim 1, wherein the compound is an influenza endonuclease inhibitor.

19. A compound of the formula:

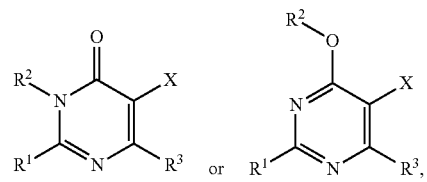

wherein X is selected from hydroxyl, fluoro, chloro, bromo, —$OR^7$, —$NR^{11}R^{12}$, —$NR^{11}COR^{12}$, —$NR^{11}CO_2R^{12}$, and —$NR^{11}CONR^{12}R^{13}$;
wherein $R^1$ is optionally substituted heteroaryl;
wherein $R^2$ is optionally substituted and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl;
wherein $R^3$ is optionally substituted and selected from cycloalkyl; heterocycloalkyl; aryl or heteroaryl, provided that $R^1$ and $R^2$ do not form a ring together with the carbon and nitrogen to which they are attached; —CONR$^4$R$^5$, and —COR$^6$;

wherein $R^4$ and $R^5$ are each optionally substituted and independently selected from hydrogen, alkyl, heteroalkyl, cycloalkyl, heterocycloalkyl, aryl, and heteroaryl; wherein at least one of $R^4$ or $R^5$ is not hydrogen, and provided that when $R^1$ is an aryl or heteroaryl group having 6 or more ring members, then neither $R^3$ nor $R^4$ is hydrogen; or wherein —NR$^4$R$^5$ together form an optionally substituted ring selected from piperidinyl, morpholinyl, and piperazinyl;

wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, and oxazolyl;

wherein $R^7$ is selected from alkyl, heteroalkyl, cycloalkyl, heterocycloalkyl, aryl, and heteroaryl; and wherein each of $R^{11}$, $R^{12}$, and $R^{13}$, when present, is independently selected from hydrogen, alkyl, heteroalkyl, cycloalkyl, heterocycloalkyl, aryl, and heteroaryl;

or a pharmaceutically acceptable salt thereof, wherein the compound is an endonuclease inhibitor.

20. The compound of claim 19, wherein X is hydroxyl.

21. The compound of claim 19, wherein $R^2$ is hydrogen.

22. A method for treating influenza in a subject, the method comprising: administering to the subject an effective amount of the compound of claim 19, or a pharmaceutically acceptable salt thereof, thereby treating influenza.

23. A therapeutic method comprising co-administration of one or more treatments selected from Oseltamavir, Zanamivir, Amantadine, Rimantadine, Arbidol, Laninamivir, Peramivir, Vitamin D, and an interferon, with one or more compounds of the formula:

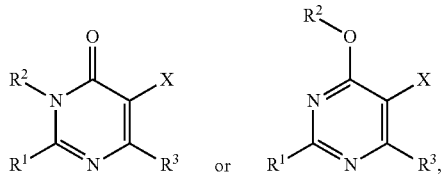

wherein X is selected from hydroxyl, fluoro, chloro, bromo, —OR$^7$, —NR$^{11}$R$^{12}$, —NR$^{11}$COR$^{12}$, —NR$^{11}$CO$_2$R$^{12}$, and —NR$^{11}$CONR$^{12}$R$^{13}$;

wherein $R^1$ is optionally substituted and selected from heteroaryl, aryl-substituted alkyl, heteroaryl-substituted alkyl, —NR$^{11}$R$^{12}$, —NR$^{11}$COR$^{12}$, —NR$^{11}$CO$_2$R$^{12}$, —NR$^{11}$CONR$^{12}$R$^{13}$, —COR$^{11}$, —CONR$^{12}$R$^{13}$, and —OR$^7$;

wherein $R^2$ is optionally substituted and selected from hydrogen, alkyl, heteroalkyl, cycloalkyl, heterocycloalkyl, aryl, and heteroaryl; or wherein $R^1$ and $R^2$ together form an optionally substituted ring with the carbon and nitrogen to which they are attached, selected from pyrrolidinyl, imidazolidinyl, hexahydropyrimidinyl, 1,3,5-triazinanyl, and piperidinyl;

wherein $R^3$ is optionally substituted and selected from cycloalkyl; heterocycloalkyl; aryl or heteroaryl, provided that $R^1$ and $R^2$ do not form a ring together with the carbon and nitrogen to which they are attached; —CONR$^4$R$^5$, and —COR$^6$;

wherein $R^4$ and $R^5$ are each optionally substituted and independently selected from hydrogen, alkyl, heteroalkyl, cycloalkyl, heterocycloalkyl, aryl, and heteroaryl; wherein at least one of $R^4$ or $R^5$ is not hydrogen, and provided that when $R^1$ is an aryl or heteroaryl group having 6 or more ring members, then neither $R^3$ nor $R^4$ is hydrogen; or wherein —NR$^4$R$^5$ together form an optionally substituted ring selected from piperidinyl, morpholinyl, and piperazinyl;

wherein $R^6$ is optionally substituted and selected from alkyl, heteroalkyl, cycloalkyl, heterocycloalkyl, phenyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, thienyl, isoxazolyl, thiazolyl, and oxazolyl;

wherein $R^7$ is selected from alkyl, heteroalkyl, cycloalkyl, heterocycloalkyl, aryl, and heteroaryl; and wherein each of $R^{11}$, $R^{12}$, and $R^{13}$, when present, is independently selected from hydrogen, alkyl, heteroalkyl, cycloalkyl, heterocycloalkyl, aryl, and heteroaryl;

or a pharmaceutically acceptable salt thereof, wherein the compound is an endonuclease inhibitor.

24. The method of claim 19, wherein $R^1$ is selected from 2-pyridinyl and 1-methyl-1H-imidazole.

25. The method of claim 23, wherein $R^1$ is heteroaryl.

26. The method of claim 23, wherein $R^1$ is selected from 2-pyridinyl and 1-methyl-1H-imidazole.

* * * * *